(12) United States Patent
Bhat et al.

(10) Patent No.: US 9,688,985 B2
(45) Date of Patent: *Jun. 27, 2017

(54) MICRORNA COMPOUNDS AND METHODS FOR MODULATING MIR-21 ACTIVITY

(71) Applicant: Regulus Therapeutics Inc., San Diego, CA (US)

(72) Inventors: Balkrishen Bhat, San Diego, CA (US); Eric Marcusson, San Francisco, CA (US)

(73) Assignee: Regulus Therapeutics Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/995,432

(22) Filed: Jan. 14, 2016

(65) Prior Publication Data

US 2016/0244753 A1 Aug. 25, 2016

Related U.S. Application Data

(62) Division of application No. 14/597,676, filed on Jan. 15, 2015, now Pat. No. 9,267,137, which is a division of application No. 13/869,177, filed on Apr. 24, 2013, now Pat. No. 8,969,317.

(60) Provisional application No. 61/741,783, filed on Apr. 25, 2012, provisional application No. 61/717,927, filed on Oct. 24, 2012, provisional application No. 61/779,913, filed on Mar. 13, 2013.

(51) Int. Cl.
| | |
|---|---|
| *C12N 15/11* | (2006.01) |
| *C12N 15/113* | (2010.01) |
| *A61K 31/712* | (2006.01) |
| *A61K 45/06* | (2006.01) |

(52) U.S. Cl.
CPC .......... *C12N 15/113* (2013.01); *A61K 31/712* (2013.01); *A61K 45/06* (2013.01); *C12N 15/1135* (2013.01); *C12N 2310/11* (2013.01); *C12N 2310/113* (2013.01); *C12N 2310/141* (2013.01); *C12N 2310/315* (2013.01); *C12N 2310/322* (2013.01); *C12N 2310/3341* (2013.01); *C12N 2310/343* (2013.01); *C12N 2310/346* (2013.01); *C12N 2320/30* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 7,582,744 B2 | 9/2009 | Manoharan et al. |
| 8,017,763 B2 | 9/2011 | Manoharan et al. |
| 8,110,558 B2 | 2/2012 | Bennett et al. |
| 8,211,867 B2 | 7/2012 | Bennett et al. |
| 8,236,777 B2 | 8/2012 | Thum et al. |
| 8,404,659 B2 | 3/2013 | Kauppinen et al. |
| 8,466,120 B2 | 6/2013 | Lollo et al. |
| 8,592,389 B2 | 11/2013 | Thum et al. |
| 8,697,663 B2 | 4/2014 | Bennett et al. |
| 8,912,161 B2 | 12/2014 | Bhat |
| 8,969,317 B2 | 3/2015 | Bhat et al. |
| 9,012,423 B2 | 4/2015 | Duffield et al. |
| 9,181,547 B2 | 11/2015 | Bhat |
| 9,267,137 B2 | 2/2016 | Bhat et al. |
| 9,359,609 B2 | 6/2016 | Duffield et al. |
| 2009/0192102 A1 | 7/2009 | Bader et al. |
| 2013/0289093 A1 | 10/2013 | Bhat et al. |
| 2014/0100263 A1 | 4/2014 | Duffield et al. |
| 2014/0107183 A1 | 4/2014 | Bhat |
| 2014/0329887 A1 | 11/2014 | Bhat |
| 2015/0218558 A1 | 8/2015 | Duffield et al. |
| 2015/0299704 A1 | 10/2015 | Duffield et al. |
| 2016/0138016 A1 | 5/2016 | Bhat |
| 2016/0244753 A1 | 8/2016 | Bhat et al. |

FOREIGN PATENT DOCUMENTS

| | | |
|---|---|---|
| EP | 2261333 | 12/2010 |
| WO | WO 03/029459 | 4/2003 |
| WO | WO 2005/013901 | 2/2005 |
| WO | WO 2006/069584 | 7/2006 |
| WO | WO 2006/118806 | 12/2006 |
| WO | WO 2006/137941 | 12/2006 |
| WO | WO 2007/027894 | 3/2007 |
| WO | WO 2007/090073 | 8/2007 |
| WO | WO 2007/112753 | 10/2007 |
| WO | WO 2007/112754 | 10/2007 |
| WO | WO 2008/043521 | 4/2008 |
| WO | WO 2008/086807 | 7/2008 |
| WO | WO 2008/151631 | 12/2008 |
| WO | WO 2009/043353 | 4/2009 |
| WO | WO 2009/058907 | 5/2009 |
| WO | WO 2009/091972 | 7/2009 |
| WO | WO 2009/106367 | 9/2009 |

(Continued)

OTHER PUBLICATIONS

Akkina et al., "MicroRNAs in kidney function and disease," Transl Res, Elsevier, Amsterdam, NL, 2011, 157: 236-240.
Boulanger et al., "Anti-miR-21 as a Potential Novel Therapy for both Early and Late Stages of Alport Syndrome," Kidney Week Presentation, Nov. 15, 2014, 12 pages.
Boulanger et al., "Identification of the Pathologic Role of miR-21 in Alport's Kidney Disease," Abstract No. FR-P0697, Kidney Week 2013, 1 page.
Boulanger et al., "Identification of the Pathologic Role of miR-21 in Alport's Kidney Disease," Kidney Week 2013 Poster, Nov. 8, 2013, 1 page.

(Continued)

*Primary Examiner* — Kate Poliakova-Georgantas
(74) *Attorney, Agent, or Firm* — McNeill Baur PLLC

(57) ABSTRACT

Described herein are compositions and methods for the inhibition of miR-21 activity. The compositions have certain nucleoside modification patterns that yield potent inhibitors of miR-21 activity. The compositions may be used to inhibit miR-21, and also to treat diseases associated with abnormal expression of miR-21, such as fibrosis and cancer.

6 Claims, 8 Drawing Sheets

(56) References Cited

FOREIGN PATENT DOCUMENTS

| WO | WO 2010/099161 | 9/2010 |
|---|---|---|
| WO | WO 2010/144485 | 12/2010 |
| WO | WO 2011/126842 | 10/2011 |
| WO | WO 2012/148952 | 11/2012 |
| WO | WO 2013/013165 | 1/2013 |
| WO | WO 2013/163258 | 10/2013 |
| WO | WO 2013/192576 | 12/2013 |
| WO | WO 2014/048441 | 4/2014 |
| WO | WO 2014/058881 | 4/2014 |

OTHER PUBLICATIONS

Chan et al., "MicroRNA-21 is an Antiapoptotic Factor in Human Glioblastoma Cells," Cancer Res., 2005, 65:6029-6033.
Chau, "microRNAs—Novel Therapeutic Targets for Kidney Diseases," ASN Kidney Week 2011, Philadelphia, PA, Presentation, Nov. 8, 2011, 24 pages.
Chau et al., "MicroRNA-21 Promotes Fibrosis of the Kidney by Silencing Metabolic Pathways," Sci Transl Med., 2012, 4:121ra18.
Chen et al., "Relation between MicroRNA Expression in Peritoneal Dialysis Effluent and Peritoneal Transport Characteristics," Dis Markers, 2012, 33:35-42.
Cosgrove, "Glomerular pathology in Alport syndrome: a molecular perspective," Pediatr Nephrol, 2011, 27:885-890.
Davis et al., "Improved targeting of miRNA with antisense oligonucleotides," Nucleic Acids Res., 2006, 34:2294-2304.
Duffield, "MicroRNAs are Novel Therapeutic Targets to Treat Kidney Injury and Fibrosis," Presentation, Kidney Week, Atlanta, GA, Nov. 5-10, 2013, 31pages.
Duffield, "Mitochondiral Dysfunction in the Progression of Chronic Kidney Disease," Renal Grand Rounds, Seattle, WA, Sep. 20, 2013, 44 pages.
Duffield et al., "Inhibition of microRNA-21 as a Therapeutic Strategy for Kidney Fibrosis," Abstract SA-OR449, Kidney Week 2011, 1 page.
Esau, "Inhibition of microRNA with antisense oligonucleotides," Methods, 2008, 44:55-60.
Godwin et al., "Identification of a microRNA signature of renal ischemia reperfusion injury," PNAS, 2010, 107:14339-14444.
Gomez et al., "Anti-miR21 Protects Collagen 4A3 Deficient Mice from Progression of Alport Disease," Abstract SA-PO1134, Kidney Week 2012, 1 page.
Gomez et al., "Anti-miR21 Protects Collagen IV-alpha(3) Deficient Mice from Progression of Alport Disease," Kidney Week 2012 Poster, Nov. 2012, 1 page.
Gomez et al., "Anti-miR21 Protects Collagen 4A3 Deficient Mice from Progression of Alport Disease by Decreasing Oxidative Stress," Abstract SA-OR094, Kidney Week 2013, 1 page.
Gomez et al., "Anti-micro-RNA-21 rescues kidney function in Alport Nephropathy," Kidney Week 2013 Presentation, Nov. 2013, 16 pages.
Gomez et al., " Anti-microRNA-21 oligonucleotides prevent Alport nephropathy progression by stimulating metabolic pathways," J Clin Invest., 2015, 125:141156.
Gomez et al., "Anti-miR21 Protects Collagen IVa(3) Deficient Mice from Progression of Alport Disease," Poster, Keystone Symposium, Mar. 23-28, 2014, 1 Page.
Gross et al., "Treatment of Alport syndrome: beyond animal models," Kidney Int, 2009, 76:599-603.
Krutzfeldt et al., "Specificity, duplex degradation and subcellular localization of antagomirs," Nucleic Acid Res., 2007, 35(9):2885-2892.
Liu et al., "miR-21 mediates fibrogenic activation of pulmonary fibroblasts and lung fibrosis," J Exp Med., 2010, 207:1589-1597.
MacKenna, "micorRNA control of human disease: Utility of miR-21 as an anti-fibrotic approach in kidney," Experimental Biology 2012 Presentation, 20 pages.
MacKenna et al., "Inhibition of microRNA-21 as a Therapeutic Strategy for Kidney Fibrosis," Kidney Week 2011, 13 pages.
MacKenna et al., "Inhibition of microRNA-21 as a Therapeutic Strategy for Kidney Fibrosis," Abstract SA-OR449, Kidney Week 2011, 1 page.
MacKenna et al., "Inhibition of miR-21 as an anti-fibrotic agent in Chronic Kidney Disease," Poster, Keystone Symposium, Mar. 30-Apr. 4, 2012, 1 page.
MacKenna et al., "Inhibition of miR-21 with RG-012 improves renal function and survival in multiple strains of Col4A3 deficient mice," Poster, 10th Annual Meeting of the Oligonucleotide Therapeutics Society, Oct. 12-15, 2014, 1 page.
MacKenna, "microRNA Therapeutics to Treat Alport Syndrome," Presentation, 2nd Orphan Drugs Research & Commercialization Conference, Feb. 21, 2014, 15 pages.
Meng et al., MicroRNA-21 Regulates Expression of the PTEN Tumor Suppressor Gene in Human Hepatocellular Cancer, Gastroenterology, 2007, 133:647-658.
Milam et al., "PPAR-γ agonists inhibit profibrotic phenotypes in human lung fibroblasts and bleomycin-induced pulmonary fibrosis," Am J Physiol Lung Cell Mol Physiol, 2008, 294:L891-L901.
Noone et al., "An update on the pathomechanisms and future therapies of Alport syndrome," Pediatr Nephrol, 2012, 28: 1025-1036.
Patrick et al., "Response to Thum et al.," J Clin Invest, 2011, 121(2):462-463.
Patrick et al., "Stress-dependent cardiac remodeling occurs in the absence of microRNA-21 in mice," J Clin Invest, 2010, 120(11):3912-3916.
Regulus Therapeutics, "Regulus Therapeutics to Present New In Vivo Data for microRNA-21 in Kidney Fibrosis," Press Release, Regulus Therapeutics, Nov. 8, 2011, 2 pages.
Regulus Therapeutics, "Regulus Presents New Preclinical Data on miR-21 at Kidney Week 2012," Press Release, Regulus Therapeutics, Nov. 3, 2012, 2 pages.
Regulus Therapeutics, "Regulus Presents Positive Preclinical Data Demonstrating that microRNA-21 Plays an Important Role in Alport Syndrome," Press Release, Regulus Therapeutics, Nov. 8, 2013, 2 pages.
Rubel et al., "Anti-microRNA21 therapy on top of ACE-inhibition enhances nephroprotection," Poster, American Society of Nephrology Kidney Week, Nov. 11-16, 2014, 1 page.
Saal et al., "MicroRNAs and the kidney: coming of age," Curr Opin Nephrol Hy, 2009, 18: 317-323.
Szeto et al., "Micro-RNA Expression in the Urinary Sediment of Patients with Chronic Kidney Diseases," Dis Markers, 2012, 33: 137-144.
Thum et al., "Comparison of different miR-21 inhibitor chemistries in a cardiac disease model," J Clin Invest, 2011, 121:461-462.
Thum et al., "MicroRNA-21 contributes to myocardial disease by stimulating MAP kinase signalling in fibroblasts," Nature, 2008, 456:980-986.
Wynn, "Common and unique mechanisms regulate fibrosis in various fibroproliferative diseases," J Clin Invest., 2007, 117:524-529.
Zarjou et al, "Identification of microRNA signature in renal fibrosis: role of miR-21," Am J Physiol Renal Physiol, 2011, 301:F793-F801.
Zhong et al., " Smad3-Mediated Upregulation of miR-21 Promotes Renal Fibrosis," J Am Soc Nephrol, 2011, including supplemental data 22:1668-1681.
International Search Report and Written Opinion for PCT/US2012/034880, mailed Jul. 25, 2012, 15 pages.
International Search Report and Written Opinion for PCT/US2012/037913, mailed Aug. 21, 2013, 15 pages.
International Search Report and Written Opinion for PCT/US2013/063884, mailed Jan. 16, 2014, 13 pages.
File history for U.S. Appl. No. 14/111,976, international filed Apr. 25, 2012.
File history of U.S. Appl. No. 13/869,177, filed Apr. 24, 2013.
File history of U.S. Appl. No. 14/048,827, filed Oct. 8, 2013.
File history of U.S. Appl. No. 14/444,406, filed Jul. 28, 2014.
File history of U.S. Appl. No. 14/597,676, filed Jan. 15, 2015.
Androsavich et al., "Novel Methodology for Assessing Inhibition of MicroRNA-21 by RG-012, a MicroRNA Therapeutic in Develop-

(56) References Cited

OTHER PUBLICATIONS ment for the Treatment of Kidney Dysfunction in Patients with Alport Syndrome," Abstract SA-PO539, Kidney Week 2015, Oct. 2015, 1 page.
Androsavich et al., "Novel Methodology for Assessing Inhibition of MicroRNA-21 by RG-012, a MicroRNA Therapeutic in Development for the Treatment of Kidney Dysfunction in Patients with Alport Syndrome," Kidney Week 2015 Poster, Nov. 7, 2015, 1 page.
Blem et al., "A Natural History Study to Observe Disease Progression, Standard of Care, and Investigate Biomarkers in Alport Syndrome Patients," Abstract PUB119, Kidney Week 2015, Oct. 2015, 1 page.
Grundy et al., "Nonclinical Pharmacokinetics and Toxicokinetics of RG-012, an Inhibitor of MicroRNA-21 Being Investigated for Treatment of Alport Syndrome," Kidney Week 2015 Poster, Nov. 7, 2015, 1 page.
Grundy et al., "Nonclinical Pharmacokinetics and Toxicokinetics of RG-012, an Inhibitor of MicroRNA-21 Being Investigated for Treatment of Alport Syndrome," Abstract SA-PO538, Kidney Week 2015, Oct. 2015, 1 page.
Regulus Therapeutics, "Regulus and Sanofi Present New Data Enhancing the Preclinical Profile of RG-012, an Anti-miR Targeting microRNA-21 for the Treatment of Renal Dysfunction in Alport Syndrome Patients, at ASN's Kidney Week 2014 Meeting," Press Release, Regulus Therapeutics, Nov. 15, 2014, 3 pages.
Regulus Therapeutics, "Regulus Initiates Phase I Clinical Study of RG-012, a microRNA Therapeutic in Development for the Treatment of Alport Syndrome," Press Release, Regulus Therapeutics, Jun. 4, 2015, 3 pages.
Regulus Therapeutics, "Regulus to Present Additional Preclinical Data Supporting RG-012 as a Novel microRNA Therapeutic in Development for Alport Syndrome at ASN's Kidney Week 2015," Press Release, Regulus Therapeutics, Oct. 5, 2015, 3 pages.
File history of U.S. Appl. No. 14/677,387, filed Apr. 2, 2015.
File history of U.S. Appl. No. 14/883,055, filed Oct. 14, 2015.
File history of U.S. Appl. No. 14/995,432, filed Jan. 14, 2016.
Gross et al., Kongress für Nephrologie, 8th Annual Meeting of the German Society of Nephrology, Oral Presentation, Rate of Progression in Renal Failure and Renal Biomarkers in Patients with Alport Syndrome: Interim Results from the prospective, non-interventional Athena Study, Sep. 10-13, 2016, 10 pages.
Grundy et al., ERA-EDTA 2016 Congress, Abstract SP257, Treatment with the MicroRNA-21 Inhibitor RG-012 Given with and without Ramipril Delays Renal Impairment Progression and Prolongs Survival when Initiated up to Chronic Kidney Disease (CKD) Stage 3 in a Mouse Model of Alport Syndrome, May 2016, 1 page.
Grundy et al., ERA-EDTA 2016 Congress, Poster SP257, Treatment with the MicroRNA-21 Inhibitor RG-012 Given with and without Ramipril Delays Renal Impairment Progression and Prolongs Survival when Initiated up to Chronic Kidney Disease (CKD) Stage 3 in a Mouse Model of Alport Syndrome, May 2016, 1 page.
Grundy et al., ERA-EDTA 2016 Congress, Abstract SP283, Renal Impairment Effects on Plasma and Tissue Exposure of Unconjugated and Galnac-conjugated Anti-miRs in a Chronic Kidney Disease (CKD) Mouse Model, May 2016, 1 page.
Grundy et al., ERA-EDTA 2016 Congress, Poster SP283, Renal Impairment Effects on Plasma and Tissue Exposure of Unconjugated and Galnac-conjugated Anti-miRs in a Chronic Kidney Disease (CKD) Mouse Model, May 2016, 1 page.
Rheault et al., ERA-EDTA 2016 Congress, Abstract SP120, Change in Glomerular Filtration Rate and Renal Biomarkers in Patients with Chronic Kidney Disease Due to Alport Syndrome: Interim Results from the Athena Study, a Prospectively Designed Natural History Study, May 2016, 1 page.
Rheault et al., ERA-EDTA 2016 Congress, Poster SP120, Change in Glomerular Filtration Rate and Renal Biomarkers in Patients with Chronic Kidney Disease Due to Alport Syndrome: Interim Results from the Athena Study, a Prospectively Designed Natural History Study, May 2016, 1 page.
Regulus Press Release, "Regulus to Present New RG-012 Data at the 53rd European Renal Association-European Dialysis and Transplant Association (ERA-EDTA) Congress," May 20, 2016, 3 pages.
File History of U.S. Appl. No. 15/151,290, filed May 10, 2016.

SEQUENCE LISTING

<160> NUMBER OF SEQ ID NOS: 55

<210> SEQ ID NO 1
<211> LENGTH: 22
<212> TYPE: RNA
<213> ORGANISM: Homo sapiens

```
<400> SEQUENCE: 1
uagcuuauca gacugauguu ga                                          22

<210> SEQ ID NO 2
<211> LENGTH: 72
<212> TYPE: RNA
<213> ORGANISM: Homo sapiens

<400> SEQUENCE: 2
ugucggguag cuuaucagac ugauguugac uguugaaucu cauggcaaca ccagucgaug   60
ggcugucuga ca                                                     72

<210> SEQ ID NO 3
<211> LENGTH: 19
<212> TYPE: DNA
<213> ORGANISM: Artificial sequence
<220> FEATURE:
<223> OTHER INFORMATION: Synthetic

<400> SEQUENCE: 3
acatcagtct gataagcta                                              19

<210> SEQ ID NO 4
<211> LENGTH: 22
<212> TYPE: DNA
<213> ORGANISM: Artificial sequence
<220> FEATURE:
<223> OTHER INFORMATION: Synthetic

<400> SEQUENCE: 4
tcaacatcag tctgataagc ta                                          22

<210> SEQ ID NO 5
<211> LENGTH: 15
<212> TYPE: DNA
<213> ORGANISM: Artificial sequence
<220> FEATURE:
<223> OTHER INFORMATION: Synthetic

<400> SEQUENCE: 5
cagtctgata agcta                                                  15

<210> SEQ ID NO 6
<211> LENGTH: 16
<212> TYPE: DNA
<213> ORGANISM: Artificial sequence
<220> FEATURE:
<223> OTHER INFORMATION: Synthetic

<400> SEQUENCE: 6
tcagtctgat aagcta                                                 16

<210> SEQ ID NO 7
<211> LENGTH: 15
<212> TYPE: DNA
<213> ORGANISM: Artificial sequence
<220> FEATURE:
<223> OTHER INFORMATION: Synthetic

<400> SEQUENCE: 7
caatctaata agcta                                                  15

<210> SEQ ID NO 8
```

```
<211> LENGTH: 19
<212> TYPE: DNA
<213> ORGANISM: Artificial sequence
<220> FEATURE:
<223> OTHER INFORMATION: Synthetic

<400> SEQUENCE: 8
acatcagtct gataagctt                                                        19

<210> SEQ ID NO 9
<211> LENGTH: 18
<212> TYPE: DNA
<213> ORGANISM: Artificial sequence
<220> FEATURE:
<223> OTHER INFORMATION: Synthetic

<400> SEQUENCE: 9
catcagtctg ataagcta                                                         18

<210> SEQ ID NO 10
<211> LENGTH: 18
<212> TYPE: DNA
<213> ORGANISM: Artificial sequence
<220> FEATURE:
<223> OTHER INFORMATION: Synthetic

<400> SEQUENCE: 10
acatcagtct gataagct                                                         18

<210> SEQ ID NO 11
<211> LENGTH: 15
<212> TYPE: DNA
<213> ORGANISM: Artificial sequence
<220> FEATURE:
<223> OTHER INFORMATION: Synthetic

<400> SEQUENCE: 11
cagtatgata agcta                                                            15

<210> SEQ ID NO 12
<211> LENGTH: 15
<212> TYPE: DNA
<213> ORGANISM: Artificial sequence
<220> FEATURE:
<223> OTHER INFORMATION: Synthetic

<400> SEQUENCE: 12
cagtataata agcta                                                            15

<210> SEQ ID NO 13
<211> LENGTH: 15
<212> TYPE: DNA
<213> ORGANISM: Artificial sequence
<220> FEATURE:
<223> OTHER INFORMATION: Synthetic

<400> SEQUENCE: 13
caatcaaata agcta                                                            15

<210> SEQ ID NO 14
<211> LENGTH: 19
<212> TYPE: DNA
<213> ORGANISM: Artificial sequence
<220> FEATURE:
<223> OTHER INFORMATION: Synthetic

<400> SEQUENCE: 14
```
aaatctgtct cataataaa                                              19

<210> SEQ ID NO 15
<211> LENGTH: 19
<212> TYPE: DNA
<213> ORGANISM: Artificial sequence
<220> FEATURE:
<223> OTHER INFORMATION: Synthetic

<400> SEQUENCE: 15
ggaatcttaa ctagactac                                              19

<210> SEQ ID NO 16
<211> LENGTH: 19
<212> TYPE: DNA
<213> ORGANISM: Artificial sequence
<220> FEATURE:
<223> OTHER INFORMATION: Synthetic

<400> SEQUENCE: 16
gaataatata acccctggt                                              19

<210> SEQ ID NO 17
<211> LENGTH: 17
<212> TYPE: DNA
<213> ORGANISM: Artificial sequence
<220> FEATURE:
<223> OTHER INFORMATION: Synthetic

<400> SEQUENCE: 17
atcagtctga taagcta                                                17

<210> SEQ ID NO 18
<211> LENGTH: 16
<212> TYPE: DNA
<213> ORGANISM: Artificial sequence
<220> FEATURE:
<223> OTHER INFORMATION: Synthetic

<400> SEQUENCE: 18
tcagtctgat aagcta                                                 16

<210> SEQ ID NO 19
<211> LENGTH: 15
<212> TYPE: DNA
<213> ORGANISM: Artificial sequence
<220> FEATURE:
<223> OTHER INFORMATION: Synthetic

<400> SEQUENCE: 19
cagtctgata agcta                                                  15

<210> SEQ ID NO 20
<211> LENGTH: 14
<212> TYPE: DNA
<213> ORGANISM: Artificial sequence
<220> FEATURE:
<223> OTHER INFORMATION: Synthetic

<400> SEQUENCE: 20
agtctgataa gcta                                                   14

<210> SEQ ID NO 21
<211> LENGTH: 13
<212> TYPE: DNA

```
<213> ORGANISM: Artificial sequence
<220> FEATURE:
<223> OTHER INFORMATION: Synthetic

<400> SEQUENCE: 21
gtctgataag cta                                                        13

<210> SEQ ID NO 22
<211> LENGTH: 12
<212> TYPE: DNA
<213> ORGANISM: Artificial sequence
<220> FEATURE:
<223> OTHER INFORMATION: Synthetic

<400> SEQUENCE: 22
tctgataagc ta                                                         12

<210> SEQ ID NO 23
<211> LENGTH: 11
<212> TYPE: DNA
<213> ORGANISM: Artificial sequence
<220> FEATURE:
<223> OTHER INFORMATION: Synthetic

<400> SEQUENCE: 23
ctgataagct a                                                          11

<210> SEQ ID NO 24
<211> LENGTH: 10
<212> TYPE: DNA
<213> ORGANISM: Artificial sequence
<220> FEATURE:
<223> OTHER INFORMATION: Synthetic

<400> SEQUENCE: 24
tgataagcta                                                            10

<210> SEQ ID NO 25
<211> LENGTH: 18
<212> TYPE: DNA
<213> ORGANISM: Artificial sequence
<220> FEATURE:
<223> OTHER INFORMATION: Synthetic

<400> SEQUENCE: 25
acatcagtct gataagct                                                   18

<210> SEQ ID NO 26
<211> LENGTH: 17
<212> TYPE: DNA
<213> ORGANISM: Artificial sequence
<220> FEATURE:
<223> OTHER INFORMATION: Synthetic

<400> SEQUENCE: 26
acatcagtct gataagc                                                    17

<210> SEQ ID NO 27
<211> LENGTH: 17
<212> TYPE: DNA
<213> ORGANISM: Artificial sequence
<220> FEATURE:
<223> OTHER INFORMATION: Synthetic

<400> SEQUENCE: 27
catcagtctg ataagct                                                    17
```

```
<210> SEQ ID NO 28
<211> LENGTH: 16
<212> TYPE: DNA
<213> ORGANISM: Artificial sequence
<220> FEATURE:
<223> OTHER INFORMATION: Synthetic

<400> SEQUENCE: 28
catcagtctg ataagc                                                          16

<210> SEQ ID NO 29
<211> LENGTH: 16
<212> TYPE: DNA
<213> ORGANISM: Artificial sequence
<220> FEATURE:
<223> OTHER INFORMATION: Synthetic

<400> SEQUENCE: 29
atcagtctga taagct                                                          16

<210> SEQ ID NO 30
<211> LENGTH: 15
<212> TYPE: DNA
<213> ORGANISM: Artificial sequence
<220> FEATURE:
<223> OTHER INFORMATION: Synthetic

<400> SEQUENCE: 30
atcagtctga taagc                                                           15

<210> SEQ ID NO 31
<211> LENGTH: 15
<212> TYPE: DNA
<213> ORGANISM: Artificial sequence
<220> FEATURE:
<223> OTHER INFORMATION: Synthetic

<400> SEQUENCE: 31
tcagtctgat aagct                                                           15

<210> SEQ ID NO 32
<211> LENGTH: 14
<212> TYPE: DNA
<213> ORGANISM: Artificial sequence
<220> FEATURE:
<223> OTHER INFORMATION: Synthetic

<400> SEQUENCE: 32
tcagtctgat aagc                                                            14

<210> SEQ ID NO 33
<211> LENGTH: 14
<212> TYPE: DNA
<213> ORGANISM: Artificial sequence
<220> FEATURE:
<223> OTHER INFORMATION: Synthetic

<400> SEQUENCE: 33
cagtctgata agct                                                            14

<210> SEQ ID NO 34
<211> LENGTH: 13
<212> TYPE: DNA
<213> ORGANISM: Artificial sequence
<220> FEATURE:
```

```
<223> OTHER INFORMATION: Synthetic

<400> SEQUENCE: 34
cagtctgata agc                                                          13

<210> SEQ ID NO 35
<211> LENGTH: 13
<212> TYPE: DNA
<213> ORGANISM: Artificial sequence
<220> FEATURE:
<223> OTHER INFORMATION: Synthetic

<400> SEQUENCE: 35
agtctgataa gct                                                          13

<210> SEQ ID NO 36
<211> LENGTH: 12
<212> TYPE: DNA
<213> ORGANISM: Artificial sequence
<220> FEATURE:
<223> OTHER INFORMATION: Synthetic

<400> SEQUENCE: 36
agtctgataa gc                                                           12

<210> SEQ ID NO 37
<211> LENGTH: 12
<212> TYPE: DNA
<213> ORGANISM: Artificial sequence
<220> FEATURE:
<223> OTHER INFORMATION: Synthetic

<400> SEQUENCE: 37
gtctgataag ct                                                           12

<210> SEQ ID NO 38
<211> LENGTH: 11
<212> TYPE: DNA
<213> ORGANISM: Artificial sequence
<220> FEATURE:
<223> OTHER INFORMATION: Synthetic

<400> SEQUENCE: 38
gtctgataag c                                                            11

<210> SEQ ID NO 39
<211> LENGTH: 11
<212> TYPE: DNA
<213> ORGANISM: Artificial sequence
<220> FEATURE:
<223> OTHER INFORMATION: Synthetic

<400> SEQUENCE: 39
tctgataagc t                                                            11

<210> SEQ ID NO 40
<211> LENGTH: 10
<212> TYPE: DNA
<213> ORGANISM: Artificial sequence
<220> FEATURE:
<223> OTHER INFORMATION: Synthetic

<400> SEQUENCE: 40
tctgataagc                                                              10
```

-continued

```
<210> SEQ ID NO 41
<211> LENGTH: 10
<212> TYPE: DNA
<213> ORGANISM: Artificial sequence
<220> FEATURE:
<223> OTHER INFORMATION: Synthetic

<400> SEQUENCE: 41
ctgataagct                                                              10

<210> SEQ ID NO 42
<211> LENGTH: 14
<212> TYPE: DNA
<213> ORGANISM: Artificial sequence
<220> FEATURE:
<223> OTHER INFORMATION: Synthetic

<400> SEQUENCE: 42
aatctaataa gcta                                                         14

<210> SEQ ID NO 43
<211> LENGTH: 13
<212> TYPE: DNA
<213> ORGANISM: Artificial sequence
<220> FEATURE:
<223> OTHER INFORMATION: Synthetic

<400> SEQUENCE: 43
atctaataag cta                                                          13

<210> SEQ ID NO 44
<211> LENGTH: 12
<212> TYPE: DNA
<213> ORGANISM: Artificial sequence
<220> FEATURE:
<223> OTHER INFORMATION: Synthetic

<400> SEQUENCE: 44
tctaataagc ta                                                           12

<210> SEQ ID NO 45
<211> LENGTH: 11
<212> TYPE: DNA
<213> ORGANISM: Artificial sequence
<220> FEATURE:
<223> OTHER INFORMATION: Synthetic

<400> SEQUENCE: 45
ctaataagct a                                                            11

<210> SEQ ID NO 46
<211> LENGTH: 10
<212> TYPE: DNA
<213> ORGANISM: Artificial sequence
<220> FEATURE:
<223> OTHER INFORMATION: Synthetic

<400> SEQUENCE: 46
taataagcta                                                              10

<210> SEQ ID NO 47
<211> LENGTH: 14
<212> TYPE: DNA
<213> ORGANISM: Artificial sequence
<220> FEATURE:
<223> OTHER INFORMATION: Synthetic
```

<400> SEQUENCE: 47
caatctaata agct                                                         14

<210> SEQ ID NO 48
<211> LENGTH: 13
<212> TYPE: DNA
<213> ORGANISM: Artificial sequence
<220> FEATURE:
<223> OTHER INFORMATION: Synthetic

<400> SEQUENCE: 48
caatctaata agc                                                          13

<210> SEQ ID NO 49
<211> LENGTH: 13
<212> TYPE: DNA
<213> ORGANISM: Artificial sequence
<220> FEATURE:
<223> OTHER INFORMATION: Synthetic

<400> SEQUENCE: 49
aatctaataa gct                                                          13

<210> SEQ ID NO 50
<211> LENGTH: 12
<212> TYPE: DNA
<213> ORGANISM: Artificial sequence
<220> FEATURE:
<223> OTHER INFORMATION: Synthetic

<400> SEQUENCE: 50
aatctaataa gc                                                           12

<210> SEQ ID NO 51
<211> LENGTH: 12
<212> TYPE: DNA
<213> ORGANISM: Artificial sequence
<220> FEATURE:
<223> OTHER INFORMATION: Synthetic

<400> SEQUENCE: 51
atctaataag ct                                                           12

<210> SEQ ID NO 52
<211> LENGTH: 11
<212> TYPE: DNA
<213> ORGANISM: Artificial sequence
<220> FEATURE:
<223> OTHER INFORMATION: Synthetic

<400> SEQUENCE: 52
atctaataag c                                                            11

<210> SEQ ID NO 53
<211> LENGTH: 11
<212> TYPE: DNA
<213> ORGANISM: Artificial sequence
<220> FEATURE:
<223> OTHER INFORMATION: Synthetic

<400> SEQUENCE: 53
tctaataagc t                                                            11

<210> SEQ ID NO 54
<211> LENGTH: 10

```
<212> TYPE: DNA
<213> ORGANISM: Artificial sequence
<220> FEATURE:
<223> OTHER INFORMATION: Synthetic

<400> SEQUENCE: 54
tctaataagc                                                          10

<210> SEQ ID NO 55
<211> LENGTH: 10
<212> TYPE: DNA
<213> ORGANISM: Artificial sequence
<220> FEATURE:
<223> OTHER INFORMATION: Synthetic

<400> SEQUENCE: 55
ctaataagct                                                          10
```

MICRORNA COMPOUNDS AND METHODS FOR MODULATING MIR-21 ACTIVITY

This application is a divisional of U.S. patent application Ser. No. 14/597,676, filed Jan. 15, 2015, which is a divisional of U.S. patent application Ser. No. 13/869,177, filed Apr. 24, 2013, which claims the benefit of U.S. Provisional Application No. 61/741,783, filed Apr. 25, 2012; U.S. Provisional Application No. 61/717,927, filed Oct. 24, 2012; and U.S. Provisional Application No. 61/779,913, filed Mar. 13, 2013; each of which is incorporated by reference herein in its entirety for any purpose.

FIELD OF INVENTION

Provided herein are methods and compositions for the modulation of miR-21 activity.

DESCRIPTION OF RELATED ART

MicroRNAs (microRNAs), also known as "mature microRNA" are small (approximately 18-24 nucleotides in length), non-coding RNA molecules encoded in the genomes of plants and animals. In certain instances, highly conserved, endogenously expressed microRNAs regulate the expression of genes by binding to the 3'-untranslated regions (3'-UTR) of specific mRNAs. More than 1000 different microRNAs have been identified in plants and animals. Certain mature microRNAs appear to originate from long endogenous primary microRNA transcripts (also known as pri-microRNAs, pri-mirs, pri-miRs or pri-pre-microRNAs) that are often hundreds of nucleotides in length (Lee, et al., EMBO J., 2002, 21(17), 4663-4670).

Functional analyses of microRNAs have revealed that these small non-coding RNAs contribute to different physiological processes in animals, including developmental timing, organogenesis, differentiation, patterning, embryogenesis, growth control and programmed cell death. Examples of particular processes in which microRNAs participate include stem cell differentiation, neurogenesis, angiogenesis, hematopoiesis, and exocytosis (reviewed by Alvarez-Garcia and Miska, Development, 2005, 132, 4653-4662).

SUMMARY OF INVENTION

Provided herein are compounds comprising a modified oligonucleotide, wherein the nucleobase sequence of the modified oligonucleotide is complementary to miR-21 and wherein the modified oligonucleotide has a nucleoside pattern described herein.

Provided herein are methods for inhibiting the activity of miR-21 comprising contacting a cell with a compound described herein. In certain embodiments, the cell is in vivo. In certain embodiments, the cell is in vitro.

Provided herein are methods for treating a disease associated with miR-21 comprising administering to a subject having a disease associated with miR-21 a compound described herein. In certain embodiments, the subject is a human. In certain embodiments, the subject is a canine.

The compounds described herein are provided for use in therapy.

Provided herein are compounds comprising a modified oligonucleotide consisting of 8 to 22 linked nucleosides, wherein the nucleobase sequence of the modified oligonucleotide is complementary to miR-21 (SEQ ID NO: 1) and wherein the modified oligonucleotide comprises at least 8 contiguous nucleosides of the following nucleoside pattern III in the 5' to 3' orientation:

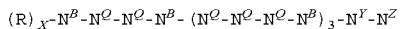

wherein each R is a non-bicyclic nucleoside; X is from 1 to 4; each $N^B$ is a bicyclic nucleoside; each $N^Q$ is a non-bicyclic nucleoside; $N^Y$ is a modified nucleoside or an unmodified nucleoside; and each $N^Z$ is a modified nucleoside.

Provided herein are compounds comprising a modified oligonucleotide consisting of 8 to 19 linked nucleosides, wherein the nucleobase sequence of the modified oligonucleotide is complementary to miR-21 (SEQ ID NO: 1) and wherein the modified oligonucleotide comprises at least 8 contiguous nucleosides of the following nucleoside pattern IV in the 5' to 3' orientation:

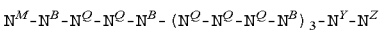

wherein $N^M$ is a modified nucleoside that is not a bicyclic nucleoside; each $N^B$ is a bicyclic nucleoside; each $N^Q$ is a non-bicyclic nucleoside; $N^Y$ is a modified nucleoside or an unmodified nucleoside; and $N^Z$ is a modified nucleoside.

Provided herein are compounds comprising a modified oligonucleotide consisting of 8 to 19 linked nucleosides, wherein the nucleobase sequence of the modified oligonucleotide is complementary to miR-21 (SEQ ID NO: 1) and wherein the modified oligonucleotide comprises at least 8 contiguous nucleosides of the following nucleoside pattern V in the 5' to 3' orientation:

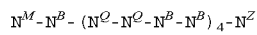

wherein $N^M$ is a modified nucleoside that is not a bicyclic nucleoside; each $N^B$ is a bicyclic nucleoside; each $N^Q$ is a non-bicyclic nucleoside; and $N^Z$ is a modified nucleoside.

Provided herein are compounds comprising a modified oligonucleotide consisting of 8 to 15 linked nucleosides, wherein the nucleobase sequence of the modified oligonucleotide is complementary to miR-21 (SEQ ID NO: 1), and wherein the modified oligonucleotide comprises at least 8 contiguous nucleosides of the following nucleoside pattern VI in the 5' to 3' orientation:

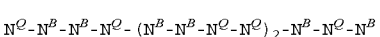

wherein each $N^Q$ is a non-bicyclic nucleoside; and each $N^B$ is a bicyclic nucleoside.

Provided herein are compounds comprising a modified oligonucleotide consisting of 8 to 19 linked nucleosides, wherein the nucleobase sequence of the modified oligonucleotide is complementary to miR-21 (SEQ ID NO: 1), and wherein the modified oligonucleotide comprises at least 8 contiguous nucleosides of the following nucleoside pattern VII in the 5' to 3' orientation:

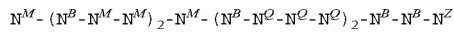

wherein each $N^M$ is a modified nucleoside that is not a bicyclic nucleoside; each $N^B$ is a bicyclic nucleoside; each $N^Q$ is a non-bicyclic nucleoside; and $N^Z$ is a modified nucleoside.

In certain embodiments of any of the compounds provided herein, the modified oligonucleotide comprises at least 9, at least 10, at least 11, at least 12, at least 13, at least 14, at least 15, at least 16, at least 17, at least 18, at least 19, at least 20, at least 21, or 22 contiguous nucleosides of nucleoside pattern III. In certain embodiments of any of the compounds provided herein, the modified oligonucleotide comprises at least 9, at least 10, at least 11, at least 12, at least 13, at least 14, at least 15, at least 16, at least 17, at least 18, or 19 contiguous nucleosides of nucleoside pattern IV, V, or VII. In certain embodiments of any of the compounds provided herein, the modified oligonucleotide comprises at least 9, at least 10, at least 11, at least 12, at least 13, at least 14, or 15 contiguous nucleosides of nucleoside pattern VI. In certain embodiments of any of the compounds provided herein, the modified oligonucleotide consists of 8, 9, 10, 11, 12, 13, 14, 15, 16, 17, 18, 19, 20, 21, or 22 linked nucleosides of nucleoside pattern III. In certain embodiments of any of the compounds provided herein, the modified oligonucleotide consists of 8, 9, 10, 11, 12, 13, 14, 15, 16, 17, 18, or 19 linked nucleosides of nucleoside pattern IV, V, or VII. In certain embodiments of any of the compounds provided herein, the modified oligonucleotide consists of 8, 9, 10, 11, 12, 13, 14, or 15 linked nucleosides of nucleoside pattern VI.

In certain embodiments of any of the compounds provided herein, the nucleobase sequence of the modified oligonucleotide is at least 90% complementary, is at least 95% complementary, or is 100% complementary to the nucleobase sequence of miR-21 (SEQ ID NO: 1).

In certain embodiments of any of the compounds provided herein, the nucleobase at position 1 of miR-21 is paired with the first nucleobase at the 3'-terminus of the modified oligonucleotide.

In certain embodiments of any of the compounds provided herein, each bicyclic nucleoside is independently selected from an LNA nucleoside, a cEt nucleoside, and an ENA nucleoside.

In certain embodiments of any of the compounds provided herein, each bicyclic nucleoside is a cEt nucleoside. In certain embodiments, the cEt nucleoside is an S-cEt nucleoside. In certain embodiments, the cEt nucleoside is an R-cEt nucleoside. In certain embodiments of any of the compounds provided herein, each bicyclic nucleoside is an LNA nucleoside.

In certain embodiments of any of the compounds provided herein, each bicyclic nucleoside comprises a non-methylated nucleobase.

In certain embodiments of any of the compounds provided herein, each non-bicyclic nucleoside is independently selected from a β-D-deoxyribonucleoside, a β-D-ribonucleoside, 2'-O-methyl nucleoside, a 2'-O-methoxyethyl nucleoside, and a 2'-fluoronucleoside. In certain embodiments of any of the compounds provided herein, each non-bicyclic nucleoside is independently selected from a β-D-deoxyribonucleoside, and a 2'-O-methoxyethyl nucleoside. In certain embodiments of any of the compounds provided herein, each non-bicyclic nucleoside is a β-D-deoxyribonucleoside. In certain embodiments of any of the compounds provided herein, each non-bicyclic nucleoside is a 2'-O-methoxyethyl nucleoside.

In certain embodiments of any of the compounds provided herein, at least two non-bicyclic nucleosides comprise sugar moieties that are different from one another. In certain embodiments of any of the compounds provided herein, each non-bicyclic nucleoside has the same type of sugar moiety.

In certain embodiments of any of the compounds provided herein, no more than two non-bicyclic nucleosides are 2'-O-methoxyethyl nucleosides. In certain such embodiments, each other non-bicyclic nucleoside is a β-D-deoxyribonucleoside.

In certain embodiments of any of the compounds provided herein, the 5'-most and the 3'-most non-bicyclic nucleosides are 2'-O-methoxyethyl nucleosides and each other non-bicyclic nucleoside is a β-D-deoxyribonucleoside. In certain embodiments of any of the compounds provided herein, two non-bicyclic nucleosides are 2'-MOE nucleosides and each other non-bicyclic nucleoside is a β-D-deoxyribonucleoside.

In certain embodiments of nucleoside pattern III, each nucleoside of R is a 2'-O-methoxyethyl nucleoside. In certain embodiments of nucleoside pattern III, three nucleosides of R are 2'-O-methoxyethyl nucleosides and one nucleoside of R is a β-D-deoxyribonucleoside.

In certain embodiments of nucleoside pattern III, each R is a 2'-O-methoxyethyl nucleoside; X is 1; each $N^B$ is an S-cEt nucleoside; each $N^Q$ is a β-D-deoxyribonucleoside; $N^Y$ is a β-D-deoxyribonucleoside; and $N^Z$ is a 2'-O-methoxyethyl nucleoside. In certain embodiments of nucleoside pattern III, each R is a 2'-O-methoxyethyl nucleoside; X is 1; each $N^B$ is an S-cEt nucleoside; each $N^Q$ is a β-D-deoxyribonucleoside; $N^Y$ is a β-D-deoxyribonucleoside; and $N^Z$ is an S-cEt nucleoside. In certain embodiments of nucleoside pattern III, each R is a 2'-O-methoxyethyl nucleoside; X is 1; each $N^B$ is an S-cEt nucleoside; each $N^Q$ is a β-D-deoxyribonucleoside; $N^Y$ is an S-cEt nucleoside; and $N^Z$ is an S-cEt nucleoside.

In certain embodiments of nucleoside pattern IV, $N^M$ is a 2'-O-methoxyethyl nucleoside; each $N^B$ is an S-cEt nucleoside; each $N^Q$ is a β-D-deoxyribonucleoside; $N^Y$ is a β-D-deoxyribonucleoside; $N^Z$ is a 2'-O-methoxyethyl nucleoside. In certain embodiments of nucleoside pattern IV, $N^M$ is a 2'-O-methoxyethyl nucleoside; each $N^B$ is an S-cEt nucleoside; each $N^Q$ is a β-D-deoxyribonucleoside; $N^Y$ is a β-D-deoxyribonucleoside; and $N^Z$ is an S-cEt nucleoside. In certain embodiments of nucleoside pattern IV, $N^M$ is a 2'-O-methoxyethyl nucleoside; each $N^B$ is an S-cEt nucleoside; each $N^Q$ is a β-D-deoxyribonucleoside; $N^Y$ is an S-cEt nucleoside; and $N^Z$ is an S-cEt nucleoside. In certain embodiments of nucleoside pattern IV, $N^M$ is a 2'-O-methoxyethyl nucleoside; each $N^B$ is an S-cEt nucleoside; each $N^Q$ is independently selected from a β-D-deoxyribonucleoside and a 2'-O-methoxyethyl nucleoside; $N^Y$ is a β-D-deoxyribonucleoside; and $N^Z$ is an S-cEt nucleoside. In certain embodiments of nucleoside pattern IV, the modified oligonucleotide has the structure:

(SEQ ID NO: 3)
$A_E C_S A_E T_E C_S A_E G_E T_E C_S TGAU_S AAGC_S TA_S$;

or (SEQ ID NO: 3)
$A_E C_S A_E T_E C_S A_E G_E T_E C_S TGAU_S AAGC_S U_S A_S$.

wherein nucleosides not followed by a subscript are β-D-deoxyribonucleosides; nucleosides followed by a subscript "E" are 2'-MOE nucleosides; and nucleosides followed by a subscript "S" are S-cEt nucleosides.

In certain embodiments of nucleoside pattern V, $N^M$ is a 2'-O-methoxyethyl nucleoside; each $N^B$ is an S-cEt nucleoside; each $N^Q$ is a β-D-deoxyribonucleoside; and $N^Z$ is a 2'-O-methoxyethyl nucleoside. In certain embodiments of nucleoside pattern V, the modified oligonucleotide has the structure:

(SEQ ID NO: 3)
$A_E C_S ATC_S A_S GTC_S U_S GAU_S A_S AGC_S U_S A_E$;

wherein nucleosides not followed by a subscript are β-D-deoxyribonucleosides; nucleosides followed by a subscript "E" are 2'-MOE nucleosides; and nucleosides followed by a subscript "S" are S-cEt nucleosides.

In certain embodiments of nucleoside pattern VI, each $N^Q$ is a modified nucleoside that is not a bicyclic nucleoside. In certain embodiments of nucleoside pattern VI, each $N^Q$ is, independently, selected from a 2'-O-methoxyethyl nucleoside and a β-D-deoxyribonucleoside. In certain embodiments of nucleoside pattern VI, each $N^Q$ is a 2'-O-methoxyethyl nucleoside. In certain embodiments of nucleoside pattern VI, each $N^Q$ is a β-D-deoxyribonucleoside. In certain embodiments of nucleoside pattern VI, each $N^Q$ is a 2'-O-methoxyethyl nucleoside; and each $N^B$ is an S-cEt nucleoside. In certain embodiments of nucleoside pattern VI, each $N^Q$ is a β-D-deoxyribonucleoside nucleoside; and each $N^B$ is an S-cEt nucleoside. In any of the embodiments of nucleoside pattern VI, the modified oligonucleotide may have 0, 1, or 2 mismatches with respect to the nucleobase sequence of miR-21. In certain such embodiments, the modified oligonucleotide has 0 mismatches with respect to the nucleobase sequence of miR-21. In certain embodiments, the modified oligonucleotide has 1 mismatch with respect to the nucleobase sequence of miR-21. In certain embodiments, the modified oligonucleotide has 2 mismatches with respect to the nucleobase sequence of miR-21. In certain embodiments of nucleoside pattern VI, the modified oligonucleotide has the structure:

(SEQ ID NO: 7)
$^{Me}C_E A_S A_S T_E C_S U_S A_E A_E U_S A_S A_E G_E C_S T_E A_S$;

wherein nucleosides followed by a subscript "E" are 2'-MOE nucleosides; nucleosides followed by a subscript "S" are S-cEt nucleosides; and $^{Me}C$ is 5-methyl cytosine.

In certain embodiments of nucleoside pattern VII, each $N^M$ is a 2'-O-methoxyethyl nucleoside; each $N^B$ is an S-cEt nucleoside; each $N^Q$ is independently selected from a 2'-O-methyl nucleoside and a β-D-deoxyribonucleoside; and $N^Z$ is independently selected from an S-cEt nucleoside and a 2'-O-methoxyethyl nucleoside. In certain embodiments of nucleoside pattern VII, each $N^M$ is a 2'-O-methoxyethyl nucleoside; each $N^B$ is an S-cEt nucleoside; each $N^Q$ is a β-D-deoxyribonucleoside; and $N^Z$ is an S-cEt nucleoside. In certain embodiments of nucleoside pattern VII, each $N^M$ is a 2'-O-methoxyethyl nucleoside; each $N^B$ is an S-cEt nucleoside; each $N^Q$ is independently selected from a 2'-O-methyl nucleoside and a β-D-deoxyribonucleoside; and $N^Z$ is an S-cEt nucleoside. In certain embodiments of nucleoside pattern VII, each $N^M$ is a 2'-O-methoxyethyl nucleoside; each $N^B$ is an S-cEt nucleoside; each $N^Q$ is independently selected from a 2'-O-methyl nucleoside and a β-D-deoxyribonucleoside; and $N^Z$ is 2'-O-methoxyethyl nucleoside. In certain embodiments of nucleoside pattern VII, the modified oligonucleotide has the structure:

(SEQ ID NO: 3)
$A_E C_S A_E T_E C_S A_E G_E T_E C_S TGAU_S AAGC_S U_S A_S$.

In certain embodiments, a compound comprises a modified oligonucleotide consisting of 8 to 22 linked nucleosides, wherein the modified oligonucleotide comprises at least 8, at least 9, at least 10, at least 11, at least 12, at least 13, at least 14, at least 15, at least 16, at least 17, at least 18, or at least 19 contiguous nucleosides of a structure selected from the structures in Table 1. In certain embodiments, a compound comprises a modified oligonucleotide having a structure selected from the structures in Table 1.

In certain embodiments of any of the compounds provided herein, at least one internucleoside linkage is a modified internucleoside linkage. In certain embodiments of any of the compounds provided herein, each internucleoside linkage is a modified internucleoside linkage. In certain embodiments, the modified internucleoside linkage is a phosphorothioate internucleoside linkage.

In certain embodiments of any of the compounds provided herein, at least one nucleoside comprises a modified nucleobase. In certain embodiments of any of the compounds provided herein, at least one cytosine is a 5-methyl cytosine. In certain embodiments of any of the compounds provided herein, each cytosine is a 5-methylcytosine. In certain embodiments of any of the compounds provided herein, the cytosine at position two of the modified oligonucleotide is a 5-methylcytosine.

In certain embodiments of any of the compounds provided herein, the modified oligonucleotide has the nucleobase sequence of a sequence selected from SEQ ID NOs: 3 to 10, wherein each T in the sequence is independently selected from T and U.

In certain embodiments of any of the compounds provided herein, the modified oligonucleotide has 0, 1, 2, or 3 mismatches with respect to the nucleobase sequence of miR-21. In certain embodiments of any of the compounds provided herein, the modified oligonucleotide has 0, 1, or 2 mismatches with respect to the nucleobase sequence of miR-21. In certain such embodiments, the modified oligonucleotide has 0 mismatches with respect to the nucleobase sequence of miR-21. In certain embodiments, the modified oligonucleotide has 1 mismatch with respect to the nucleobase sequence of miR-21. In certain embodiments, the modified oligonucleotide has 2 mismatches with respect to the nucleobase sequence of miR-21.

Provided herein are methods for inhibiting the activity of miR-21 comprising contacting a cell with a compound provided herein. In certain embodiments, the cell is in vivo. In certain embodiments, the cell is in vitro. In certain embodiments, the cell is a fibroblast cell, an epithelial cell, a stellate cell, a keratinocyte, or a fibrocyte. In certain embodiments, the cell is a hyperproliferative cell or a hypoxic cell. In certain embodiments, the fibroblast cell is a hyperproliferative fibroblast cell.

Provided herein are methods of inhibiting the activity of miR-21 comprising contacting a cell with any of the compounds described herein. In certain embodiments, the cell is in vivo. In certain embodiments, the cell is in vitro. In certain embodiments, the cell is a fibroblast cell, a hyperproliferative cell, a keratinocyte, or a hypoxic cell.

Provided herein are methods for decreasing collagen expression in a cell comprising contacting a cell with a compound provided herein.

Provided herein are methods to treat, prevent, or delay the onset of a disease associated with miR-21, comprising administering to a subject having such a disease any of the compounds provided herein.

In certain embodiments, the disease is fibrosis. In certain embodiments the fibrosis is kidney fibrosis, lung fibrosis, liver fibrosis, cardiac fibrosis, skin fibrosis, age-related fibrosis, spleen fibrosis, scleroderma, and/or post-transplant fibrosis.

In certain embodiments, the fibrosis is kidney fibrosis and is present in a subject having a disease or condition selected from glomerulosclerosis, tubulointerstitial fibrosis, IgA nephropathy, interstitial fibrosis/tubular atrophy; chronic kidney damage, chronic kidney disease, glomerular disease, glomerulonephritis, diabetes mellitus, idiopathy focal segmental glomerulosclerosis, membranous nephropathy, collapsing glomerulopathy, chronic recurrent kidney infection, chronic kidney disease following acute kidney injury (AKI), kidney damage following exposure to environmental toxin and/or natural product, and end stage renal disease. In certain embodiments, the kidney fibrosis results from acute or repetitive trauma to the kidney.

In certain embodiments, the fibrosis is liver fibrosis and is present in a subject having a disease selected from chronic liver injury, hepatitis infection (such as hepatitis B infection and/or hepatitis C infection), non-alcoholic steatohepatitis, alcoholic liver disease, liver damage following exposure to environmental toxin and/or natural product, and cirrhosis.

In certain embodiments, the pulmonary fibrosis is idiopathic pulmonary fibrosis, or the subject has chronic obstructive pulmonary disease.

In certain embodiments, disease is an inflammatory disease.

Provided herein are methods of promoting wound healing in a subject comprising administering to a subject having an acute or chronic wound any of the compounds provided herein. In certain embodiments, the chronic wound is an acute or chronic surgical wound, a penetrating wound, an avulsion injury, a crushing injury, a shearing injury, a burn injury, a laceration, a bite wound, an arterial ulcer, a venous ulcer, a pressure ulcer, or a diabetic ulcer. In certain embodiments, the compound is administered topically to the wound.

Provided herein are methods to treat a fibroproliferative disorder in a subject comprising administering to the subject any of the compounds provided herein.

Any of the methods provided herein may comprise selecting a subject having elevated miR-21 expression in one or more tissues.

In certain embodiments, administering any of the compounds provided herein to a subject reduces collagen expression.

In certain embodiments, a subject is in need of improved organ function, wherein the organ function is selected from cardiac function, pulmonary function, liver function, and kidney function. In certain embodiments, the administering of any of the compounds provided herein improves organ function in the subject, wherein the organ function is selected from cardiac function, pulmonary function, liver function, and kidney function.

Any of the methods provided herein comprises evaluating kidney function in a subject, which may include measuring blood urea nitrogen in the blood of the subject; measuring creatinine in the blood of the subject; measuring creatinine clearance in the subject; measuring proteinuria in the subject; measuring albumin:creatinine ratio in the subject; measuring urinary output in the subject; measuring inulin clearance in the urine of the subject; measuring urinary osmolarity in the subject; measuring urinary osmolality in the subject; measuring hematuria in the subject; measuring cystatin C in the blood and/or urine of the subject; and/or measuring neutrophil gelatinase-associated lipocalin (NGAL) in the blood or urine of the subject.

Any of the methods provided herein may comprise evaluating liver function in a subject, which may include measuring alanine aminotransferase levels in the blood of the subject; measuring aspartate aminotransferase levels in the blood of the subject; measuring bilirubin levels in the blood of the subject; measuring albumin levels in the blood of the subject; measuring prothrombin time in the subject; measuring ascites in the subject; measuring encephalopathy in the subject; and/or measuring liver stiffness, for example, using transient elastography.

Any of the methods provided herein may comprise evaluating lung function in a subject, which may include measuring vital capacity in the subject; measuring forced vital capacity in the subject; measuring forced expiratory volume in one second in the subject; measuring peak expiratory flow rate in the subject; measuring forced expiratory flow in the subject; measuring maximal voluntary ventilation in the subject; determining the ratio of forced expiratory volume in one second to forced vital capacity in the subject; measuring ventilation/perfusion ratio in the subject; measuring nitrogen washout in the subject; and/or measuring absolute volume of air in one or more lungs of a subject.

Any of the methods provided herein may comprise evaluating cardiac function in a subject, which may include measuring cardiac output in the subject; measuring stroke volume in the subject; measuring mean systolic ejection rate in the subject; measuring systolic blood pressure in the subject; measuring left ventricular ejection fraction in the subject; determining stroke index in the subject; determining cardiac index in the subject; measuring left ventricular percent fractional shortening in the subject; measuring mean velocity of circumferential fiber shortening in the subject; measuring left ventricular inflow velocity pattern in the subject; measuring pulmonary venous flow velocity pattern in the subject; and/or measuring peak early diastolic velocity of the mitral annulus of the subject.

Any of the methods provided herein may comprise administering to a subject at least one therapeutic agent selected from an anti-inflammatory agent, an immunosuppressive agent, an anti-diabetic agent, digoxin, a vasodilator, an angiotensin II converting enzyme (ACE) inhibitors, an angiotensin II receptor blockers (ARB), a calcium channel blocker, an isosorbide dinitrate, a hydralazine, a nitrate, a hydralazine, a beta-blocker, a natriuretic peptides, a heparinoid, a connective tissue growth factor inhibitor, and a transforming growth factor inhibitor. In certain embodiments, the anti-inflammatory agent is a non-steroidal anti-inflammatory agent, wherein the non-steroidal anti-inflammatory agent is optionally selected from ibuprofen, a COX-1 inhibitor and a COX-2 inhibitor. In certain embodiments, the immunosuppressive agent is selected from a corticosteroid, cyclophosphamide, and mycophenolate mofetil. In certain embodiments, anti-inflammatory agent is a corticosteroid, wherein the corticosteroid is optionally prednisone. In certain embodiments, the angiotensin II converting enzyme (ACE) inhibitors is selected from captopril, enalapril, lisinopril, benazepril, quinapril, fosinopril, and ramipril. In certain embodiments, the angiotensin II receptor blocker (ARB) is selected from candesartan, irbesartan, olmesartan, losartan, valsartan, telmisartan, and eprosartan.

In certain embodiments, a disease is cancer. In certain embodiments, the cancer is liver cancer, breast cancer, bladder cancer, prostate cancer, colon cancer, lung cancer, brain cancer, hematological cancer, pancreatic cancer, head and neck cancer, cancer of the tongue, stomach cancer, skin cancer, thyroid cancer, neuroblastoma, esophageal cancer, mesothelioma, neuroblastoma, bone cancer, kidney cancer, testicular cancer, rectal cancer, cervical cancer, or ovarian cancer. In certain embodiments, the liver cancer is hepatocellular carcinoma. In certain embodiments, the brain cancer is glioblastoma multiforme, oligoastrocytoma, or oligodendroglioma. In certain embodiments, the glioblastoma multiforme is proneural glioblastoma multiforme, neural glioblastoma multiforme, classical glioblastoma multiforme, or mesenchymal glioblastoma multiforme. In certain embodiments, the hematological cancer is acute myelogenous leukemia, acute lymphocytic leukemia, acute monocytic leukemia, multiple myeloma, chronic lymphotic leukemia, chronic myeloid leukemia, hodgkin's lymphoma, or non-hodgkin's lymphoma. In certain embodiments, the skin cancer is melanoma. In certain embodiments, the kidney cancer is renal cell carcinoma. In certain embodiments, the breast cancer is ductal cell carcinoma in situ, invasive ductal cell carcinoma, triple negative breast cancer, medullary carcinoma, tubular carcinoma, and mucinous carcinoma.

In certain embodiments, the methods provided herein comprise administering at least one additional anti-cancer therapy to the subject. In certain embodiments, the anti-cancer therapy is a DNA damaging agent, a proliferation inhibitor, an anti-folate, a growth factor receptor inhibitor, an anti-angiogenic agent, a receptor tyrosine kinase inhibitor, a kinase inhibitor, a growth factor inhibitor, a cytotoxic agent, radiation therapy, or surgical resection of a tumor. In certain embodiments, the DNA damaging agent is 1,3-bis(2-chloroethyl)-1-nitrosourea, busulfan, carboplatin, carmustine, chlorambucil, cisplatin, cyclophosphamide, dacarbazine, daunorubicin, doxorubicin, epirubicin, etoposide, idarubicin, ifosfamide, irinotecan, lomustine, mechlorethamine, melphalan, mitomycin C, mitoxantrone, oxaliplatin, temozolomide, or topotecan. In certain embodiments, the anti-folate is methotrexate, aminopterin, thymidylate synthase, serine hydroxymethyltransferase, folyilpolyglutamyl synthetase, g-glutamyl hydrolase, glycinamide-ribonucleotide transformylase, leucovorin, amino-imidazole-carboxamide-ribonucleotide transformylase, 5-fluorouracil, or a folate transporter. In certain embodiments, the growth factor receptor inhibitor is erlotinib, or gefitinib. In certain embodiments, the angiogenesis inhibitor is bevacizumab, thalidomide, carboxyamidotriazole, TNP-470, CM101, IFN-α, platelet factor-4, suramin, SU5416, thrombospondin, a VEGFR antagonist, cartilage-derived angiogenesis inhibitory factor, a matrix metalloproteinase inhibitor, angiostatin, endostatin, 2-methoxyestradiol, tecogalan, tetrathiomolybdate, prolactin, or linomide. In certain embodiments, the kinase inhibitor is bevacizumab, BIBW 2992, cetuximab, imatinib, trastuzumab, gefitinib, ranibizumab, pegaptanib, sorafenib, dasatinib, sunitinib, erlotinib, nilotinib, lapatinib, panitumumab, vandetanib, E7080, pazopanib, mubritinib, or fostamatinib.

In certain embodiments, the administering to a subject having cancer results in reduction of tumor size and/or tumor number. In certain embodiments, the administering to a subject having cancer prevents or delays an increase in tumor size and/or tumor number. In certain embodiments, the administering to a subject having cancer prevents or slows metastatic progression. In certain embodiments, the administering to a subject having cancer extends overall survival time and/or progression-free survival of the subject. In certain embodiments, the methods provided herein comprise selecting a subject having elevated serum alpha-fetoprotein and/or elevated serum des-gamma-carboxyprothrombin. In certain embodiments, the methods provided herein comprise reducing serum alpha-fetoprotein and/or serum des-gamma-carboxyprothrombin. In certain embodiments, the methods provided herein comprise selecting an animal having abnormal liver function.

In certain embodiments, a subject is a human. In certain embodiments, a subject is a canine.

In any of the methods provided herein, the compound is present as a pharmaceutical composition.

Any of the compounds provided herein may be for use in therapy. Any of the compounds provided herein may be for use in the treatment of fibrosis. Any of the compounds provided herein may be for use in promoting wound healing. Any of the compounds provided herein may be for use in treating cancer. Any of the compounds provided herein may be for use in preventing and/or delaying the onset of metastasis.

Any of the compounds provided herein may be for use in treating cardiac disease.

Any of the compounds provided herein may be for use in the preparation of a medicament. Any of the compounds provided herein may be for use in the preparation of a medicament for treating fibrosis. Any of the compounds provided herein may be for use in the preparation of a medicament for promoting wound healing. Any of the compounds provided herein may be for use in the preparation of a medicament for treating cancer. Any of the compounds provided herein may be for use in the preparation of a medicament for preventing and/or delaying the onset of metastasis.

DETAILED DESCRIPTION

Figure 1A:
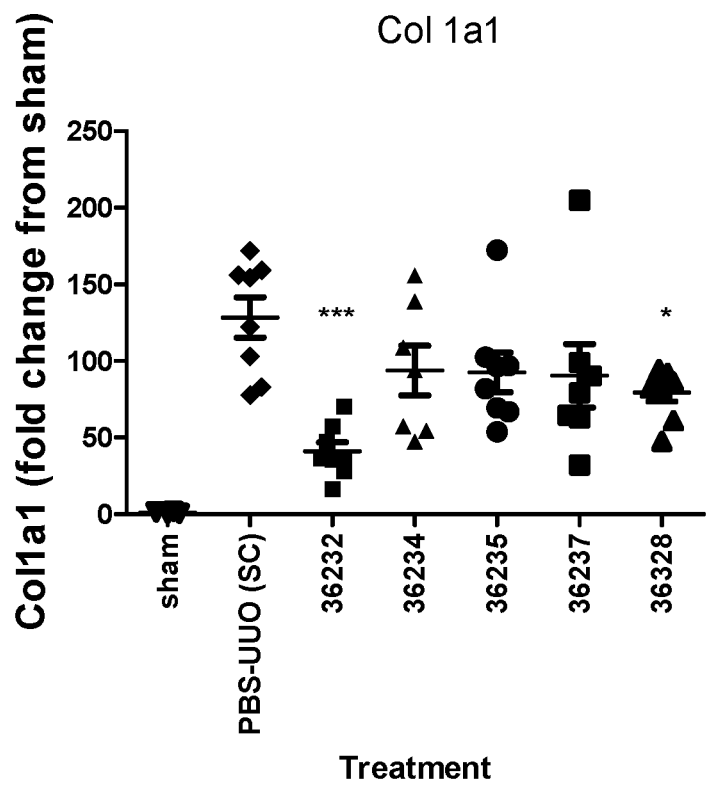
FIGS. 1A and 1B show the change in (A) collagen 1A1 and (B) collagen 3A1 expression in kidneys of UUO model mice administered certain anti-miR-21 compounds, as described in Example 1.

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well-known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can change, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

DEFINITIONS

"Fibrosis" means the formation or development of excess fibrous connective tissue in an organ or tissue. In certain embodiments, fibrosis occurs as a reparative or reactive process. In certain embodiments, fibrosis occurs in response to damage or injury. The term "fibrosis" is to be understood as the formation or development of excess fibrous connective tissue in an organ or tissue as a reparative or reactive process, as opposed to a formation of fibrous tissue as a normal constituent of an organ or tissue.

"Alport Syndrome" means an inherited form of kidney disease in which an abnormal level of glomerular basement membrane (GBM) is produced, leading to interstitial fibrosis, glomerular sclerosis and eventual loss of kidney function. The disease is also frequently characterized by hearing defects and ocular anomalies.

"Subject suspected of having" means a subject exhibiting one or more clinical indicators of a disease.

"Subject suspected of having fibrosis" means a subject exhibiting one or more clinical indicators of fibrosis.

"Fibroproliferative disorder" means a disorder characterized by excessive proliferation and/or activation of fibroblasts.

"Liver cancer" means a malignant tumor of the liver, either a primary cancer or metastasized cancer. In certain embodiments, liver cancer includes, but is not limited to, cancer arising from hepatocytes, such as, for example, hepatomas and hepatocellular carcinomas; fibrolamellar carcinoma; and cholangiocarcinomas (or bile duct cancer).

"Metastasis" means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

"Overall survival time" means the time period for which a subject survives after diagnosis of or treatment for a disease. In certain embodiments, the disease is cancer. In some embodiments, overall survival time is survival after diagnosis. In some embodiments, overall survival time is survival after the start of treatment.

"Progression-free survival" means the time period for which a subject having a disease survives, without the disease getting worse. In certain embodiments, progression-free survival is assessed by staging or scoring the disease. In certain embodiments, progression-free survival of a subject having liver cancer is assessed by evaluating tumor size, tumor number, and/or metastasis.

"Halts further progression" means to stop movement of a medical condition to an advanced state.

"Slows further progression" means to reduce the rate at which a medical condition moves towards an advanced state.

"Impaired kidney function" means reduced kidney function, relative to normal kidney function.

"Delay time to dialysis" means to maintain kidney function so that the need for dialysis treatment is delayed.

"Delay time to renal transplant" means to maintain kidney function so that the need for a kidney transplant is delayed.

"Improves kidney function" means to change kidney function toward normal limits. In certain embodiments, improved kidney function is measured by a reduction in blood urea nitrogen, a reduction in proteinuria, a reduction in albuminuria, etc.

"Improves life expectancy" means to lengthen the life of a subject by treating one or more symptoms of a disease in the subject.

"Hematuria" means the presence of red blood cells in the urine.

"Albuminuria" means the presence of excess albumin in the urine, and includes without limitation, normal albuminuria, high normal albuminuria, microalbuminuria and macroalbuminuria. Normally, the glomerular filtration permeability barrier, which is composed of podocyte, glomerular basement membrane and endothelial cells, prevents serum protein from leaking into urine. Albuminuria may reflect injury of glomerular permeability barrier. Albuminuria may be calculated from a 24-hour urine sample, an overnight urine sample or a spot-urine sample.

"High normal albuminuria" means elevated albuminuria characterized by (i) the excretion of 15 to <30 mg of albumin into the urine per 24 hours and/or (ii) an albumin/creatinine ratio of 1.25 to <2.5 mg/mmol (or 10 to <20 mg/g) in males or 1.75 to <3.5 mg/mmol (or 15 to <30 mg/g) in females.

"Microalbuminuria" means elevated albuminuria characterized by (i) the excretion of 30 to 300 mg of albumin into the urine per 24 hours and/or (ii) an albumin/creatinine ratio of 2.5 to <25 mg/mmol (or 20 to <200 mg/g) in males or 3.5 to <35 mg/mmol (or 30 to <300 mg/g) in females.

"Macroalbuminuria" means elevated albuminuria characterized by the excretion of more than 300 mg of albumin into the urine per 24 hours and/or (ii) an albumin/creatinine ratio of >25 mg/mmol (or >200 mg/g) in males or >35 mg/mmol (or >300 mg/g) in females.

"Albumin/creatinine ratio" means the ratio of urine albumin (mg/dL) per urine creatinine (g/dL) and is expressed as mg/g. Albumin/creatinine ratio may be calculated from a spot-urine sample and may be used as an estimate of albumin excretion over a 24 hour period.

"Estimated glomerular filtration rate (eGFR) or "Glomerular filtration rate (GFR)" means a measurement of how well the kidneys are filtering creatinine, and is used as an estimate of how much blood passes through the glomeruli per minute. Normal results may range from 90-120 mL/min/ 1.73 m2. Levels below 60 mL/min/1.73 m² for 3 or more months may be an indicator chronic kidney disease. Levels below 15 mL/min/1.73 m² may be an indicator of kidney failure.

"Proteinuria" means the presence of an excess of serum proteins. Proteinuria may be characterized by the excretion of >250 mg of protein into the urine per 24 hours and/or a urine protein to creatinine ratio of ≥0.20 mg/mg. Serum proteins elevated in association with proteinuria include, without limitation, albumin.

"Blood urea nitrogen" or "BUN" means a measure of the amount of nitrogen in the blood in the form of urea. The liver produces urea in the urea cycle as a waste product of the digestion of protein, and the urea is removed from the blood by the kidneys. Normal human adult blood may contain between 7 to 21 mg of urea nitrogen per 100 ml (7-21 mg/dL) of blood. Measurement of blood urea nitrogen is used as an indicator of renal health. If the kidneys are not able to remove urea from the blood normally, a subject's BUN rises.

"End stage renal disease (ESRD)" means the complete or almost complete failure of kidney function.

"Anti-miR" means an oligonucleotide having a nucleobase sequence complementary to a microRNA. In certain embodiments, an anti-miR is a modified oligonucleotide.

"Anti-miR-X" where "miR-X" designates a particular microRNA, means an oligonucleotide having a nucleobase sequence complementary to miR-X. In certain embodiments, an anti-miR-X is fully complementary to miR-X (i.e., 100% complementary). In certain embodiments, an anti-miR-X is at least 80%, at least 85%, at least 90%, or at least 95% complementary to miR-X. In certain embodiments, an anti-miR-X is a modified oligonucleotide.

"miR-21" means the mature miRNA having the nucleobase sequence UAGCUUAUCAGACUGAUGUUGA (SEQ ID NO: 1).

"miR-21 stem-loop sequence" means the stem-loop sequence having the nucleobase sequence UGUCGGGUAGCUUAUCAGACUGAUGUUGACU-GUUGAAUCUCAUGGCAACACCAGUCGAU GGGCU-GUCUGACA (SEQ ID NO: 2).

"Target nucleic acid" means a nucleic acid to which an oligomeric compound is designed to hybridize.

"Targeting" means the process of design and selection of nucleobase sequence that will hybridize to a target nucleic acid.

"Targeted to" means having a nucleobase sequence that will allow hybridization to a target nucleic acid.

"Target engagement" means the interaction of an oligonucleotide with the microRNA to which it is complementary, in a manner that changes the activity, expression or level of the microRNA. In certain embodiments, target engagement means an anti-miR interacting with the microRNA to which it is complementary, such that the activity of the microRNA is inhibited.

"Modulation" means a perturbation of function, amount, or activity. In certain embodiments, modulation means an increase in function, amount, or activity. In certain embodiments, modulation means a decrease in function, amount, or activity.

"Expression" means any functions and steps by which a gene's coded information is converted into structures present and operating in a cell.

"5' target site" means the nucleobase of a target nucleic acid which is complementary to the 3'-most nucleobase of a particular oligonucleotide.

"3' target site" means the nucleobase of a target nucleic acid which is complementary to the 5'-most nucleobase of a particular oligonucleotide.

"Region" means a portion of linked nucleosides within a nucleic acid. In certain embodiments, an oligonucleotide has a nucleobase sequence that is complementary to a region of a target nucleic acid. For example, in certain such embodiments an oligonucleotide is complementary to a region of a microRNA stem-loop sequence. In certain such embodiments, an oligonucleotide is fully complementary to a region of a microRNA stem-loop sequence.

"Segment" means a smaller or sub-portion of a region.

"Nucleobase sequence" means the order of contiguous nucleobases in an oligomeric compound or nucleic acid, typically listed in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that one nucleic acid is capable of hybridizing to another nucleic acid or oligonucleotide. In certain embodiments, complementary refers to an oligonucleotide capable of hybridizing to a target nucleic acid.

"Fully complementary" means each nucleobase of an oligonucleotide is capable of pairing with a nucleobase at each corresponding position in a target nucleic acid. In certain embodiments, an oligonucleotide is fully complementary to a microRNA, i.e. each nucleobase of the oligonucleotide is complementary to a nucleobase at a corresponding position in the microRNA. In certain embodiments, an oligonucleotide wherein each nucleobase has complementarity to a nucleobase within a region of a microRNA stem-loop sequence is fully complementary to the microRNA stem-loop sequence.

"Percent complementarity" means the percentage of nucleobases of an oligonucleotide that are complementary to an equal-length portion of a target nucleic acid. Percent complementarity is calculated by dividing the number of nucleobases of the oligonucleotide that are complementary to nucleobases at corresponding positions in the target nucleic acid by the total number of nucleobases in the oligonucleotide.

"Percent identity" means the number of nucleobases in a first nucleic acid that are identical to nucleobases at corresponding positions in a second nucleic acid, divided by the total number of nucleobases in the first nucleic acid. In certain embodiments, the first nucleic acid is a microRNA and the second nucleic acid is a microRNA. In certain embodiments, the first nucleic acid is an oligonucleotide and the second nucleic acid is an oligonucleotide.

"Hybridize" means the annealing of complementary nucleic acids that occurs through nucleobase complementarity.

"Mismatch" means a nucleobase of a first nucleic acid that is not capable of Watson-Crick pairing with a nucleobase at a corresponding position of a second nucleic acid.

"Identical" in the context of nucleobase sequences, means having the same nucleobase sequence, independent of sugar, linkage, and/or nucleobase modifications and independent of the methyl state of any pyrimidines present.

"MicroRNA" means an endogenous non-coding RNA between 18 and 25 nucleobases in length, which is the product of cleavage of a pre-microRNA by the enzyme Dicer. Examples of mature microRNAs are found in the microRNA database known as miRBase (http://microrna.sanger.ac.uk/). In certain embodiments, microRNA is abbreviated as "microRNA" or "miR."

"Pre-microRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature microRNA sequence. Pre-microRNA sequences and stem-loop sequences may overlap. Examples of stem-loop sequences are found in the microRNA database known as miRBase (http://microrna.sanger.ac.uk/).

"Pri-microRNA" or "pri-miR" means a non-coding RNA having a hairpin structure that is a substrate for the double-stranded RNA-specific ribonuclease Drosha.

"microRNA precursor" means a transcript that originates from a genomic DNA and that comprises a non-coding, structured RNA comprising one or more microRNA sequences. For example, in certain embodiments a microRNA precursor is a pre-microRNA. In certain embodiments, a microRNA precursor is a pri-microRNA.

"microRNA-regulated transcript" means a transcript that is regulated by a microRNA.

"Monocistronic transcript" means a microRNA precursor containing a single microRNA sequence.

"Polycistronic transcript" means a microRNA precursor containing two or more microRNA sequences.

"Seed sequence" means a nucleobase sequence comprising from 6 to 8 contiguous nucleobases of nucleobases 1 to 9 of the 5'-end of a mature microRNA sequence.

"Seed match sequence" means a nucleobase sequence that is complementary to a seed sequence, and is the same length as the seed sequence.

"Oligomeric compound" means a compound that comprises a plurality of linked monomeric subunits. Oligomeric compounds included oligonucleotides.

"Oligonucleotide" means a compound comprising a plurality of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside.

"Compound comprising a modified oligonucleotide consisting of" a number of linked nucleosides means a compound that includes a modified oligonucleotide having the specified number of linked nucleosides. Thus, the compound may include additional substituents or conjugates. Unless otherwise indicated, the compound does not include any additional nucleosides beyond those of the modified oligonucleotide.

"Modified oligonucleotide" means an oligonucleotide having one or more modifications relative to a naturally occurring terminus, sugar, nucleobase, and/or internucleoside linkage. A modified oligonucleotide may comprise unmodified nucleosides.

"Single-stranded modified oligonucleotide" means a modified oligonucleotide which is not hybridized to a complementary strand.

"Modified nucleoside" means a nucleoside having any change from a naturally occurring nucleoside. A modified nucleoside may have a modified sugar, and an unmodified nucleobase. A modified nucleoside may have a modified sugar and a modified nucleobase. A modified nucleoside may have a natural sugar and a modified nucleobase. In certain embodiments, a modified nucleoside is a bicyclic nucleoside. In certain embodiments, a modified nucleoside is a non-bicyclic nucleoside.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar moiety" means substitution and/or any change from a natural sugar.

"Unmodified nucleobase" means the naturally occurring heterocyclic bases of RNA or DNA: the purine bases adenine (A) and guanine (G), and the pyrimidine bases thymine (T), cytosine (C) (including 5-methylcytosine), and uracil (U).

"5-methylcytosine" means a cytosine comprising a methyl group attached to the 5 position.

"Non-methylated cytosine" means a cytosine that does not have a methyl group attached to the 5 position.

"Modified nucleobase" means any nucleobase that is not an unmodified nucleobase.

"Furanosyl" means a structure comprising a 5-membered ring consisting of four carbon atoms and one oxygen atom.

"Naturally occurring furanosyl" means a ribofuranosyl as found in naturally occurring RNA or a deoxyribofuranosyl as found in naturally occurring DNA.

"Sugar moiety" means a naturally occurring furanosyl or a modified sugar moiety.

"Modified sugar moiety" means a substituted sugar moiety or a sugar surrogate.

"Substituted sugar moiety" means a furanosyl that is not a naturally occurring furanosyl. Substituted sugar moieties include, but are not limited to sugar moieties comprising modifications at the 2'-position, the 5'-position and/or the 4'-position of a naturally occurring furanosyl. Certain substituted sugar moieties are bicyclic sugar moieties.

"Sugar surrogate" means a structure that does not comprise a furanosyl and that is capable of replacing the naturally occurring furanosyl of a nucleoside, such that the resulting nucleoside is capable of (1) incorporation into an oligonucleotide and (2) hybridization to a complementary nucleoside. Such structures include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid).

Sugar surrogates include without limitation morpholinos, cyclohexenyls and cyclohexitols.

"2'-O-methyl sugar" or "2'-OMe sugar" means a sugar having a O-methyl modification at the 2' position.

"2'-O-methoxyethyl sugar" or "2'-MOE sugar" means a sugar having a 0-methoxyethyl modification at the 2' position.

"2'-O-fluoro" or "2'-F" means a sugar having a fluoro modification of the 2' position.

"Bicyclic sugar moiety" means a modified sugar moiety comprising a 4 to 7 membered ring (including by not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl. Nonlimiting exemplary bicyclic sugar moieties include LNA, ENA, cEt, S-cEt, and R-cEt.

"Locked nucleic acid (LNA) sugar moiety" means a substituted sugar moiety comprising a $(CH_2)$—O bridge between the 4' and 2' furanose ring atoms.

"ENA sugar moiety" means a substituted sugar moiety comprising a $(CH_2)_2$—O bridge between the 4' and 2' furanose ring atoms.

"Constrained ethyl (cEt) sugar moiety" means a substituted sugar moiety comprising a $CH(CH_3)$—O bridge between the 4' and the 2' furanose ring atoms. In certain embodiments, the $CH(CH_3)$—O bridge is constrained in the S orientation. In certain embodiments, the $CH(CH_3)$—O is constrained in the R orientation.

"S-cEt sugar moiety" means a substituted sugar moiety comprising an S-constrained $CH(CH_3)$—O bridge between the 4' and the 2' furanose ring atoms.

"R-cEt sugar moiety" means a substituted sugar moiety comprising an R-constrained $CH(CH_3)$—O bridge between the 4' and the 2' furanose ring atoms.

"2'-O-methyl nucleoside" means a 2'-modified nucleoside having a 2'-O-methyl sugar modification.

"2'-O-methoxyethyl nucleoside" means a 2'-modified nucleoside having a 2'-O-methoxyethyl sugar modification. A 2'-O-methoxyethyl nucleoside may comprise a modified or unmodified nucleobase.

"2'-fluoro nucleoside" means a 2'-modified nucleoside having a 2'-fluoro sugar modification. A 2'-fluoro nucleoside may comprise a modified or unmodified nucleobase.

"Bicyclic nucleoside" means a 2'-modified nucleoside having a bicyclic sugar moiety. A bicyclic nucleoside may have a modified or unmodified nucleobase.

"cEt nucleoside" means a nucleoside comprising a cEt sugar moiety. A cEt nucleoside may comprise a modified or unmodified nucleobase.

"S-cEt nucleoside" means a nucleoside comprising an S-cEt sugar moiety.

"R-cEt nucleoside" means a nucleoside comprising an R-cEt sugar moiety.

"Non-bicyclic nucleoside" means a nucleoside that has a sugar other than a bicyclic sugar. In certain embodiments, a non-bicyclic nucleoside comprises a naturally occurring sugar. In certain embodiments, a non-bicyclic nucleoside comprises a modified sugar. In certain embodiments, a non-bicyclic nucleoside is a β-D-deoxyribonucleoside. In certain embodiments, a non-bicyclic nucleoside is a 2'-O-methoxyethyl nucleoside.

"β-D-deoxyribonucleoside" means a naturally occurring DNA nucleoside. "β-D-ribonucleoside" means a naturally occurring RNA nucleoside. "LNA nucleoside" means a nucleoside comprising a LNA sugar moiety.

"ENA nucleoside" means a nucleoside comprising an ENA sugar moiety.

"Motif" means a pattern of modified and/or unmodified nucleobases, sugars, and/or internucleoside linkages in an oligonucleotide. In certain embodiments, a motif is a nucleoside pattern.

"Nucleoside pattern" means a pattern of nucleoside modifications in a modified oligonucleotide or a region thereof. A nucleoside pattern is a motif that describes the arrangement of nucleoside modifications in an oligonucleotide.

"Fully modified oligonucleotide" means each nucleobase, each sugar, and/or each internucleoside linkage is modified.

"Uniformly modified oligonucleotide" means each nucleobase, each sugar, and/or each internucleoside linkage has the same modification throughout the modified oligonucleotide.

"Stabilizing modification" means a modification to a nucleoside that provides enhanced stability to a modified oligonucleotide, in the presence of nucleases, relative to that provided by 2'-deoxynucleosides linked by phosphodiester internucleoside linkages. For example, in certain embodiments, a stabilizing modification is a stabilizing nucleoside modification. In certain embodiments, a stabilizing modification is an internucleoside linkage modification.

"Stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

"Stabilizing internucleoside linkage" means an internucleoside linkage that provides improved nuclease stability to an oligonucleotide relative to that provided by a phosphodiester internucleoside linkage. In one embodiment, a stabilizing internucleoside linkage is a phosphorothioate internucleoside linkage.

"Subject" means a human or non-human animal selected for treatment or therapy. In certain embodiments, a non-human animal subject is a canine.

"Subject in need thereof" means a subject that is identified as in need of a therapy or treatment.

"Subject suspected of having" means a subject exhibiting one or more clinical indicators of a disease.

"Administering" means providing a pharmaceutical agent or composition to a subject, and includes, but is not limited to, administering by a medical professional and self-administering.

"Parenteral administration" means administration through injection or infusion. Parenteral administration includes, but is not limited to, subcutaneous administration, intravenous administration, and intramuscular administration.

"Subcutaneous administration" means administration just below the skin.

"Intravenous administration" means administration into a vein.

"Intracardial administration" means administration into the heart. In certain embodiments, intracardial administration occurs by way of a catheter. In certain embodiments, intracardial administration occurs by way of open heart surgery.

"Pulmonary administration" means administration to the lungs.

"Administered concomitantly" refers to the co-administration of two or more agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, radiation therapy, or administration of a pharmaceutical agent.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"At risk for developing" means the state in which a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

"Prevent the onset of" means to prevent the development of a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual. In certain embodiments, a dose is administered as a slow infusion.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Improved organ function" means a change in organ function toward normal limits. In certain embodiments, organ function is assessed by measuring molecules found in a subject's blood or urine. For example, in certain embodiments, improved liver function is measured by a reduction in blood liver transaminase levels. In certain embodiments, improved kidney function is measured by a reduction in blood urea nitrogen, a reduction in proteinuria, a reduction in albuminuria, etc.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Subject compliance" means adherence to a recommended or prescribed therapy by a subject.

"Comply" means the adherence with a recommended therapy by a subject.

"Recommended therapy" means a treatment recommended by a medical professional to treat, ameliorate, delay, or prevent a disease.

Overview miR-21 is a ubiquitously expressed microRNA that is linked to a variety of cellular processes, including cell differentiation, proliferation, apoptosis and matrix turnover. Additionally, miR-21 is associated with multiple diseases. miR-21 is frequently upregulated in cancer, and inhibition of miR-21 has demonstrated a reduction in tumor growth in several animal models of cancer Inhibition of miR-21 in an animal model of cardiac hypertrophy demonstrated a role for miR-21 in heart disease. A role in fibrosis has been demonstrated in animal models of cardiac fibrosis, kidney fibrosis, and lung fibrosis. A study of the inhibition of miR-21 in a tissue explants model illustrated that the inhibition of miR-21 promotes wound healing. As such, inhibitors of miR-21 are useful in a variety of research and clinical settings.

To identify potent inhibitors of miR-21, a large number of anti-miR-21 compounds were designed and synthesized. The compounds varied in length, and in the number, placement, and identity of bicyclic nucleosides and non-bicyclic nucleosides. An initial series of compounds was tested in an in vitro luciferase assay, which identified a subset of compounds as in vitro active compounds. These in vitro active compounds were then tested in in vivo assays to identify those compounds that are potent inhibitors of miR-21 in vivo. From the initial in vitro and in vivo screens, certain compounds were selected as the basis for the design of additional compounds. The experimentally observed correlations between structure and activity (both in vitro and in vivo) were used to inform the design of these additional compounds, with further variations in length and selection and arrangement of bicyclic and non-bicyclic nucleosides. The in vitro and in vivo screening assays were repeated for these additional compounds. Certain compounds were also tested for other properties, for example, susceptibility to exonuclease activity and viscosity in solution. It was observed that the most active in vitro compounds were not necessarily the most active in vivo compounds, and further that some moderately active in vitro compounds were highly active in vivo compounds.

Of nearly 300 compounds screened in vitro during this process, no more 145 were identified as active in the in vitro luciferase assay. Of these active in vitro compounds, a subset was identified as active in vivo. Through this iterative process of designing and screening compounds, it was observed that compounds having particular patterns of bicyclic and non-bicyclic modifications were potent inhibitors of miR-21 in vivo. As such, these compounds are useful for the modulation of cellular processes that are promoted by the activity of miR-21. Further, such compounds are useful for treating, preventing, and/or delaying the onset of diseases associated with miR-21. Such diseases may be characterized by abnormally high expression of miR-21, relative to non-disease samples. Such diseases include, but are not limited to, fibrosis, acute kidney injury, cardiac hypertrophy, myocardial infarction, and cancer. Additionally, the compositions and methods provided herein may be used to promote wound healing.

Certain Modified Oligonucleotides Targeted to miR-21

Provided herein are modified oligonucleotides having certain patterns of bicyclic and non-bicyclic nucleosides. Modified oligonucleotides having the patterns identified herein are effective inhibitors of miR-21 activity.

Each of the nucleoside patterns illustrated herein is shown in the 5' to 3' orientation.

In certain embodiments, provided herein are compounds comprising a modified oligonucleotide consisting of 8 to 22 linked nucleosides, wherein the nucleobase sequence of the modified oligonucleotide is complementary to miR-21 (SEQ ID NO: 1) and wherein the modified oligonucleotide comprises at least 8 contiguous nucleosides of the following nucleoside pattern III in the 5' to 3' orientation:

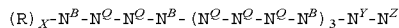

wherein each R is a non-bicyclic nucleoside; X is from 1 to 4;
each $N^B$ is a bicyclic nucleoside;
each $N^Q$ is a non-bicyclic nucleoside;
$N^Y$ is a modified nucleoside or an unmodified nucleoside; and
each $N^Z$ is a modified nucleoside.

In certain embodiments of nucleoside pattern III, X is 1. In certain embodiments of nucleoside pattern III, X is 2. In certain embodiments of nucleoside pattern III, X is 3. In certain embodiments of nucleoside pattern III, X is 4.

In certain embodiments, provided herein are compounds comprising a modified oligonucleotide consisting of 8 to 19 linked nucleosides, wherein the nucleobase sequence of the modified oligonucleotide is complementary to miR-21 (SEQ ID NO: 1) and wherein the modified oligonucleotide comprises at least 8 contiguous nucleosides of the following nucleoside pattern IV in the 5' to 3' orientation:

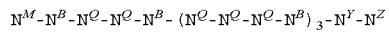

wherein $N^M$ is a modified nucleoside that is not a bicyclic nucleoside;
each $N^B$ is a bicyclic nucleoside;
each $N^Q$ is a non-bicyclic nucleoside;
$N^Y$ is a modified nucleoside or an unmodified nucleoside; and
$N^Z$ is a modified nucleoside.

In certain embodiments, provided herein are compounds comprising a modified oligonucleotide consisting of 8 to 19 linked nucleosides, wherein the nucleobase sequence of the modified oligonucleotide is complementary to miR-21 (SEQ ID NO: 1) and wherein the modified oligonucleotide comprises at least 8 contiguous nucleosides of the following nucleoside pattern V in the 5' to 3' orientation:

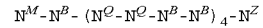

wherein $N^M$ is a modified nucleoside that is not a bicyclic nucleoside;
each $N^B$ is a bicyclic nucleoside;
each $N^Q$ is a non-bicyclic nucleoside; and
$N^Z$ is a modified nucleoside.

In certain embodiments, provided herein are compounds comprising a modified oligonucleotide consisting of 8 to 15 linked nucleosides, wherein the nucleobase sequence of the modified oligonucleotide is complementary to miR-21 (SEQ ID NO: 1), and wherein the modified oligonucleotide comprises at least 8 contiguous nucleosides of the following nucleoside pattern VI in the 5' to 3' orientation:

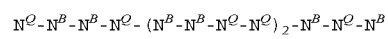

wherein each $N^Q$ is a non-bicyclic nucleoside; and
each $N^B$ is a bicyclic nucleoside.

In certain embodiments, provided herein are compounds comprising a modified oligonucleotide consisting of 8 to 19 linked nucleosides, wherein the nucleobase sequence of the modified oligonucleotide is complementary to miR-21 (SEQ ID NO: 1) and wherein the modified oligonucleotide comprises at least 8 contiguous nucleosides of the following nucleoside pattern VII in the 5' to 3' orientation:

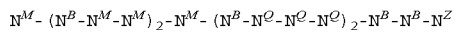

wherein each $N^M$ is a modified nucleoside that is not a bicyclic nucleoside;
each $N^B$ is a bicyclic nucleoside;
each $N^Q$ is a non-bicyclic nucleoside; and
$N^Z$ is a modified nucleoside.

The following embodiments apply to any of the nucleoside patterns described herein, including nucleoside patterns III to VII.

In certain embodiments, the modified oligonucleotide comprises at least 9, at least 10, at least 11, at least 12, at least 13, at least 14, at least 15, at least 16, at least 17, at least 18, at least 19, at least 20, at least 21, or 22 contiguous nucleosides of a nucleoside pattern described herein.

In certain embodiments of any of the nucleoside patterns described herein, the nucleobase sequence of the modified oligonucleotide is at least 90% complementary to miR-21 (SEQ ID NO: 1). In certain embodiments of any of the nucleoside patterns described herein, the nucleobase sequence of the modified oligonucleotide is at least 95% complementary to miR-21 (SEQ ID NO: 1). In certain embodiments of any of the nucleoside patterns described herein, the nucleobase sequence of the modified oligonucleotide is 100% complementary to miR-21 (SEQ ID NO: 1).

In certain embodiments of any of the nucleoside patterns described herein, the nucleobase sequence of the modified oligonucleotide is complementary to miR-21 such that position 1 of the microRNA is paired with the 3'-terminal nucleobase of the oligonucleotide. For example:

```
5'-UAGCUUAUCAGACUGAUGUUGA-3'   (miR-21; SEQ ID NO: 1)
   |||||||||||||||||||||
3'-ATCGAATAGTCTGACTACA-5'      (an anti-miR-21; SEQ ID NO: 3);

5'-UAGCUUAUCAGACUGAUGUUGA-3'   (miR-21; SEQ ID NO: 1)
   ||||||||||||||||||||||
3'-ATCGAATAGTCTGACTACAACT-5'   (an anti-miR-21; SEQ ID NO: 4);

5'-UAGCUUAUCAGACUGAUGUUGA-3'   (miR-21; SEQ ID NO: 1)
   ||||||||||||||
3'-ATCGAATAGTCTGAC-5'          (an anti-miR-21; SEQ ID NO: 5);

5'-UAGCUUAUCAGACUGAUGUUGA-3'   (miR-21; SEQ ID NO: 1)
   ||||||||||||||||
3'-ATCGAATAGTCTGACT-5'         (an anti-miR-21; SEQ ID NO: 6);

5'-UAGCUUAUCAGACUGAUGUUGA-3'   (miR-21; SEQ ID NO: 1)
   ||||||||||||||||||
3'-ATCGAATAGTCTGACTAC-5'       (an anti-miR-21; SEQ ID NO: 9);
```

In certain embodiments of any of the nucleoside patterns described herein, the nucleobase sequence of the modified oligonucleotide is complementary to miR-21 such that position 2 of the microRNA is paired with the 3'-terminal nucleobase of the oligonucleotide. For example:

```
5'-UAGCUUAUCAGACUGAUGUUGA-3'   (miR-21; SEQ ID NO: 1)
   ||||||||||||||||||
3'-TCGAATAGTCTGACTACA-5'       (an anti-miR-21; SEQ ID NO: 10);
```

In certain embodiments of any of the nucleoside patterns described herein the nucleobase sequence of the modified oligonucleotide is complementary to miR-21, and has 1 to 3 mismatches with respect to the nucleobase sequence of miR-21. In certain embodiments, the modified oligonucleotide is complementary to miR-21, and has 1 mismatch with respect to the nucleobase sequence of miR-21. the modified oligonucleotide is complementary to miR-21, and has 2 mismatches with respect to the nucleobase sequence of miR-21. In certain embodiments, the modified oligonucleotide has the sequence of any one of SEQ ID NOs: 3 to 6, 9, and 10, but with 1 or 2 nucleobase changes. For example:

```
5'-UAGCUUAUCAGACUGAUGUUGA-3'   (miR-21; SEQ ID NO: 1)
   |||||||| ||| ||
3'-ATCGAATAATCTAAC-5'          (an anti-miR-21; SEQ ID NO: 7);

5'-UAGCUUAUCAGACUGAUGUUGA-3'   (miR-21; SEQ ID NO: 1)
   |||||||||||||||||
3'-TTCGAATAGTCTGACTACA-5'      (an anti-miR-21; SEQ ID NO: 8);
```

It is to be understood that, in SEQ ID NOs: 3 to 10, each "T" in the sequence may independently be either a "T" nucleobase or a "U" nucleobase, and that a compound having the sequence of any or SEQ ID NOs: 3 to 10 may comprise all T's, all U's, or any combination of U's and T's. Thus, the presence of "T" at various positions in SEQ ID NOs: 3 to 10 throughout the present disclosure and in the accompanying sequence listing is not limiting with respect to whether that particular nucleobase is a "T" or a "U."

In certain embodiments of any of the nucleoside patterns described herein, each bicyclic nucleoside is independently selected from an LNA nucleoside, a cEt nucleoside, and an ENA nucleoside. In certain embodiments, the sugar moieties of at least two bicyclic nucleosides are different from one another. In certain embodiments, all bicyclic nucleosides have the same sugar moieties as one another. In certain embodiments, each bicyclic nucleoside is a cEt nucleoside. In certain embodiments, each bicyclic nucleoside is an LNA nucleoside.

In certain embodiments of any of the nucleoside patterns described herein, a cEt nucleoside is an S-cEt nucleoside. In certain embodiments of any of the nucleoside patterns described herein, a cEt nucleoside is an R-cEt nucleoside.

In certain embodiments of any of the nucleoside patterns described herein, each non-bicyclic nucleoside is independently selected from a β-D-deoxyribonucleoside, a β-D-ribonucleoside, a 2'-O-methyl nucleoside, a 2'-O-methoxyethyl nucleoside, and a 2'-fluoronucleoside.

In certain embodiments of any of the nucleoside patterns described herein, each non-bicyclic nucleoside is independently selected from a β-D-deoxyribonucleoside, and a 2'-O-methoxyethyl nucleoside.

In certain embodiments of any of the nucleoside patterns described herein, at least two non-bicyclic nucleosides comprise sugar moieties that are different from one another and are independently selected from a β-D-deoxyribonucleoside, a β-D-ribonucleoside, a 2'-O-methyl nucleoside, a 2'-O-methoxyethyl nucleoside, and a 2'-fluoronucleoside.

In certain embodiments of any of the nucleoside patterns described herein, at least two non-bicyclic nucleosides comprise sugar moieties that are different from one another and are independently selected from a β-D-deoxyribonucleoside and a 2'-O-methoxyethyl nucleoside.

In certain embodiments of any of the nucleoside patterns described herein, each non-bicyclic nucleoside is independently selected from a β-D-deoxyribonucleoside, a 2'-O-methyl nucleoside, and a 2'-O-methoxyethyl nucleoside.

In certain embodiments of any of the nucleoside patterns described herein, each non-bicyclic nucleoside has the same type of sugar moiety and is selected from a β-D-deoxyribonucleoside, a β-D-ribonucleoside, a 2'-O-methyl nucleoside, a 2'-O-methoxyethyl nucleoside, and a 2'-fluoronucleoside.

In certain embodiments of any of the nucleoside patterns described herein, each non-bicyclic nucleoside is a β-D-deoxyribonucleoside. In certain embodiments, each non-bicyclic nucleoside is a 2'-O-methyl nucleoside.

In certain embodiments of any of the nucleoside patterns described herein, no more than 3 of the non-bicyclic nucleosides are 2'-O-methoxyethyl nucleosides. In certain embodiments, no more than 2 of the non-bicyclic nucleosides are 2'-O-methoxyethyl nucleosides. In certain embodiments, no more than 1 of the non-bicyclic nucleosides is a 2'-O-methoxyethyl nucleoside.

In certain embodiments of any of the nucleoside patterns described herein, one non-bicyclic nucleoside is a 2'-MOE nucleoside and each other non-bicyclic nucleosides is a β-D-deoxyribonucleoside. In certain embodiments, two non-bicyclic nucleosides are 2'-O-methoxyethyl nucleosides and each other non-bicyclic nucleoside is a β-D-deoxyribonucleoside. In certain embodiments, three non-bicyclic nucleosides are 2'-O-methoxyethyl nucleosides and each other non-bicyclic nucleoside is a β-D-deoxyribonucleoside.

In certain embodiments of any of the nucleoside patterns described herein, the 5'-most non-bicyclic nucleoside and the 3'-most non-bicyclic nucleoside are 2'-O-methoxyethyl nucleosides, and each other non-bicyclic nucleoside is a β-D-deoxyribonucleoside.

In certain embodiments of nucleoside pattern III, R is a modified nucleoside that is not a bicyclic nucleoside; and x is 1. In certain embodiments of nucleoside pattern III, R is a modified nucleoside that is not a bicyclic nucleoside; x is 1; and each $N^Q$ is an unmodified nucleoside. In certain embodiments of nucleoside pattern III, R is a modified nucleoside that is not a bicyclic nucleoside; x is 1; each $N^Q$ is an unmodified nucleoside; each $N^B$ is independently selected from an S-cEt nucleoside and an LNA nucleoside; and $N^Y$ is selected from a β-D-deoxyribonucleoside, a 2'-O-methoxyethyl nucleoside, an S-cEt nucleoside, and an LNA nucleoside. In certain embodiments of nucleoside pattern III, R is a modified nucleoside that is not a bicyclic nucleoside; x is 1; and each $N^Q$ is a β-D-deoxyribonucleoside. In certain embodiments of nucleoside pattern III, R is a modified nucleoside that is not a bicyclic nucleoside; x is 1; each $N^Q$ is a β-D-deoxyribonucleoside; each $N^B$ is independently selected from an S-cEt nucleoside and an LNA nucleoside; and $N^Y$ is selected from a β-D-deoxyribonucleoside, a 2'-O-methoxyethyl nucleoside, an S-cEt nucleoside, and an LNA nucleoside. In certain embodiments of nucleoside pattern III, R is a modified nucleoside that is not a bicyclic nucleoside; x is 1; each $N^Q$ is an unmodified nucleoside; each $N^B$ is an S-cEt nucleoside; and $N^Y$ is selected from a β-D-deoxyribonucleoside, a 2'-O-methoxyethyl nucleoside, and an S-cEt nucleoside. In certain embodiments of nucleoside pattern III, R is a modified nucleoside that is not a bicyclic nucleoside; x is 1; each $N^Q$ is a β-D-deoxyribonucleoside; each $N^B$ is an S-cEt nucleoside; and $N^Y$ is selected from a β-D-deoxyribonucleoside, a 2'-O-methoxyethyl nucleoside, and an S-cEt nucleoside. In certain embodiments, the modified oligonucleotide of pattern III has a nucleobase sequence selected from SEQ ID NOs: 3 to 10, wherein each T in the sequence is independently selected from T and U.

In certain embodiments of nucleoside pattern IV, $N^M$ is a 2'-O-methoxyethyl nucleoside; each $N^B$ is independently selected from an S-cEt nucleoside and an LNA nucleoside; each $N^Q$ is independently selected from a β-D-deoxyribonucleoside and a 2'-O-methoxyethyl nucleoside; $N^Y$ is selected from a 2'-O-methoxyethyl nucleoside, an S-cEt nucleoside, an LNA nucleoside, and a β-D-deoxyribonucleoside; and $N^Z$ is selected from a 2'-O-methoxyethyl nucleoside, an LNA nucleoside, and an S-cEt nucleoside. In certain embodiments of nucleoside pattern IV, $N^M$ is a 2'-O-methoxyethyl nucleoside; each $N^B$ is an S-cEt nucleoside; each $N^Q$ is independently selected from a β-D-deoxyribonucleoside and a 2'-O-methoxyethyl nucleoside; $N^Y$ is selected from a 2'-O-methoxyethyl nucleoside, an S-cEt nucleoside, and a β-D-deoxyribonucleoside; and $N^Z$ is selected from a 2'-O-methoxyethyl nucleoside and an S-cEt nucleoside. In certain embodiments of nucleoside pattern IV, $N^M$ is a 2'-O-methoxyethyl nucleoside; each $N^B$ is an S-cEt nucleoside; each $N^Q$ is a β-D-deoxyribonucleoside; $N^Y$ is an S-cEt nucleoside; and $N^Z$ is an S-cEt nucleoside. In certain embodiments, the modified oligonucleotide of pattern IV has a nucleobase sequence selected from SEQ ID NOs: 3 to 10, wherein each T in the sequence is independently selected from T and U.

In certain embodiments of nucleoside pattern V, $N^M$ is a 2'-O-methoxyethyl nucleoside; each $N^B$ is independently selected from an S-cEt nucleoside and an LNA nucleoside; each $N^Q$ is independently selected from a β-D-deoxyribonucleoside and a 2'-O-methoxyethyl nucleoside; and $N^Z$ is selected from a 2'-O-methoxyethyl nucleoside, an LNA nucleoside, and an S-cEt nucleoside. In certain embodiments of nucleoside pattern V, $N^M$ is a 2'-O-methoxyethyl nucleoside; each $N^B$ is an S-cEt nucleoside; each $N^Q$ is a β-D-deoxyribonucleoside; and $N^Z$ is selected from a 2'-O-methoxyethyl nucleoside and an S-cEt nucleoside. In certain embodiments of nucleoside pattern V, $N^M$ is a 2'-O-methoxyethyl nucleoside; each $N^B$ is an S-cEt nucleoside; each $N^Q$ is a β-D-deoxyribonucleoside; and $N^Z$ is a 2'-O-methoxyethyl nucleoside. In certain embodiments, the modified oligonucleotide of pattern V has a nucleobase sequence selected from SEQ ID NOs: 3 to 10, wherein each T in the sequence is independently selected from T and U.

In certain embodiments of nucleoside pattern VI, each $N^B$ is an S-cEt nucleoside; and each $N^Q$ is a 2'-O-methoxyethyl nucleoside. In certain embodiments of nucleoside pattern VI, each $N^B$ is an S-cEt nucleoside; and each $N^Q$ is a β-D-deoxyribonucleoside. In certain embodiments, the modified oligonucleotide of pattern VI has a nucleobase sequence selected from SEQ ID NOs: 5 and 7, wherein each T in the sequence is independently selected from T and U.

In certain embodiments of nucleoside pattern VII, each $N^M$ is a 2'-O-methoxyethyl nucleoside; each $N^B$ is an S-cEt nucleoside; each $N^Q$ is independently selected from a 2'-O-methyl nucleoside and a β-D-deoxyribonucleoside; and $N^Z$ is selected from an S-cEt nucleoside and a 2'-O-methoxyethyl nucleoside. In certain embodiments of nucleoside pattern VII, each $N^M$ is a 2'-O-methoxyethyl nucleoside; each $N^B$ is an S-cEt nucleoside; each $N^Q$ is a β-D-deoxyribonucleoside; and $N^Z$ is an S-cEt nucleoside. In certain embodiments of nucleoside pattern VII, each $N^M$ is a 2'-O-methoxyethyl nucleoside; each $N^B$ is an S-cEt nucleoside; each $N^Q$ is independently selected from a 2'-O-methyl nucleoside and a β-D-deoxyribonucleoside; and $N^Z$ is an S-cEt nucleoside. In certain embodiments of nucleoside pattern VII, each $N^M$ is a 2'-O-methoxyethyl nucleoside; each $N^B$ is an S-cEt nucleoside; each $N^Q$ is independently selected from a 2'-O-methyl nucleoside and a β-D-deoxyribonucleoside; and $N^Z$ is a 2'-O-methoxyethyl nucleoside. In certain embodiments, the modified oligonucleotide of pattern VII has a nucleobase sequence selected from SEQ ID NOs: 3 to 10, wherein each T in the sequence is independently selected from T and U.

In certain embodiments, a compound provided herein has at least 8, at least 9, at least 10, at least 11, at least 12, at least 13, at least 14, at least 15, at least 16, at least 17, at least 18, or at least 19 contiguous nucleosides of a nucleobase sequence and modifications (i.e., a "structure") as shown in Table 1. In certain embodiments, a compound provided herein has a structure selected from the structures in Table 1. Nucleoside modifications are indicated as follows: nucleosides not followed by a subscript indicate β-D-deoxyribonucleosides; nucleosides followed by a subscript "E" indicate 2'-MOE nucleosides; nucleosides followed by a subscript "M" indicate 2'-O-methyl nucleosides; nucleosides followed by a subscript "S" indicate S-cEt nucleosides. Each internucleoside linkage is a phosphorothioate internucleoside linkage. Superscript "Me" indicates a 5-methyl group on the base of the nucleoside.

TABLE 1

Anti-miR-21 compounds

| Compound # | Sequence and Chemistry (5' to 3') | SEQ ID NO | Pattern |
|---|---|---|---|
| 25221 | $A_E C_S ATC_S AGTC_S TGAU_S AAGC_S U_S A_S$ | 3 | III, IV |
| 25220 | $A_E C_S ATC_S A_S GTC_S U_S GAU_S A_S AGC_S U_S A_E$ | 3 | V |
| 36328 | $^{Me}C_E A_S G_S T_E C_S U_S G_E A_E U_S A_S A_E G_E C_S T_E A_S$ | 5 | VI |
| 36284 | $^{Me}C_E A_S A_S T_E C_S U_S A_E A_E U_S A_S A_E G_E C_S T_E A_S$ | 7 | VI |
| 36232 | $CA_S G_S TC_S U_S GAU_S A_S AGC_S TA_S$ | 5 | VI |
| 36039 | $A_E C_S A_E T_E C_S A_E G_E T_E C_S TGAU_S AAGC_S TA_S$ | 3 | III, IV |
| 36730 | $U_S CAG_S TCU_S G_S AU_S AA_S GC_S U_S A_S$ | 6 | |
| 36731 | $A_E C_S A_E T_E C_S A_E G_E T_E C_S TGAU_S AAGC_S U_S A_S$ | 3 | III, IV, VII |
| 36842 | $A_E C_S A_E T_E C_S A_E G_E T_E C_S TG_S AU_S AA_S GC_S U_S A_S$ | 3 | |
| 36843 | $A_E C_S A_E T_E C_S A_E G_E T_E C_S TG_M AU_S AA_M GC_S U_S A_S$ | 3 | III, IV, VII |
| 36844 | $A_E C_S A_E T_E C_S A_E G_E T_E C_S TG_M AU_S AA_M GC_S U_S T_E$ | 8 | III, IV, VII |
| 36845 | $A_E C_S A_E T_E C_S A_E G_E T_E C_S TGA_M U_S A_M AGC_S U_S A_S$ | 3 | III, IV, VII |
| 36846 | $A_E C_S A_E T_E C_S A_E G_E T_E C_S TGA_M U_S A_M AGC_S U_S T_E$ | 8 | III, IV, VII |
| 36847 | $A_E C_S ATC_S A_S GTC_S U_S GAU_S A_S AGC_S U_S T_E$ | 8 | V |
| 36000 | $A_E C_S ATC_S A_E G_E T_E C_S TGA_E U_S A_E AGC_S U_S A_S$ | 3 | III, IV |
| 36001 | $A_E C_S ATC_S AG_E T_E C_S TGA_E U_S A_E AGC_S U_S A_S$ | 3 | III, IV |
| 36002 | $A_E C_S ATC_S AGT_E C_S TGA_E U_S A_E AGC_S U_S A_S$ | 3 | III, IV |
| 36003 | $A_E C_S ATC_S AGTC_S TGA_E U_S A_E AGC_S U_S A_S$ | 3 | III, IV |
| 36004 | $A_E C_S AT_E C_S A_E G_E T_E C_S TGA_E U_S A_E AGC_S U_S T_E$ | 8 | III, IV |
| 36005 | $A_E C_S ATC_S A_E G_E T_E C_S TGA_E U_S A_E AGC_S U_S T_E$ | 8 | III, IV |
| 36006 | $A_E C_S ATC_S AG_E T_E C_S TGA_E U_S A_E AGC_S U_S T_E$ | 8 | III, IV |
| 36007 | $A_E C_S ATC_S AGT_E C_S TGA_E U_S A_E AGC_S U_S T_E$ | 8 | III, IV |
| 36008 | $A_E C_S ATC_S AGTC_S TGA_E U_S A_E AGC_S U_S T_E$ | 8 | III, IV |
| 36009 | $A_E C_S A_E T_E C_S A_E G_E T_E C_S TGAU_S AAGC_S U_S$ | 10 | III, IV, VII |
| 36010 | $A_E C_S A_E T_E C_S A_E G_E T_E C_S TGAU_S A_M AGC_S U_S$ | 10 | III, IV, VII |
| 36011 | $A_E C_S A_E T_E C_S A_E G_E T_E C_S TGA_M U_S AAGC_S U_S$ | 10 | III, IV, VII |
| 36012 | $C_S A_E T_E C_S A_E G_E T_E C_S TGAU_S AAGC_S U_S A_S$ | 9 | III, IV, VII |

TABLE 1-continued

Anti-miR-21 compounds

| Compound # | Sequence and Chemistry (5' to 3') | SEQ ID NO | Pattern |
|---|---|---|---|
| 36016 | $A_E C_S A_E T_S C_S A_E G_E T C_S TGA_M U_S AAGC_S U_S A_S$ | 3 | III, IV |
| 36017 | $A_E C_S A_E TC_S A_E G_E T C_S TGA_M U_S AAGC_S U_S A_S$ | 3 | III, IV |
| 36018 | $A_E C_S A_E T_S C_S A_E G_E T C_S TGAU_S A_M AGC_S U_S A_S$ | 3 | III, IV |
| 36019 | $A_E C_S A_E TC_S A_E G_E T C_S TGAU_S A_M AGC_S U_S A_S$ | 3 | III, IV |
| 36020 | $A_E C_S A_E T_S C_S A_E G_E T_E C_S TGA_M U_S A_M AGC_S U_M A_S$ | 3 | III, IV |
| 36021 | $A_E C_S A_E T_S C_S A_E G_E T_E C_S TGA_M U_S AAGC_S U_M A_S$ | 3 | III, IV |
| 36022 | $A_E C_S A_E T_S C_S A_E G_E T C_S TGA_M U_S AAGC_S U_M A_S$ | 3 | III, IV |
| 36023 | $A_E C_S A_E TC_S A_E G_E T C_S TGA_M U_S AAGC_S U_M A_S$ | 3 | III, IV |
| 36024 | $A_E C_S A_E T_E C_S A_E G_E T_E C_S TGAU_S A_M AGC_S U_M A_S$ | 3 | III, IV |
| 36025 | $A_E C_S A_E T_S C_S A_E G_E T C_S TGAU_S A_M AGC_S U_M A_S$ | 3 | III, IV |
| 36026 | $A_E C_S A_E TC_S A_E G_E T C_S TGAU_S A_M AGC_S U_M A_S$ | 3 | III, IV |
| 36027 | $A_E C_S A_E T_S C_S A_E G_E T_E C_S TGAU_S AAGC_S U_M A_S$ | 3 | III, IV |
| 36028 | $A_E C_S A_E T_S C_S A_E G_E T C_S TGAU_S AAGC_S U_M A_S$ | 3 | III, IV |
| 36029 | $A_E C_S A_E TC_S A_E G_E T C_S TGAU_S AAGC_S U_M A_S$ | 3 | III, IV |
| 36030 | $A_E C_S A_E T_E C_S A_E G_E T_E C_S TGAU_S AAGC_S U_M T_E$ | 8 | III, IV |
| 36031 | $A_E C_S A_E T_S C_S A_E G_E T C_S TGAU_S AAGC_S U_M T_E$ | 8 | III, IV |
| 36032 | $A_E C_S A_E TC_S A_E G_E T C_S TGAU_S AAGC_S U_M T_E$ | 8 | III, IV |
| 36033 | $A_E C_S ATC_S A_S GTC_S U_S GAU_S A_M AGC_S U_S A_S$ | 3 | |
| 36034 | $A_E C_S ATC_S A_S GTC_S U_M GAU_S A_M AGC_S U_S A_S$ | 3 | |
| 36035 | $A_E C_S ATC_S A_M GTC_S U_M GAU_S A_M AGC_S U_S A_S$ | 3 | III, IV |
| 36040 | $A_E C_S ATC_S A_S GTC_S T_E GAU_S A_E AGC_S U_S A_S$ | 3 | |
| 36041 | $A_E C_S ATC_S A_E GTC_S T_E GAU_S A_E AGC_S U_S A_S$ | 3 | III, IV |
| 36045 | $A_E C_S AT_E C_S A_E G_E T_E C_S TGA_M U_S A_M AGC_S U_S T_E$ | 8 | III, IV |
| 36046 | $A_E C_S ATC_S A_E G_E T_E C_S TGA_M U_S A_M AGC_S U_S T_E$ | 8 | III, IV |
| 36047 | $A_E C_S ATC_S AG_E T_E C_S TGA_M U_S A_M AGC_S U_S T_E$ | 8 | III, IV |
| 36048 | $A_E C_S ATC_S AGT_E C_S TGA_M U_S A_M AGC_S U_S T_E$ | 8 | III, IV |
| 36049 | $A_E C_S ATC_S A_S GTC_S U_S GAU_S A_M AGC_S U_S T_E$ | 8 | |
| 36050 | $A_E C_S ATC_S A_S GTC_S U_M GAU_S A_M AGC_S U_S T_E$ | 8 | |
| 36051 | $A_E C_S ATC_S A_M GTC_S U_M GAU_S A_M AGC_S U_S T_E$ | 8 | III, IV |
| 36055 | $A_E C_S ATC_S A_S GTC_S U_S GAU_S A_S AGC_S U_S$ | 10 | V |
| 36239 | $A_E C_S ATC_S A_S GTC_S U_S GAU_S A_E AGC_S U_S A_S$ | 3 | |
| 36968 | $A_E C_S A_E T_E C_S A_E G_E TC_S TGAU_S AAGC_S U_S A_S$ | 3 | III, IV |
| 36969 | $A_E C_S A_E TC_S A_E G_E TC_S TGAU_S AAGC_S U_S A_S$ | 3 | III, IV |
| 36970 | $A_E C_S A_E T_E C_S A_E G_E T_E C_S TGAU_S AAGC_S U_S T_E$ | 8 | III, IV, VII |
| 36971 | $A_E C_S A_E T_E C_S A_E G_E TC_S TGAU_S AAGC_S U_S T_E$ | 8 | III, IV |
| 36972 | $A_E C_S A_E TC_S A_E G_E TC_S TGAU_S AAGC_S U_S T_E$ | 8 | III, IV |
| 36973 | $A_E C_S AT_E C_S A_E G_E T_E C_S TGAU_S AAGC_S U_S A_S$ | 3 | III, IV |

TABLE 1-continued

Anti-miR-21 compounds

| Compound # | Sequence and Chemistry (5' to 3') | SEQ ID NO | Pattern |
|---|---|---|---|
| 36974 | $A_E C_S A_E TC_S A_E G_E T_E C_S TGAU_S AAGC_S U_S A_S$ | 3 | III, IV |
| 36975 | $A_E C_S A_E T_E C_S AG_E T_E C_S TGAU_S AAGC_S U_S A_S$ | 3 | III, IV |
| 36976 | $A_E C_S A_E T_E C_S A_E GT_E C_S TGAU_S AAGC_S U_S A_S$ | 3 | III, IV |
| 36977 | $A_E C_S ATC_S A_E G_E T_E C_S TGAU_S AAGC_S U_S A_S$ | 3 | III, IV |
| 36978 | $A_E C_S A_E T_E C_S AGT_E C_S TGAU_S AAGC_S U_S A_S$ | 3 | III, IV |
| 36979 | $A_E C_S A_E T_E C_S A_E GTC_S TGAU_S AAGC_S U_S A_S$ | 3 | III, IV |
| 36980 | $A_E C_S ATC_S AG_E T_E C_S TGAU_S AAGC_S U_S A_S$ | 3 | III, IV |
| 36981 | $A_E C_S ATC_S AGT_E C_S TGAU_S AAGC_S U_S A_S$ | 3 | III, IV |
| 36982 | $A_E C_S A_E T_E C_S A_E G_E T_E C_S TGAU_S AAGC_S T_E A_S$ | 3 | III, IV, VII |
| 36984 | $A_E C_S A_E T_E C_S A_E G_E T_E C_S TGAU_S AAG_E C_S U_S A_S$ | 3 | III, IV, VII |
| 36985 | $A_E C_S A_E T_E C_S A_E G_E T_E C_S TGAU_S AA_E GC_S U_S A_S$ | 3 | III, IV, VII |
| 36986 | $A_E C_S A_E T_E C_S A_E G_E T_E C_S TGAU_S A_E AGC_S U_S A_S$ | 3 | III, IV, VII |
| 36988 | $A_E C_S A_E T_E C_S A_E G_E T_E C_S TGA_E U_S AAGC_S U_S A_S$ | 3 | III, IV, VII |
| 36989 | $A_E C_S A_E T_E C_S A_E G_E T_E C_S TG_E AU_S AAGC_S U_S A_S$ | 3 | III, IV, VII |
| 36990 | $A_E C_S A_E T_E C_S A_E G_E T_E C_S T_E GAU_S AAGC_S U_S A_S$ | 3 | III, IV, VII |
| 36992 | $A_E C_S A_E T_E C_S A_E G_E T_E C_S TGAU_S A_M AGC_S U_S A_S$ | 3 | III, IV, VII |
| 36993 | $A_E C_S A_E T_E C_S A_E G_E T_E C_S TGA_M U_S AAGC_S U_S A_S$ | 3 | III, IV, VII |
| 36994 | $A_E C_S AT_E C_S A_E G_E T_E C_S TGA_M U_S A_M AGC_S U_S A_S$ | 3 | III, IV |
| 36995 | $A_E C_S ATC_S A_E G_E T_E C_S TGA_M U_S A_M AGC_S U_S A_S$ | 3 | III, IV |
| 36996 | $A_E C_S ATC_S AG_E T_E C_S TGA_M U_S A_M AGC_S U_S A_S$ | 3 | III, IV |
| 36997 | $A_E C_S ATC_S AGT_E C_S TGA_M U_S A_M AGC_S U_S A_S$ | 3 | III, IV |
| 36998 | $A_E C_S ATC_S AGTC_S TGA_M U_S A_M AGC_S U_S A_S$ | 3 | III, IV |
| 36999 | $A_E C_S AT_E C_S A_E G_E T_E C_S TGA_E U_S A_E AGC_S U_S A_S$ | 3 | III, IV |

In certain embodiments of any of the nucleoside patterns described herein, a modified oligonucleotide consists of 8, 9, 10, 11, 12, 13, 14, 15, 16, 17, 18, 19, 20, 21, or 22 linked nucleosides. In certain embodiments, the modified oligonucleotide comprises at least 8 linked nucleosides of a nucleoside pattern set forth in nucleoside pattern III. In certain embodiments, the modified oligonucleotide comprises at least 8 linked nucleosides of a nucleoside pattern set forth in nucleoside pattern IV. In certain embodiments, the modified oligonucleotide comprises at least 8 linked nucleosides of a nucleoside pattern set forth in nucleoside pattern V. In certain embodiments, the modified oligonucleotide comprises at least 8 linked nucleosides of a nucleoside pattern set forth in nucleoside pattern VI. In certain embodiments, the modified oligonucleotide comprises at least 8 linked nucleosides of a nucleoside pattern set forth in nucleoside pattern VII.

In certain embodiments, a modified oligonucleotide having any of the nucleoside patterns described herein comprises at least one modified internucleoside linkage. In certain embodiments, each internucleoside linkage is a modified internucleoside linkage. In certain embodiments, the modified internucleoside linkage is a phosphorothioate internucleoside linkage.

In certain embodiments, a modified oligonucleotide has a nucleobase sequence wherein at least one nucleobase is a cytosine. In certain embodiments, at least one cytosine is a 5-methyl cytosine. In certain embodiments, each cytosine is a 5-methyl cytosine. In certain embodiments, at least one nucleoside comprises a modified nucleobase.

Modified oligonucleotides may undergo cleavage by exonucleases and/or endonucleases at various positions throughout the modified oligonucleotide. The products of such enzymatic cleavage may retain miR-21 inhibitory activity, and as such are considered active metabolites. As such, a metabolic product of a modified oligonucleotide may be used in the methods described herein.

In certain embodiments, a modified oligonucleotide targeted to miR-21 has a nucleoside pattern selected from Table 2A, where $N^M$ is a modified nucleoside that is not a bicyclic nucleoside; each $N^B$ is a bicyclic nucleoside; each $N^Q$ is a non-bicyclic nucleoside; $N^Y$ is a modified nucleoside or an unmodified nucleoside; and $N^Z$ is a modified nucleoside.

TABLE 2A

Metabolic Products of Nucleoside Pattern IV

```
5'                                                                    3'
N^M N^B N^Q N^Q N^B N^Q N^Q N^Q N^B N^Q N^Q N^Q N^B N^Q N^Q N^Q N^B N^Y N^Z
    N^B N^Q N^Q N^B N^Q N^Q N^Q N^B N^Q N^Q N^Q N^B N^Q N^Q N^Q N^B N^Y N^Z
        N^Q N^Q N^B N^Q N^Q N^Q N^B N^Q N^Q N^Q N^B N^Q N^Q N^Q N^B N^Y N^Z
            N^Q N^B N^Q N^Q N^Q N^B N^Q N^Q N^Q N^B N^Q N^Q N^Q N^B N^Y N^Z
                N^B N^Q N^Q N^Q N^B N^Q N^Q N^Q N^B N^Q N^Q N^Q N^B N^Y N^Z
                    N^Q N^Q N^Q N^B N^Q N^Q N^Q N^B N^Q N^Q N^Q N^B N^Y N^Z
                        N^Q N^Q N^B N^Q N^Q N^Q N^B N^Q N^Q N^Q N^B N^Y N^Z
                            N^Q N^B N^Q N^Q N^Q N^B N^Q N^Q N^Q N^B N^Y N^Z
                                N^B N^Q N^Q N^Q N^B N^Q N^Q N^Q N^B N^Y N^Z
                                    N^Q N^Q N^Q N^B N^Q N^Q N^Q N^B N^Y N^Z
                                        N^Q N^Q N^B N^Q N^Q N^Q N^B N^Y N^Z
                                            N^Q N^B N^Q N^Q N^Q N^B N^Y N^Z
N^M N^B N^Q N^Q N^B N^Q N^Q N^Q N^B N^Q N^Q N^Q N^B N^Q N^Q N^Q N^B N^Y
N^M N^B N^Q N^Q N^B N^Q N^Q N^Q N^B N^Q N^Q N^Q N^B N^Q N^Q N^Q N^B
    N^B N^Q N^Q N^B N^Q N^Q N^Q N^B N^Q N^Q N^Q N^B N^Q N^Q N^Q N^B N^Y
    N^B N^Q N^Q N^B N^Q N^Q N^Q N^B N^Q N^Q N^Q N^B N^Q N^Q N^Q N^B
        N^Q N^Q N^B N^Q N^Q N^Q N^B N^Q N^Q N^Q N^B N^Q N^Q N^Q N^B N^Y
        N^Q N^Q N^B N^Q N^Q N^Q N^B N^Q N^Q N^Q N^B N^Q N^Q N^Q N^B
            N^Q N^B N^Q N^Q N^Q N^B N^Q N^Q N^Q N^B N^Q N^Q N^Q N^B N^Y
            N^Q N^B N^Q N^Q N^Q N^B N^Q N^Q N^Q N^B N^Q N^Q N^Q N^B
                N^B N^Q N^Q N^Q N^B N^Q N^Q N^Q N^B N^Q N^Q N^Q N^B N^Y
                N^B N^Q N^Q N^Q N^B N^Q N^Q N^Q N^B N^Q N^Q N^Q N^B
                    N^Q N^Q N^Q N^B N^Q N^Q N^Q N^B N^Q N^Q N^Q N^B N^Y
                    N^Q N^Q N^Q N^B N^Q N^Q N^Q N^B N^Q N^Q N^Q N^B
                        N^Q N^Q N^B N^Q N^Q N^Q N^B N^Q N^Q N^Q N^B N^Y
                        N^Q N^Q N^B N^Q N^Q N^Q N^B N^Q N^Q N^Q N^B
                            N^Q N^B N^Q N^Q N^Q N^B N^Q N^Q N^Q N^B N^Y
                            N^Q N^B N^Q N^Q N^Q N^B N^Q N^Q N^Q N^B
                                N^B N^Q N^Q N^Q N^B N^Q N^Q N^Q N^B N^Y
                                N^B N^Q N^Q N^Q N^B N^Q N^Q N^Q N^B
                                    N^Q N^Q N^Q N^B N^Q N^Q N^Q N^B N^Y
                                    N^Q N^Q N^Q N^B N^Q N^Q N^Q N^B
                                        N^Q N^Q N^B N^Q N^Q N^Q N^B N^Y
```

In certain embodiments, a modified oligonucleotide targeted to miR-21 has a nucleoside pattern selected from Table 2B, where $N^M$ is a modified nucleoside that is not a bicyclic nucleoside; each $N^B$ is a bicyclic nucleoside; each $N^Q$ is a non-bicyclic nucleoside; and $N^Z$ is a modified nucleoside.

TABLE 2B

Metabolic Products of Nucleoside Pattern V

```
5'                                                                              3'
N^M N^B N^Q N^Q N^B N^B N^Q N^Q N^B N^B N^Q N^Q N^B N^B N^Q N^Q N^B N^B N^Z
    N^B N^Q N^Q N^B N^B N^Q N^Q N^B N^B N^Q N^Q N^B N^B N^Q N^Q N^B N^B N^Z
        N^Q N^Q N^B N^B N^Q N^Q N^B N^B N^Q N^Q N^B N^B N^Q N^Q N^B N^B N^Z
            N^Q N^B N^B N^Q N^Q N^B N^B N^Q N^Q N^B N^B N^Q N^Q N^B N^B N^Z
                N^B N^B N^Q N^Q N^B N^B N^Q N^Q N^B N^B N^Q N^Q N^B N^B N^Z
                    N^B N^Q N^Q N^B N^B N^Q N^Q N^B N^B N^Q N^Q N^B N^B N^Z
                        N^Q N^Q N^B N^B N^Q N^Q N^B N^B N^Q N^Q N^B N^B N^Z
                            N^Q N^B N^B N^Q N^Q N^B N^B N^Q N^Q N^B N^B N^Z
                                N^B N^B N^Q N^Q N^B N^B N^Q N^Q N^B N^B N^Z
                                    N^B N^Q N^Q N^B N^B N^Q N^Q N^B N^B N^Z
                                        N^Q N^Q N^B N^B N^Q N^Q N^B N^B N^Z
                                            N^Q N^B N^B N^Q N^Q N^B N^B N^Z
N^M N^B N^Q N^Q N^B N^B N^Q N^Q N^B N^B N^Q N^Q N^B N^B N^Q N^Q N^B N^B
N^M N^B N^Q N^Q N^B N^B N^Q N^Q N^B N^B N^Q N^Q N^B N^B N^Q N^Q N^B
    N^B N^Q N^Q N^B N^B N^Q N^Q N^B N^B N^Q N^Q N^B N^B N^Q N^Q N^B N^B
    N^B N^Q N^Q N^B N^B N^Q N^Q N^B N^B N^Q N^Q N^B N^B N^Q N^Q N^B
        N^Q N^Q N^B N^B N^Q N^Q N^B N^B N^Q N^Q N^B N^B N^Q N^Q N^B N^B
        N^Q N^Q N^B N^B N^Q N^Q N^B N^B N^Q N^Q N^B N^B N^Q N^Q N^B
            N^Q N^B N^B N^Q N^Q N^B N^B N^Q N^Q N^B N^B N^Q N^Q N^B N^B
            N^Q N^B N^B N^Q N^Q N^B N^B N^Q N^Q N^B N^B N^Q N^Q N^B
                N^B N^B N^Q N^Q N^B N^B N^Q N^Q N^B N^B N^Q N^Q N^B N^B
                N^B N^B N^Q N^Q N^B N^B N^Q N^Q N^B N^B N^Q N^Q N^B
                    N^B N^Q N^Q N^B N^B N^Q N^Q N^B N^B N^Q N^Q N^B N^B
                    N^B N^Q N^Q N^B N^B N^Q N^Q N^B N^B N^Q N^Q N^B
                        N^Q N^Q N^B N^B N^Q N^Q N^B N^B N^Q N^Q N^B N^B
                        N^Q N^Q N^B N^B N^Q N^Q N^B N^B N^Q N^Q N^B
                            N^Q N^B N^B N^Q N^Q N^B N^B N^Q N^Q N^B N^B
                            N^Q N^B N^B N^Q N^Q N^B N^B N^Q N^Q N^B
                                N^B N^B N^Q N^Q N^B N^B N^Q N^Q N^B N^B
```

TABLE 2B-continued

Metabolic Products of Nucleoside Pattern V

5'                                                                3'

$N^B$ $N^B$ $N^Q$ $N^Q$ $N^B$ $N^B$ $N^Q$ $N^Q$ $N^B$
$N^B$ $N^Q$ $N^Q$ $N^B$ $N^B$ $N^Q$ $N^Q$ $N^B$ $N^B$
$N^Q$ $N^Q$ $N^Q$ $N^B$ $N^B$ $N^Q$ $N^Q$ $N^B$
$N^Q$ $N^Q$ $N^B$ $N^B$ $N^Q$ $N^Q$ $N^B$ $N^B$

In certain embodiments, a modified oligonucleotide targeted to miR-21 has a nucleoside pattern selected from Table 2C, where each $N^B$ is a bicyclic nucleoside; and each $N^Q$ is a non-bicyclic nucleoside

TABLE 2C

Metabolic Products of Nucleoside Pattern VI

5'                                                                                                3'

$N^Q$ $N^B$ $N^B$ $N^Q$ $N^B$ $N^B$ $N^Q$ $N^Q$ $N^B$ $N^B$ $N^Q$ $N^Q$ $N^B$ $N^Q$ $N^B$
$N^B$ $N^B$ $N^Q$ $N^B$ $N^B$ $N^Q$ $N^Q$ $N^B$ $N^B$ $N^Q$ $N^Q$ $N^B$ $N^Q$ $N^B$
$N^B$ $N^Q$ $N^B$ $N^B$ $N^Q$ $N^Q$ $N^B$ $N^B$ $N^Q$ $N^Q$ $N^B$ $N^Q$ $N^B$
$N^Q$ $N^B$ $N^B$ $N^Q$ $N^Q$ $N^B$ $N^B$ $N^Q$ $N^Q$ $N^B$ $N^Q$ $N^B$
$N^B$ $N^B$ $N^Q$ $N^Q$ $N^B$ $N^B$ $N^Q$ $N^Q$ $N^B$ $N^Q$ $N^B$
$N^B$ $N^Q$ $N^Q$ $N^B$ $N^B$ $N^Q$ $N^Q$ $N^B$ $N^Q$ $N^B$
$N^Q$ $N^Q$ $N^B$ $N^B$ $N^Q$ $N^Q$ $N^B$ $N^Q$ $N^B$
$N^Q$ $N^B$ $N^B$ $N^Q$ $N^Q$ $N^B$ $N^Q$ $N^B$
$N^Q$ $N^B$ $N^B$ $N^Q$ $N^B$ $N^B$ $N^Q$ $N^Q$ $N^B$ $N^B$ $N^Q$ $N^Q$ $N^B$ $N^Q$
$N^Q$ $N^B$ $N^B$ $N^Q$ $N^B$ $N^B$ $N^Q$ $N^Q$ $N^B$ $N^B$ $N^Q$ $N^Q$ $N^B$
$N^B$ $N^B$ $N^Q$ $N^B$ $N^B$ $N^Q$ $N^Q$ $N^B$ $N^B$ $N^Q$ $N^Q$ $N^B$ $N^Q$

TABLE 2C-continued

Metabolic Products of Nucleoside Pattern VI

5'                                                                                3'

$N^B$ $N^B$ $N^Q$ $N^B$ $N^B$ $N^Q$ $N^Q$ $N^B$ $N^B$ $N^Q$ $N^Q$ $N^B$
$N^B$ $N^Q$ $N^B$ $N^B$ $N^Q$ $N^Q$ $N^B$ $N^B$ $N^Q$ $N^Q$ $N^B$ $N^Q$
$N^B$ $N^Q$ $N^B$ $N^B$ $N^Q$ $N^Q$ $N^B$ $N^B$ $N^Q$ $N^Q$ $N^B$
$N^Q$ $N^B$ $N^B$ $N^Q$ $N^Q$ $N^B$ $N^B$ $N^Q$ $N^Q$ $N^B$ $N^Q$
$N^Q$ $N^B$ $N^B$ $N^Q$ $N^Q$ $N^B$ $N^B$ $N^Q$ $N^Q$ $N^B$
$N^B$ $N^B$ $N^Q$ $N^Q$ $N^B$ $N^B$ $N^Q$ $N^Q$ $N^B$ $N^Q$
$N^B$ $N^B$ $N^Q$ $N^Q$ $N^B$ $N^B$ $N^Q$ $N^Q$ $N^B$
$N^B$ $N^Q$ $N^Q$ $N^B$ $N^B$ $N^Q$ $N^Q$ $N^B$ $N^Q$
$N^B$ $N^Q$ $N^Q$ $N^B$ $N^B$ $N^Q$ $N^Q$ $N^B$
$N^Q$ $N^Q$ $N^B$ $N^B$ $N^Q$ $N^Q$ $N^B$ $N^Q$

In certain embodiments, a modified oligonucleotide targeted to miR-21 has a nucleoside pattern selected from Table 2D, where $N^M$ is a modified nucleoside that is not a bicyclic nucleoside; each $N^B$ is a bicyclic nucleoside; each $N^Q$ is a non-bicyclic nucleoside; and $N^Z$ is a modified nucleoside.

TABLE 2D

Metabolic Products of Nucleoside Pattern VII

5'                                                                                                                3'

$N^M$ $N^B$ $N^M$ $N^M$ $N^B$ $N^M$ $N^M$ $N^M$ $N^B$ $N^Q$ $N^Q$ $N^Q$ $N^B$ $N^Q$ $N^Q$ $N^Q$ $N^B$ $N^B$ $N^Z$
$N^B$ $N^M$ $N^M$ $N^B$ $N^M$ $N^M$ $N^M$ $N^B$ $N^Q$ $N^Q$ $N^Q$ $N^B$ $N^Q$ $N^Q$ $N^Q$ $N^B$ $N^B$ $N^Z$
$N^M$ $N^M$ $N^B$ $N^M$ $N^M$ $N^M$ $N^B$ $N^Q$ $N^Q$ $N^Q$ $N^B$ $N^Q$ $N^Q$ $N^Q$ $N^B$ $N^B$ $N^Z$
$N^M$ $N^B$ $N^M$ $N^M$ $N^M$ $N^B$ $N^Q$ $N^Q$ $N^Q$ $N^B$ $N^Q$ $N^Q$ $N^Q$ $N^B$ $N^B$ $N^Z$
$N^B$ $N^M$ $N^M$ $N^M$ $N^B$ $N^Q$ $N^Q$ $N^Q$ $N^B$ $N^Q$ $N^Q$ $N^Q$ $N^B$ $N^B$ $N^Z$
$N^M$ $N^M$ $N^M$ $N^B$ $N^Q$ $N^Q$ $N^Q$ $N^B$ $N^Q$ $N^Q$ $N^Q$ $N^B$ $N^B$ $N^Z$
$N^M$ $N^M$ $N^B$ $N^Q$ $N^Q$ $N^Q$ $N^B$ $N^Q$ $N^Q$ $N^Q$ $N^B$ $N^B$ $N^Z$
$N^M$ $N^B$ $N^Q$ $N^Q$ $N^Q$ $N^B$ $N^Q$ $N^Q$ $N^Q$ $N^B$ $N^B$ $N^Z$
$N^B$ $N^Q$ $N^Q$ $N^Q$ $N^B$ $N^Q$ $N^Q$ $N^Q$ $N^B$ $N^B$ $N^Z$
$N^Q$ $N^Q$ $N^Q$ $N^B$ $N^Q$ $N^Q$ $N^Q$ $N^B$ $N^B$ $N^Z$
$N^Q$ $N^Q$ $N^B$ $N^Q$ $N^Q$ $N^Q$ $N^B$ $N^B$ $N^Z$
$N^M$ $N^B$ $N^M$ $N^M$ $N^B$ $N^M$ $N^M$ $N^M$ $N^B$ $N^Q$ $N^Q$ $N^Q$ $N^B$ $N^Q$ $N^Q$ $N^Q$ $N^B$ $N^B$
$N^M$ $N^B$ $N^M$ $N^M$ $N^B$ $N^M$ $N^M$ $N^M$ $N^B$ $N^Q$ $N^Q$ $N^Q$ $N^B$ $N^Q$ $N^Q$ $N^Q$ $N^B$
$N^B$ $N^M$ $N^M$ $N^B$ $N^M$ $N^M$ $N^M$ $N^B$ $N^Q$ $N^Q$ $N^Q$ $N^B$ $N^Q$ $N^Q$ $N^Q$ $N^B$ $N^B$
$N^B$ $N^M$ $N^M$ $N^B$ $N^M$ $N^M$ $N^M$ $N^B$ $N^Q$ $N^Q$ $N^Q$ $N^B$ $N^Q$ $N^Q$ $N^Q$ $N^B$
$N^M$ $N^M$ $N^B$ $N^M$ $N^M$ $N^M$ $N^B$ $N^Q$ $N^Q$ $N^Q$ $N^B$ $N^Q$ $N^Q$ $N^Q$ $N^B$ $N^B$
$N^M$ $N^M$ $N^B$ $N^M$ $N^M$ $N^M$ $N^B$ $N^Q$ $N^Q$ $N^Q$ $N^B$ $N^Q$ $N^Q$ $N^Q$ $N^B$
$N^M$ $N^B$ $N^M$ $N^M$ $N^M$ $N^B$ $N^Q$ $N^Q$ $N^Q$ $N^B$ $N^Q$ $N^Q$ $N^Q$ $N^B$ $N^B$
$N^M$ $N^B$ $N^M$ $N^M$ $N^M$ $N^B$ $N^Q$ $N^Q$ $N^Q$ $N^B$ $N^Q$ $N^Q$ $N^Q$ $N^B$
$N^B$ $N^M$ $N^M$ $N^M$ $N^B$ $N^Q$ $N^Q$ $N^Q$ $N^B$ $N^Q$ $N^Q$ $N^Q$ $N^B$ $N^B$
$N^B$ $N^M$ $N^M$ $N^M$ $N^B$ $N^Q$ $N^Q$ $N^Q$ $N^B$ $N^Q$ $N^Q$ $N^Q$ $N^B$
$N^M$ $N^M$ $N^M$ $N^B$ $N^Q$ $N^Q$ $N^Q$ $N^B$ $N^Q$ $N^Q$ $N^Q$ $N^B$ $N^B$
$N^M$ $N^M$ $N^M$ $N^B$ $N^Q$ $N^Q$ $N^Q$ $N^B$ $N^Q$ $N^Q$ $N^Q$ $N^B$
$N^M$ $N^M$ $N^B$ $N^Q$ $N^Q$ $N^Q$ $N^B$ $N^Q$ $N^Q$ $N^Q$ $N^B$ $N^B$
$N^M$ $N^M$ $N^B$ $N^Q$ $N^Q$ $N^Q$ $N^B$ $N^Q$ $N^Q$ $N^Q$ $N^B$
$N^M$ $N^B$ $N^Q$ $N^Q$ $N^Q$ $N^B$ $N^Q$ $N^Q$ $N^Q$ $N^B$ $N^B$
$N^M$ $N^B$ $N^Q$ $N^Q$ $N^Q$ $N^B$ $N^Q$ $N^Q$ $N^Q$ $N^B$
$N^B$ $N^Q$ $N^Q$ $N^Q$ $N^B$ $N^Q$ $N^Q$ $N^Q$ $N^B$ $N^B$
$N^B$ $N^Q$ $N^Q$ $N^Q$ $N^B$ $N^Q$ $N^Q$ $N^Q$ $N^B$
$N^Q$ $N^Q$ $N^Q$ $N^B$ $N^Q$ $N^Q$ $N^Q$ $N^B$ $N^B$
$N^Q$ $N^Q$ $N^Q$ $N^B$ $N^Q$ $N^Q$ $N^Q$ $N^B$
$N^Q$ $N^Q$ $N^B$ $N^Q$ $N^Q$ $N^Q$ $N^B$ $N^B$

In certain embodiments, a modified oligonucleotide targeted to miR-21 has a nucleoside pattern and nucleobase sequence selected from Table 3A, Table 3B, Table 3C, Table 3D, Table 3D, or Table 3E. Nucleosides not followed by a subscript indicate β-D-deoxyribonucleosides. Nucleosides followed by a subscript "E" indicate 2'-MOE nucleosides. Nucleosides followed by a subscript "S" indicate S-cEt nucleosides. Each internucleoside linkage is a phosphorothioate internucleoside linkage. Nucleobases may or may not comprise a methyl group at the 5' position.

TABLE 3A

Metabolic products of compound # 25221

| 5' $N_1$ | $N_2$ | $N_3$ | $N_4$ | $N_5$ | $N_6$ | $N_7$ | $N_8$ | $N_9$ | $N_{10}$ | $N_{11}$ | $N_{12}$ | $N_{13}$ | $N_{14}$ | $N_{15}$ | $N_{16}$ | $N_{17}$ | $N_{18}$ | 3' $N_{19}$ | SEQ ID NO |
|---|---|---|---|---|---|---|---|---|---|---|---|---|---|---|---|---|---|---|---|
| $A_E$ | $C_S$ | A | T | $C_S$ | A | G | T | $C_S$ | T | G | A | $U_S$ | A | A | G | $C_S$ | $U_S$ | $A_S$ | 3 |
|  | $C_S$ | A | T | $C_S$ | A | G | T | $C_S$ | T | G | A | $U_S$ | A | A | G | $C_S$ | $U_S$ | $A_S$ | 9 |
|  |  | A | T | $C_S$ | A | G | T | $C_S$ | T | G | A | $U_S$ | A | A | G | $C_S$ | $U_S$ | $A_S$ | 17 |
|  |  |  | T | $C_S$ | A | G | T | $C_S$ | T | G | A | $U_S$ | A | A | G | $C_S$ | $U_S$ | $A_S$ | 18 |
|  |  |  |  | $C_S$ | A | G | T | $C_S$ | T | G | A | $U_S$ | A | A | G | $C_S$ | $U_S$ | $A_S$ | 19 |
|  |  |  |  |  | A | G | T | $C_S$ | T | G | A | $U_S$ | A | A | G | $C_S$ | $U_S$ | $A_S$ | 20 |
|  |  |  |  |  |  | G | T | $C_S$ | T | G | A | $U_S$ | A | A | G | $C_S$ | $U_S$ | $A_S$ | 21 |
|  |  |  |  |  |  |  | T | $C_S$ | T | G | A | $U_S$ | A | A | G | $C_S$ | $U_S$ | $A_S$ | 22 |
|  |  |  |  |  |  |  |  | $C_S$ | T | G | A | $U_S$ | A | A | G | $C_S$ | $U_S$ | $A_S$ | 23 |
|  |  |  |  |  |  |  |  |  | T | G | A | $U_S$ | A | A | G | $C_S$ | $U_S$ | $A_S$ | 24 |
|  |  |  |  |  |  |  |  |  |  | G | A | $U_S$ | A | A | G | $C_S$ | $U_S$ | $A_S$ |  |
|  |  |  |  |  |  |  |  |  |  |  | A | $U_S$ | A | A | G | $C_S$ | $U_S$ | $A_S$ |  |
| $A_E$ | $C_S$ | A | T | $C_S$ | A | G | T | $C_S$ | T | G | A | $U_S$ | A | A | G | $C_S$ | $U_S$ |  | 25 |
| $A_E$ | $C_S$ | A | T | $C_S$ | A | G | T | $C_S$ | T | G | A | $U_S$ | A | A | G | $C_S$ |  |  | 26 |
|  | $C_S$ | A | T | $C_S$ | A | G | T | $C_S$ | T | G | A | $U_S$ | A | A | G | $C_S$ | $U_S$ |  | 27 |
|  | $C_S$ | A | T | $C_S$ | A | G | T | $C_S$ | T | G | A | $U_S$ | A | A | G | $C_S$ |  |  | 28 |
|  |  | A | T | $C_S$ | A | G | T | $C_S$ | T | G | A | $U_S$ | A | A | G | $C_S$ | $U_S$ |  | 29 |
|  |  | A | T | $C_S$ | A | G | T | $C_S$ | T | G | A | $U_S$ | A | A | G | $C_S$ |  |  | 30 |
|  |  |  | T | $C_S$ | A | G | T | $C_S$ | T | G | A | $U_S$ | A | A | G | $C_S$ | $U_S$ |  | 31 |
|  |  |  | T | $C_S$ | A | G | T | $C_S$ | T | G | A | $U_S$ | A | A | G | $C_S$ |  |  | 32 |
|  |  |  |  | $C_S$ | A | G | T | $C_S$ | T | G | A | $U_S$ | A | A | G | $C_S$ | $U_S$ |  | 33 |
|  |  |  |  | $C_S$ | A | G | T | $C_S$ | T | G | A | $U_S$ | A | A | G | $C_S$ |  |  | 34 |
|  |  |  |  |  | A | G | T | $C_S$ | T | G | A | $U_S$ | A | A | G | $C_S$ | $U_S$ |  | 35 |
|  |  |  |  |  | A | G | T | $C_S$ | T | G | A | $U_S$ | A | A | G | $C_S$ |  |  | 36 |
|  |  |  |  |  |  | G | T | $C_S$ | T | G | A | $U_S$ | A | A | G | $C_S$ | $U_S$ |  | 37 |
|  |  |  |  |  |  | G | T | $C_S$ | T | G | A | $U_S$ | A | A | G | $C_S$ |  |  | 38 |
|  |  |  |  |  |  |  | T | $C_S$ | T | G | A | $U_S$ | A | A | G | $C_S$ | $U_S$ |  | 39 |
|  |  |  |  |  |  |  | T | $C_S$ | T | G | A | $U_S$ | A | A | G | $C_S$ |  |  | 40 |
|  |  |  |  |  |  |  |  | $C_S$ | T | G | A | $U_S$ | A | A | G | $C_S$ | $U_S$ |  | 41 |
|  |  |  |  |  |  |  |  | $C_S$ | T | G | A | $U_S$ | A | A | G | $C_S$ |  |  |  |
|  |  |  |  |  |  |  |  |  | T | G | A | $U_S$ | A | A | G | $C_S$ | $U_S$ |  |  |
|  |  |  |  |  |  |  |  |  | T | G | A | $U_S$ | A | A | G | $C_S$ |  |  |  |
|  |  |  |  |  |  |  |  |  |  | G | A | $U_S$ | A | A | G | $C_S$ | $U_S$ |  |  |

TABLE 3B

Metabolic products of compound # 25220

| 5' $N_1$ | $N_2$ | $N_3$ | $N_4$ | $N_5$ | $N_6$ | $N_7$ | $N_8$ | $N_9$ | $N_{10}$ | $N_{11}$ | $N_{12}$ | $N_{13}$ | $N_{14}$ | $N_{15}$ | $N_{16}$ | $N_{17}$ | $N_{18}$ | 3' $N_{19}$ | SEQ ID NO |
|---|---|---|---|---|---|---|---|---|---|---|---|---|---|---|---|---|---|---|---|
| $A_E$ | $C_S$ | A | T | $C_S$ | $A_S$ | G | T | $C_S$ | $U_S$ | G | A | $U_S$ | $A_S$ | A | G | $C_S$ | $U_S$ | $A_E$ | 3 |
|  | $C_S$ | A | T | $C_S$ | $A_S$ | G | T | $C_S$ | $U_S$ | G | A | $U_S$ | $A_S$ | A | G | $C_S$ | $U_S$ | $A_E$ | 9 |
|  |  | A | T | $C_S$ | $A_S$ | G | T | $C_S$ | $U_S$ | G | A | $U_S$ | $A_S$ | A | G | $C_S$ | $U_S$ | $A_E$ | 17 |
|  |  |  | T | $C_S$ | $A_S$ | G | T | $C_S$ | $U_S$ | G | A | $U_S$ | $A_S$ | A | G | $C_S$ | $U_S$ | $A_E$ | 18 |
|  |  |  |  | $C_S$ | $A_S$ | G | T | $C_S$ | $U_S$ | G | A | $U_S$ | $A_S$ | A | G | $C_S$ | $U_S$ | $A_E$ | 19 |
|  |  |  |  |  | $A_S$ | G | T | $C_S$ | $U_S$ | G | A | $U_S$ | $A_S$ | A | G | $C_S$ | $U_S$ | $A_E$ | 20 |
|  |  |  |  |  |  | G | T | $C_S$ | $U_S$ | G | A | $U_S$ | $A_S$ | A | G | $C_S$ | $U_S$ | $A_E$ | 21 |
|  |  |  |  |  |  |  | T | $C_S$ | $U_S$ | G | A | $U_S$ | $A_S$ | A | G | $C_S$ | $U_S$ | $A_E$ | 22 |
|  |  |  |  |  |  |  |  | $C_S$ | $U_S$ | G | A | $U_S$ | $A_S$ | A | G | $C_S$ | $U_S$ | $A_E$ | 23 |
|  |  |  |  |  |  |  |  |  | $U_S$ | G | A | $U_S$ | $A_S$ | A | G | $C_S$ | $U_S$ | $A_E$ | 24 |
|  |  |  |  |  |  |  |  |  |  | G | A | $U_S$ | $A_S$ | A | G | $C_S$ | $U_S$ | $A_E$ |  |
|  |  |  |  |  |  |  |  |  |  |  | A | $U_S$ | $A_S$ | A | G | $C_S$ | $U_S$ | $A_E$ |  |
| $A_E$ | $C_S$ | A | T | $C_S$ | $A_S$ | G | T | $C_S$ | $U_S$ | G | A | $U_S$ | $A_S$ | A | G | $C_S$ | $U_S$ |  | 25 |
| $A_E$ | $C_S$ | A | T | $C_S$ | $A_S$ | G | T | $C_S$ | $U_S$ | G | A | $U_S$ | $A_S$ | A | G | $C_S$ |  |  | 26 |
|  | $C_S$ | A | T | $C_S$ | $A_S$ | G | T | $C_S$ | $U_S$ | G | A | $U_S$ | $A_S$ | A | G | $C_S$ | $U_S$ |  | 27 |
|  | $C_S$ | A | T | $C_S$ | $A_S$ | G | T | $C_S$ | $U_S$ | G | A | $U_S$ | $A_S$ | A | G | $C_S$ |  |  | 28 |
|  |  | A | T | $C_S$ | $A_S$ | G | T | $C_S$ | $U_S$ | G | A | $U_S$ | $A_S$ | A | G | $C_S$ | $U_S$ |  | 29 |
|  |  | A | T | $C_S$ | $A_S$ | G | T | $C_S$ | $U_S$ | G | A | $U_S$ | $A_S$ | A | G | $C_S$ |  |  | 30 |
|  |  |  | T | $C_S$ | $A_S$ | G | T | $C_S$ | $U_S$ | G | A | $U_S$ | $A_S$ | A | G | $C_S$ | $U_S$ |  | 31 |
|  |  |  | T | $C_S$ | $A_S$ | G | T | $C_S$ | $U_S$ | G | A | $U_S$ | $A_S$ | A | G | $C_S$ |  |  | 32 |
|  |  |  |  | $C_S$ | $A_S$ | G | T | $C_S$ | $U_S$ | G | A | $U_S$ | $A_S$ | A | G | $C_S$ | $U_S$ |  | 33 |
|  |  |  |  | $C_S$ | $A_S$ | G | T | $C_S$ | $U_S$ | G | A | $U_S$ | $A_S$ | A | G | $C_S$ |  |  | 34 |

TABLE 3B-continued

Metabolic products of compound # 25220

| N1 | N2 | N3 | N4 | N5 | N6 | N7 | N8 | N9 | N10 | N11 | N12 | N13 | N14 | N15 | N16 | N17 | N18 | N19 | SEQ ID NO |
|---|---|---|---|---|---|---|---|---|---|---|---|---|---|---|---|---|---|---|---|
| | | | | | $A_S$ | G | T | $C_S$ | $U_S$ | G | A | $U_S$ | $A_S$ | A | G | $C_S$ | $U_S$ | | 35 |
| | | | | | $A_S$ | G | T | $C_S$ | $U_S$ | G | A | $U_S$ | $A_S$ | A | G | $C_S$ | | | 36 |
| | | | | | | G | T | $C_S$ | $U_S$ | G | A | $U_S$ | $A_S$ | A | G | $C_S$ | $U_S$ | | 37 |
| | | | | | | G | T | $C_S$ | $U_S$ | G | A | $U_S$ | $A_S$ | A | G | $C_S$ | | | 38 |
| | | | | | | | T | $C_S$ | $U_S$ | G | A | $U_S$ | $A_S$ | A | G | $C_S$ | $U_S$ | | 39 |
| | | | | | | | T | $C_S$ | $U_S$ | G | A | $U_S$ | $A_S$ | A | G | $C_S$ | | | 40 |
| | | | | | | | | $C_S$ | $U_S$ | G | A | $U_S$ | $A_S$ | A | G | $C_S$ | $U_S$ | | 41 |
| | | | | | | | | $C_S$ | $U_S$ | G | A | $U_S$ | $A_S$ | A | G | $C_S$ | | | |
| | | | | | | | | | $U_S$ | G | A | $U_S$ | $A_S$ | A | G | $C_S$ | $U_S$ | | |
| | | | | | | | | | $U_S$ | G | A | $U_S$ | $A_S$ | A | G | $C_S$ | | | |
| | | | | | | | | | | G | A | $U_S$ | $A_S$ | A | G | $C_S$ | $U_S$ | | |

TABLE 3C

Metabolic products of compound # 36284

| N1 | N2 | N3 | N4 | N5 | N6 | N7 | N8 | N9 | N10 | N11 | N12 | N13 | N14 | N15 | SEQ ID NO |
|---|---|---|---|---|---|---|---|---|---|---|---|---|---|---|---|
| $^{Me}C_E$ | $A_S$ | $A_S$ | $T_E$ | $C_S$ | $U_S$ | $A_E$ | $A_E$ | $U_S$ | $A_S$ | $A_E$ | $G_E$ | $C_S$ | $T_E$ | $A_S$ | 7 |
| | $A_S$ | $A_S$ | $T_E$ | $C_S$ | $U_S$ | $A_E$ | $A_E$ | $U_S$ | $A_S$ | $A_E$ | $G_E$ | $C_S$ | $T_E$ | $A_S$ | 42 |
| | | $A_S$ | $T_E$ | $C_S$ | $U_S$ | $A_E$ | $A_E$ | $U_S$ | $A_S$ | $A_E$ | $G_E$ | $C_S$ | $T_E$ | $A_S$ | 43 |
| | | | $T_E$ | $C_S$ | $U_S$ | $A_E$ | $A_E$ | $U_S$ | $A_S$ | $A_E$ | $G_E$ | $C_S$ | $T_E$ | $A_S$ | 44 |
| | | | | $C_S$ | $U_S$ | $A_E$ | $A_E$ | $U_S$ | $A_S$ | $A_E$ | $G_E$ | $C_S$ | $T_E$ | $A_S$ | 45 |
| | | | | | $U_S$ | $A_E$ | $A_E$ | $U_S$ | $A_S$ | $A_E$ | $G_E$ | $C_S$ | $T_E$ | $A_S$ | 46 |
| | | | | | | $A_E$ | $A_E$ | $U_S$ | $A_S$ | $A_E$ | $G_E$ | $C_S$ | $T_E$ | $A_S$ | |
| | | | | | | | $A_E$ | $U_S$ | $A_S$ | $A_E$ | $G_E$ | $C_S$ | $T_E$ | $A_S$ | |
| $^{Me}C_E$ | $A_S$ | $A_S$ | $T_E$ | $C_S$ | $U_S$ | $A_E$ | $A_E$ | $U_S$ | $A_S$ | $A_E$ | $G_E$ | $C_S$ | $T_E$ | | 47 |
| $^{Me}C_E$ | $A_S$ | $A_S$ | $T_E$ | $C_S$ | $U_S$ | $A_E$ | $A_E$ | $U_S$ | $A_S$ | $A_E$ | $G_E$ | $C_S$ | | | 48 |
| | $A_S$ | $A_S$ | $T_E$ | $C_S$ | $U_S$ | $A_E$ | $A_E$ | $U_S$ | $A_S$ | $A_E$ | $G_E$ | $C_S$ | $T_E$ | | 49 |
| | $A_S$ | $A_S$ | $T_E$ | $C_S$ | $U_S$ | $A_E$ | $A_E$ | $U_S$ | $A_S$ | $A_E$ | $G_E$ | $C_S$ | | | 50 |
| | | $A_S$ | $T_E$ | $C_S$ | $U_S$ | $A_E$ | $A_E$ | $U_S$ | $A_S$ | $A_E$ | $G_E$ | $C_S$ | $T_E$ | | 51 |
| | | $A_S$ | $T_E$ | $C_S$ | $U_S$ | $A_E$ | $A_E$ | $U_S$ | $A_S$ | $A_E$ | $G_E$ | $C_S$ | | | 52 |
| | | | $T_E$ | $C_S$ | $U_S$ | $A_E$ | $A_E$ | $U_S$ | $A_S$ | $A_E$ | $G_E$ | $C_S$ | $T_E$ | | 53 |
| | | | $T_E$ | $C_S$ | $U_S$ | $A_E$ | $A_E$ | $U_S$ | $A_S$ | $A_E$ | $G_E$ | $C_S$ | | | 54 |
| | | | | $C_S$ | $U_S$ | $A_E$ | $A_E$ | $U_S$ | $A_S$ | $A_E$ | $G_E$ | $C_S$ | $T_E$ | | 55 |
| | | | | $C_S$ | $U_S$ | $A_E$ | $A_E$ | $U_S$ | $A_S$ | $A_E$ | $G_E$ | $C_S$ | | | |
| | | | | | $U_S$ | $A_E$ | $A_E$ | $U_S$ | $A_S$ | $A_E$ | $G_E$ | $C_S$ | $T_E$ | | |
| | | | | | $U_S$ | $A_E$ | $A_E$ | $U_S$ | $A_S$ | $A_E$ | $G_E$ | $C_S$ | | | |
| | | | | | | $A_E$ | $A_E$ | $U_S$ | $A_S$ | $A_E$ | $G_E$ | $C_S$ | $T_E$ | | |

TABLE 3D

Metabolic products of compound # 36039

| 5'<br>N1 | N2 | N3 | N4 | N5 | N6 | N7 | N8 | N9 | N10 | N11 | N12 | N13 | N14 | N15 | N16 | N17 | N18 | 3'<br>N19 | SEQ ID NO |
|---|---|---|---|---|---|---|---|---|---|---|---|---|---|---|---|---|---|---|---|
| $A_E$ | $C_S$ | $A_E$ | $T_E$ | $C_S$ | $A_E$ | $G_E$ | $T_E$ | $C_S$ | T | G | A | $U_S$ | A | A | G | $C_S$ | T | $A_S$ | 3 |
|  | $C_S$ | $A_E$ | $T_E$ | $C_S$ | $A_E$ | $G_E$ | $T_E$ | $C_S$ | T | G | A | $U_S$ | A | A | G | $C_S$ | T | $A_S$ | 9 |
|  |  | $A_E$ | $T_E$ | $C_S$ | $A_E$ | $G_E$ | $T_E$ | $C_S$ | T | G | A | $U_S$ | A | A | G | $C_S$ | T | $A_S$ | 17 |
|  |  |  | $T_E$ | $C_S$ | $A_E$ | $G_E$ | $T_E$ | $C_S$ | T | G | A | $U_S$ | A | A | G | $C_S$ | T | $A_S$ | 18 |
|  |  |  |  | $C_S$ | $A_E$ | $G_E$ | $T_E$ | $C_S$ | T | G | A | $U_S$ | A | A | G | $C_S$ | T | $A_S$ | 19 |
|  |  |  |  |  | $A_E$ | $G_E$ | $T_E$ | $C_S$ | T | G | A | $U_S$ | A | A | G | $C_S$ | T | $A_S$ | 20 |
|  |  |  |  |  |  | $G_E$ | $T_E$ | $C_S$ | T | G | A | $U_S$ | A | A | G | $C_S$ | T | $A_S$ | 21 |
|  |  |  |  |  |  |  | $T_E$ | $C_S$ | T | G | A | $U_S$ | A | A | G | $C_S$ | T | $A_S$ | 22 |
|  |  |  |  |  |  |  |  | $C_S$ | T | G | A | $U_S$ | A | A | G | $C_S$ | T | $A_S$ | 23 |
|  |  |  |  |  |  |  |  |  | T | G | A | $U_S$ | A | A | G | $C_S$ | T | $A_S$ | 24 |
|  |  |  |  |  |  |  |  |  |  | G | A | $U_S$ | A | A | G | $C_S$ | T | $A_S$ |  |
|  |  |  |  |  |  |  |  |  |  |  | A | $U_S$ | A | A | G | $C_S$ | T | $A_S$ |  |
| $A_E$ | $C_S$ | $A_E$ | $T_E$ | $C_S$ | $A_E$ | $G_E$ | $T_E$ | $C_S$ | T | G | A | $U_S$ | A | A | G | $C_S$ | T |  | 25 |
| $A_E$ | $C_S$ | $A_E$ | $T_E$ | $C_S$ | $A_E$ | $G_E$ | $T_E$ | $C_S$ | T | G | A | $U_S$ | A | A | G | $C_S$ |  |  | 26 |
|  | $C_S$ | $A_E$ | $T_E$ | $C_S$ | $A_E$ | $G_E$ | $T_E$ | $C_S$ | T | G | A | $U_S$ | A | A | G | $C_S$ | T |  | 27 |
|  | $C_S$ | $A_E$ | $T_E$ | $C_S$ | $A_E$ | $G_E$ | $T_E$ | $C_S$ | T | G | A | $U_S$ | A | A | G | $C_S$ |  |  | 28 |
|  |  | $A_E$ | $T_E$ | $C_S$ | $A_E$ | $G_E$ | $T_E$ | $C_S$ | T | G | A | $U_S$ | A | A | G | $C_S$ | T |  | 29 |
|  |  | $A_E$ | $T_E$ | $C_S$ | $A_E$ | $G_E$ | $T_E$ | $C_S$ | T | G | A | $U_S$ | A | A | G | $C_S$ |  |  | 30 |
|  |  |  | $T_E$ | $C_S$ | $A_E$ | $G_E$ | $T_E$ | $C_S$ | T | G | A | $U_S$ | A | A | G | $C_S$ | T |  | 31 |
|  |  |  | $T_E$ | $C_S$ | $A_E$ | $G_E$ | $T_E$ | $C_S$ | T | G | A | $U_S$ | A | A | G | $C_S$ |  |  | 32 |
|  |  |  |  | $C_S$ | $A_E$ | $G_E$ | $T_E$ | $C_S$ | T | G | A | $U_S$ | A | A | G | $C_S$ | T |  | 33 |
|  |  |  |  | $C_S$ | $A_E$ | $G_E$ | $T_E$ | $C_S$ | T | G | A | $U_S$ | A | A | G | $C_S$ |  |  | 34 |
|  |  |  |  |  | $A_E$ | $G_E$ | $T_E$ | $C_S$ | T | G | A | $U_S$ | A | A | G | $C_S$ | T |  | 35 |
|  |  |  |  |  | $A_E$ | $G_E$ | $T_E$ | $C_S$ | T | G | A | $U_S$ | A | A | G | $C_S$ |  |  | 36 |
|  |  |  |  |  |  | $G_E$ | $T_E$ | $C_S$ | T | G | A | $U_S$ | A | A | G | $C_S$ | T |  | 37 |
|  |  |  |  |  |  | $G_E$ | $T_E$ | $C_S$ | T | G | A | $U_S$ | A | A | G | $C_S$ |  |  | 38 |
|  |  |  |  |  |  |  | $T_E$ | $C_S$ | T | G | A | $U_S$ | A | A | G | $C_S$ | T |  | 39 |
|  |  |  |  |  |  |  | $T_E$ | $C_S$ | T | G | A | $U_S$ | A | A | G | $C_S$ |  |  | 40 |
|  |  |  |  |  |  |  |  | $C_S$ | T | G | A | $U_S$ | A | A | G | $C_S$ | T |  | 41 |
|  |  |  |  |  |  |  |  | $C_S$ | T | G | A | $U_S$ | A | A | G | $C_S$ |  |  |  |
|  |  |  |  |  |  |  |  |  | T | G | A | $U_S$ | A | A | G | $C_S$ | T |  |  |
|  |  |  |  |  |  |  |  |  | T | G | A | $U_S$ | A | A | G | $C_S$ |  |  |  |
|  |  |  |  |  |  |  |  |  |  | G | A | $U_S$ | A | A | G | $C_S$ | T |  |  |

TABLE 3E

Metabolic products of compound # 36731

| 5'<br>$N_1$ | $N_2$ | $N_3$ | $N_4$ | $N_5$ | $N_6$ | $N_7$ | $N_8$ | $N_9$ | $N_{10}$ | $N_{11}$ | $N_{12}$ | $N_{13}$ | $N_{14}$ | $N_{15}$ | $N_{16}$ | $N_{17}$ | $N_{18}$ | 3'<br>$N_{19}$ | SEQ ID NO |
|---|---|---|---|---|---|---|---|---|---|---|---|---|---|---|---|---|---|---|---|
| $A_E$ | $C_S$ | $A_E$ | $T_E$ | $C_S$ | $A_E$ | $G_E$ | $T_E$ | $C_S$ | T | G | A | $U_S$ | A | A | G | $C_S$ | $U_S$ | $A_S$ | 3 |
|  | $C_S$ | $A_E$ | $T_E$ | $C_S$ | $A_E$ | $G_E$ | $T_E$ | $C_S$ | T | G | A | $U_S$ | A | A | G | $C_S$ | $U_S$ | $A_S$ | 9 |
|  |  | $A_E$ | $T_E$ | $C_S$ | $A_E$ | $G_E$ | $T_E$ | $C_S$ | T | G | A | $U_S$ | A | A | G | $C_S$ | $U_S$ | $A_S$ | 17 |
|  |  |  | $T_E$ | $C_S$ | $A_E$ | $G_E$ | $T_E$ | $C_S$ | T | G | A | $U_S$ | A | A | G | $C_S$ | $U_S$ | $A_S$ | 18 |
|  |  |  |  | $C_S$ | $A_E$ | $G_E$ | $T_E$ | $C_S$ | T | G | A | $U_S$ | A | A | G | $C_S$ | $U_S$ | $A_S$ | 19 |
|  |  |  |  |  | $A_E$ | $G_E$ | $T_E$ | $C_S$ | T | G | A | $U_S$ | A | A | G | $C_S$ | $U_S$ | $A_S$ | 20 |
|  |  |  |  |  |  | $G_E$ | $T_E$ | $C_S$ | T | G | A | $U_S$ | A | A | G | $C_S$ | $U_S$ | $A_S$ | 21 |
|  |  |  |  |  |  |  | $T_E$ | $C_S$ | T | G | A | $U_S$ | A | A | G | $C_S$ | $U_S$ | $A_S$ | 22 |
|  |  |  |  |  |  |  |  | $C_S$ | T | G | A | $U_S$ | A | A | G | $C_S$ | $U_S$ | $A_S$ | 23 |
|  |  |  |  |  |  |  |  |  | T | G | A | $U_S$ | A | A | G | $C_S$ | $U_S$ | $A_S$ | 24 |
|  |  |  |  |  |  |  |  |  |  | G | A | $U_S$ | A | A | G | $C_S$ | $U_S$ | $A_S$ |  |
|  |  |  |  |  |  |  |  |  |  |  | A | $U_S$ | A | A | G | $C_S$ | $U_S$ | $A_S$ |  |
| $A_E$ | $C_S$ | $A_E$ | $T_E$ | $C_S$ | $A_E$ | $G_E$ | $T_E$ | $C_S$ | T | G | A | $U_S$ | A | A | G | $C_S$ | $U_S$ |  | 25 |
| $A_E$ | $C_S$ | $A_E$ | $T_E$ | $C_S$ | $A_E$ | $G_E$ | $T_E$ | $C_S$ | T | G | A | $U_S$ | A | A | G | $C_S$ |  |  | 26 |
|  | $C_S$ | $A_E$ | $T_E$ | $C_S$ | $A_E$ | $G_E$ | $T_E$ | $C_S$ | T | G | A | $U_S$ | A | A | G | $C_S$ | $U_S$ |  | 27 |
|  | $C_S$ | $A_E$ | $T_E$ | $C_S$ | $A_E$ | $G_E$ | $T_E$ | $C_S$ | T | G | A | $U_S$ | A | A | G | $C_S$ |  |  | 28 |
|  |  | $A_E$ | $T_E$ | $C_S$ | $A_E$ | $G_E$ | $T_E$ | $C_S$ | T | G | A | $U_S$ | A | A | G | $C_S$ | $U_S$ |  | 29 |
|  |  | $A_E$ | $T_E$ | $C_S$ | $A_E$ | $G_E$ | $T_E$ | $C_S$ | T | G | A | $U_S$ | A | A | G | $C_S$ |  |  | 30 |
|  |  |  | $T_E$ | $C_S$ | $A_E$ | $G_E$ | $T_E$ | $C_S$ | T | G | A | $U_S$ | A | A | G | $C_S$ | $U_S$ |  | 31 |
|  |  |  | $T_E$ | $C_S$ | $A_E$ | $G_E$ | $T_E$ | $C_S$ | T | G | A | $U_S$ | A | A | G | $C_S$ |  |  | 32 |
|  |  |  |  | $C_S$ | $A_E$ | $G_E$ | $T_E$ | $C_S$ | T | G | A | $U_S$ | A | A | G | $C_S$ | $U_S$ |  | 33 |
|  |  |  |  | $C_S$ | $A_E$ | $G_E$ | $T_E$ | $C_S$ | T | G | A | $U_S$ | A | A | G | $C_S$ |  |  | 34 |
|  |  |  |  |  | $A_E$ | $G_E$ | $T_E$ | $C_S$ | T | G | A | $U_S$ | A | A | G | $C_S$ | $U_S$ |  | 35 |
|  |  |  |  |  | $A_E$ | $G_E$ | $T_E$ | $C_S$ | T | G | A | $U_S$ | A | A | G | $C_S$ |  |  | 36 |
|  |  |  |  |  |  | $G_E$ | $T_E$ | $C_S$ | T | G | A | $U_S$ | A | A | G | $C_S$ | $U_S$ |  | 37 |
|  |  |  |  |  |  | $G_E$ | $T_E$ | $C_S$ | T | G | A | $U_S$ | A | A | G | $C_S$ |  |  | 38 |
|  |  |  |  |  |  |  | $T_E$ | $C_S$ | T | G | A | $U_S$ | A | A | G | $C_S$ | $U_S$ |  | 39 |
|  |  |  |  |  |  |  | $T_E$ | $C_S$ | T | G | A | $U_S$ | A | A | G | $C_S$ |  |  | 40 |
|  |  |  |  |  |  |  |  | $C_S$ | T | G | A | $U_S$ | A | A | G | $C_S$ | $U_S$ |  | 41 |
|  |  |  |  |  |  |  |  | $C_S$ | T | G | A | $U_S$ | A | A | G | $C_S$ |  |  |  |
|  |  |  |  |  |  |  |  |  | T | G | A | $U_S$ | A | A | G | $C_S$ | $U_S$ |  |  |
|  |  |  |  |  |  |  |  |  | T | G | A | $U_S$ | A | A | G | $C_S$ |  |  |  |
|  |  |  |  |  |  |  |  |  |  | G | A | $U_S$ | A | A | G | $C_S$ | $U_S$ |  |  |

In certain embodiments, a modified oligonucleotide consists of greater than 19 linked nucleosides, and comprises a nucleoside pattern described herein. The nucleosides that are present in addition to the nucleosides described by the nucleoside pattern are either modified or unmodified. For example, a modified oligonucleotide consisting of 21 linked nucleosides and having a nucleobase sequence complementary to miR-21 may have nucleoside pattern IV, V, or VII, which is 19 linked nucleosides in length, or may have nucleoside pattern VI, which is 15 nucleosides in length, or may have nucleoside pattern III, which may be 19 to 22 nucleosides in length. The additional nucleosides may be comprised of modified or unmodified sugar moieties. In certain embodiments, a modified oligonucleotide consists of 19 linked nucleosides and comprises any of the nucleoside patterns described herein. In certain embodiments, a modified oligonucleotide consists of 20 linked nucleosides and comprises any of the nucleoside patterns described herein. In certain embodiments, a modified oligonucleotide consists of 21 linked nucleosides and comprises any of the nucleoside patterns described herein. In certain embodiments, a modified oligonucleotide consists of 22 linked nucleosides and comprises any of the nucleoside patterns described herein. In certain embodiments, a modified oligonucleotide consists of 23 linked nucleosides and comprises any of the nucleoside patterns described herein. In certain embodiments, a modified oligonucleotide consists of 24 linked nucleosides and comprises any of the nucleoside patterns described herein. In certain embodiments, a modified oligonucleotide consists of 25 linked nucleosides and comprises any of the nucleoside patterns described herein.

Certain Uses of the Invention

Modulation of miR-21 Activity

The compounds provided herein are potent and specific inhibitors of miR-21 activity, and are thus useful for modulating miR-21 activity.

MicroRNAs bind to and repress the expression of messenger RNAs. In certain instances, inhibiting the activity of a microRNA leads to de-repression of the messenger RNA, i.e. the messenger RNA expression is increased at the level of RNA and/or protein. Provided herein are methods for modulating the expression of a miR-21-regulated transcript, comprising contacting a cell with a compound of the invention, wherein the compound comprises a modified oligonucleotide having a sequence complementary to a miR-21.

In certain embodiments, a miR-21-regulated transcript is YOD1, and inhibition of miR-21 results in an increase in the level of YOD1 mRNA. In certain embodiments, a miR-21 regulated transcript is PPAR-alpha, and inhibition of miR-21 results in an increase in the level of PPAR-alpha mRNA. In certain embodiments, a miR-21-regulated transcript is RNF167.

In certain embodiments, a miR-21-regulated transcript is SPG20. In certain embodiments, inhibition of miR-21 in the liver results in an increase in the level of SPG20 mRNA.

In certain embodiments, following contacting a cell with a compound of the invention, an at least 1.5-fold increase in the mRNA level of a miR-21-regulated transcript is observed. In certain embodiments, following contacting a cell with a compound of the invention, an at least 2.0-fold increase in the mRNA level of a miR-21-regulated transcript is observed. In certain embodiments, the mRNA level of the microRNA-regulated transcript increases at least 2.5-fold. In certain embodiments, the mRNA level of the microRNA-regulated transcript increases at least 3.0-fold. In certain embodiments, the mRNA level of the microRNA-regulated transcript increases at least 3.5-fold. In certain embodiments, the mRNA level of the microRNA-regulated transcript increases at least 4.0-fold. In certain embodiments, the mRNA level of the microRNA-regulated transcript increases at least 4.5-fold. In certain embodiments, the mRNA level of the microRNA-regulated transcript increases at least 5.0-fold.

Certain microRNAs are known to target several messenger RNAs, in some cases hundreds of messenger RNAs. Inhibiting the activity of a single microRNA can lead to detectable changes in expression of many of the microRNAs targets. Provided herein are methods for modulating multiple miR-21-regulated transcripts, comprising inhibiting the activity of miR-21, wherein broad gene expression changes occur.

In certain embodiments, phenotypic changes may be observed following inhibition of a miR-21 with a compound of the invention. Such phenotypic changes may occur with or without detectable changes in the expression of a miR-21-regulated transcript.

Diseases and Disorders

A normal physiological response to damage or injury in an organ or tissue involves repair of the damaged tissue, which is a fundamental biological process necessary for survival. During the repair process, after foreign materials, bacteria, and damaged tissue are eliminated, fibroblasts migrate in to the site of injury to deposit new extracellular matrix, which then becomes structurally organized as part of the tissue remodeling phase.

Fibroblasts are the most common cells found in connective tissue, and are responsible for the synthesis of reticulin and other elastic fibres which support the extracellular matrix and play an important part in normal wound healing (Sempowski, G. D. et al., 2002. Wound Repair Regeneration. 3: 120-131). Fibroblasts are responsible for the deposition of collagen, which is necessary to repair injured tissue and restore its structure and function. During the wound-healing process, activated fibroblasts are transformed into myofibroblasts, which are collagen-secreting alpha-SMA+ fibroblasts. In the initial stages of the wound-healing process, myofibroblasts produce matrix metalloproteases, which disrupt the basement membrane and permit inflammatory cells to be efficiently recruited to the site of injury. During the later stages of injury repair, myofibroblasts promote wound contraction, the process by which the edges of the wound migrate toward the center of the wound. Thus, fibroblast activity is essential to the normal healing process.

Fibroblasts that participate in the normal injury repair process may be derived from local mesenchymal cells, recruited from the bone marrow, or derived by epithelial-mesenchymal transition. Epithelial-mesenchymal transition (EMT) describes a series of rapid changes of cell phenotype (Kalluri, R. and Neilson, E. G. 2003. J. Clin. Invest. 112: 1776-1784) during which static epithelial cells lose cell-cell contacts, acquire mesenchymal features and manifest a migratory phenotype. Resident fibroblasts, infiltrating fibrocytes or pericyte-like cells may also participate in the injury repair process.

Under some conditions, the tissue repair process occurs in excess, resulting an excessive accumulation of extracellular matrix (ECM) components and substantial remodeling of the ECM, which contribute to the formation of a permanent fibrotic scar. The formation of this excess fibrous connective tissue, a process known as fibrosis, contributes to abnormal changes in tissue architecture and interferes with normal organ function.

Fibrosis can occur in any part of the body, and can result from a variety of physical, metabolic, ischemic, infectious, inflammatory or immunological injuries. Although the anatomical locations, origins, and clinical manifestations of fibrosis may be diverse, there are important pathological features common to all types of fibrosis. Regardless of the location in which fibrosis occurs, the fibrotic process involves the secretion and activation of profibrotic cytokines, the expansion and activation of mesenchymal cell populations, and extracellular matrix synthesis and organization, and ultimately leads to the destruction of normal tissue. Left untreated, fibrosis can lead to a variety of conditions of the heart, lungs, kidney, liver, eye, and skin, among other tissues.

As demonstrated herein, the inhibition of miR-21 in a model of fibrosis led to decreased collagen deposition.

Accordingly, provided herein are methods for treating, preventing, and/or delaying the onset of fibrosis, comprising administering a compound comprising a modified oligonucleotide, wherein the modified oligonucleotide is complementary to miR-21, to a subject. Also provided herein are compositions for treating, preventing, and/or delaying the onset of fibrosis, comprising a compound comprising a modified oligonucleotide, wherein the modified oligonucleotide is complementary to miR-21, to a subject. The subject may have received a diagnosis of fibrosis, may be at risk for developing fibrosis, or may be suspected of having fibrosis.

In certain embodiments, a subject having fibrosis has kidney fibrosis, lung fibrosis, liver fibrosis, cardiac fibrosis, skin fibrosis, age-related fibrosis, spleen fibrosis, scleroderma, or post-transplant fibrosis.

Many diseases or abnormalities of the kidney are characterized by the presence of fibrosis. As such, the compounds provided herein are useful for treating, ameliorating, preventing, and/or delaying the onset of any kidney disease that is characterized by the presence of fibrosis. In certain embodiments, a subject having fibrosis has a kidney disease or condition. In certain embodiments, a subject at risk for developing fibrosis has a kidney disease or condition. In certain embodiments, a subject suspected of having fibrosis has a kidney disease or condition. Accordingly, provided herein are methods for treating a subject having, at risk for developing, or suspected of having fibrosis, wherein the subject has a kidney disease or condition. The kidney disease or condition may be one or more of, without limitation, glomerular disease, tubulointerstitial fibrosis, IgA nephropathy, interstitial fibrosis/tubular atrophy, glomerulosclerosis, glomerulonephritis, Alport Syndrome, diabetes mellitus, idiopathic focal segmental glomerulosclerosis, membranous nephropathy, collapsing glomerulopathy, chronic recurrent kidney infection, diabetes mellitus, diabetic nephropathy, chronic recurrent kidney infection, hypertension, systemic hypertension, intraglomerular hypertension, or end stage renal disease.

Provided herein are methods for improving kidney function in a subject. In certain embodiments, provided herein are methods for delaying and/or preventing the onset of end stage renal disease. In certain embodiments, provided herein are methods for delaying the need for dialysis in a subject. In certain embodiments, provided herein are methods for delaying the need for renal transplant in a subject. In certain embodiments, provided herein are methods for delaying impaired kidney function in a subject.

Chronic kidney disease may be characterized by the presence of fibrosis. Accordingly, in certain embodiments, the kidney disease or condition is chronic kidney disease. In certain embodiments, the subject is at risk for developing chronic kidney disease. In certain embodiments, a subject having acute kidney injury is at risk for developing fibrosis and/or chronic kidney disease. Accordingly, the compositions and methods provided herein may be administered to a subject having acute kidney injury, to prevent or delay the onset of fibrosis and/or chronic kidney disease.

In certain embodiments, a subject having fibrosis has kidney fibrosis that results from acute or repetitive trauma to the kidney. The trauma may result from surgery, chemotherapy, radiation treatment, allograft rejection, chronic transplant rejection, and acute transplant rejection.

In certain embodiments, kidney fibrosis may result from exposure to any agent that may be nephrotoxic after acute or chronic exposure. Such agents include pharmaceutical agents, including but not limited to analgesics, non-steroidal anti-inflammatory drugs, antibiotics, lithium, cyclosporine, mesalazine, contrast media, chemotherapeutic agents; occupational toxins, including but not limited to heavy metals; and environmental toxins, including but not limited to heavy metals (e.g. cadmium, mercuric chloride) or plant nephrotoxins (e.g. aristolochic acid).

Provided herein are methods for the treatment of Alport Syndrome, comprising administering to a subject having or suspected of having Alport Syndrome a modified oligonucleotide complementary to miR-21. In certain embodiments, the subject has been diagnosed as having Alport Syndrome prior to administration of the modified oligonucleotide. Diagnosis of Alport Syndrome may be achieved through evaluation of parameters including, without limitation, a subject's family history, clinical features (including without limitation proteinuria, albuminuria, hematuria, impaired GFR, deafness and/or ocular changes) and results of tissue biopsies. Kidney biopsies may be tested for the presence or absence of the type IV collagen alpha-3, alpha-4, and alpha-5 chains. Additionally, structural changes in the glomerulus can be detected by electron microscopy of kidney biopsy material. A skin biopsy may be tested for the presence of the type IV collagen alpha-5 chain, which is normally present in skin and is usually absent from male subjects with the X-linked form of Alport Syndrome. Diagnosis of Alport Syndrome may also include screening for mutations in one or more of the Col4a3, Col4a4, or Col4a5 genes.

In certain embodiments, levels of miR-21 are increased in the kidney of a subject having Alport Syndrome. In certain embodiments, prior to administration, a subject is determined to have an increased level of miR-21 in the kidney. miR-21 levels may be measured from kidney biopsy material.

Many diseases or abnormalities of the liver are characterized by the presence of fibrosis. As such, in certain embodiments, a subject having fibrosis has a liver disease or condition. In certain embodiments, a subject at risk for developing fibrosis has a liver disease or condition. In certain embodiments, a subject suspected of having fibrosis has a liver disease or condition. Accordingly, provided herein are methods for treating a subject having, at risk for developing, or suspected of having fibrosis, wherein the subject has a liver disease or condition. In certain embodiments, a liver disease or condition may be one or more of, without limitation, chronic liver injury, hepatitis virus infection (including hepatitis C virus infection and hepatitis B virus infection), non-alcoholic fatty liver disease (NAFLD), non-alcoholic steatohepatitis (NASH), alcoholic liver disease (ALD), alcoholic steatohepatitis, bridging fibrosis, or cirrhosis. In certain embodiments a liver disease or condition is associated with exposure to toxic chemicals. In certain embodiments, a liver disease or condition results from exposure to pharmaceutical agents, e.g. acetaminophen. In certain embodiments, a subject receiving chemotherapy is at risk for liver fibrosis and/or chronic liver injury.

The presence or degree of fibrosis may be detected by needle liver biopsy or through a non-invasive transient elastography method that evaluates the degree of liver stiffness, such as the FibroScan® method.

Fibrosis may be present in many diseases or abnormalities of the lung. As such, in certain embodiments, a subject having fibrosis has a lung disease or condition. In certain embodiments, a subject at risk for developing fibrosis has a lung disease or condition. In certain embodiments, a subject suspected of having fibrosis has a lung disease or condition. Accordingly, provided herein are methods for treating a subject having, at risk for developing, or suspected of having fibrosis, wherein the subject has a lung disease or condition. In certain embodiments, a lung disease or condition may be one or more of, without limitation, lung fibrosis, idiopathic pulmonary fibrosis, or chronic obstructive lung disease. In certain embodiments, lung fibrosis may result from inhalation of particulate matter, such as those found in silica gel, asbestos, air pollutants or cigarette smoke.

In certain embodiments the fibrosis is cardiac fibrosis.

In certain embodiments the fibrosis is skin fibrosis. In certain embodiments the fibrosis is age-related fibrosis. In certain embodiments the fibrosis is spleen fibrosis.

Scleroderma is a chronic autoimmune disease characterized by fibrosis, among other symptoms. In certain embodiments, a subject having fibrosis has scleroderma. In certain embodiments, a subject having scleroderma has fibrosis in internal organs, in addition to fibrosis of the skin.

Fibrosis frequently occurs in transplanted organs, leading to loss of organ function and ultimately to chronic rejection of the transplanted organ. Prevention or treatment of fibrosis in transplanted organs may prevent or delay chronic rejection of the transplanted organ, or in other words may prolong function of the transplanted organ. Accordingly, in certain embodiments a subject has post-transplant fibrosis. In certain embodiments, the post-transplant fibrosis is kidney post-transplant fibrosis. In certain embodiments, the transplantation associated fibrosis is liver post-transplant fibrosis. In certain embodiments, a compound described herein is administered prior to transplantation. In certain embodiments, a compound described herein is administered concurrently with transplantation. In certain embodiments, a compound described herein is administered following transplantation.

Provided herein are methods for treating a subject having a fibroproliferative disorder. In certain embodiments such methods comprise administering to a subject having or suspected of having a fibroproliferative disorder a modified oligonucleotide having a nucleobase sequence which is complementary to a miRNA or a precursor thereof. In certain embodiments, the miRNA is miR-21.

Cancer and Metastasis

Abnormally high expression of miR-21 has been demonstrated in numerous types of cancer. Further, inhibition of miR-21 in in vitro and in vivo models has demonstrated that inhibitors of miR-21 are useful for the inhibition of cellular processes that support cancer cell growth, as well as for the treatment of cancer.

Accordingly, in certain embodiments, the compounds provided herein are used for treating, preventing, ameliorating, and/or delaying the onset of cancer. In certain embodiments, the cancer is liver cancer, breast cancer, bladder cancer, prostate cancer, bone cancer, colon cancer, lung cancer, brain cancer, hematological cancer, pancreatic cancer, head and neck cancer, cancer of the tongue, stomach cancer, skin cancer, thyroid cancer, neuroblastoma, esophageal cancer, mesothelioma, neuroblastoma, kidney cancer, testicular cancer, rectal cancer, cervical cancer, or ovarian cancer. In certain embodiments, the liver cancer is hepatocellular carcinoma. In certain embodiments, the liver cancer is due to metastasis of cancer that originated in another part of the body, for example a cancer that is due to metastasis of bone cancer, colon cancer or breast cancer. In certain embodiments, the brain cancer is glioblastoma multiforme, oligoastrocytoma, or oligodendroglioma. In certain embodiments, the glioblastoma multiforme is proneural glioblastoma multiforme, neural glioblastoma multiforme, classical glioblastoma multiforme, or mesenchymal glioblastoma multiforme. In certain embodiments, In certain embodiments, the hematological cancer is acute myelogenous leukemia, acute lymphocytic leukemia, acute monocytic leukemia, multiple myeloma, chronic lymphotic leukemia, chronic myeloid leukemia, hodgkin's lymphoma, or non-hodgkin's lymphoma. In certain embodiments, the skin cancer is melanoma. In certain embodiments, the kidney cancer is renal cell carcinoma. In certain embodiments, the breast cancer is ductal cell carcinoma in situ, invasive ductal cell carcinoma, triple negative breast cancer, medullary carcinoma, tubular carcinoma, and mucinous carcinoma. In certain embodiments, the cancer is resistant to chemotherapy.

In certain embodiments, in liver cancer, miR-21 is elevated and the level of one or more miR-21-regulated transcripts is reduced. In certain embodiments, the reduced miR-21-regulated transcript is SPG20.

In certain embodiments, the liver cancer is hepatocellular carcinoma (HCC). The diagnosis of hepatocellular carcinoma is typically made by liver imaging tests such as abdominal ultrasound, helical computed tomography (CT) scan or triple phase CT scan. Such imaging tests may be performed in conjunction with measurement of blood levels of alpha-fetoprotein and/or blood levels of des-gamma-carboxyprothrombin. In certain subjects, MRI may be used in place of CT scan. The liver imaging tests allow the assessment of the tumor size, number, location, metastasis outside the liver, patency and or invasion of the arteries and veins of the liver by the tumor. This assessment aids the decision as to the mode of therapeutic or palliative intervention that is appropriate. The final diagnosis is typically confirmed by needle biopsy and histopathological examination.

Accordingly, in certain embodiments, the liver cancer is detected following a computed tomography (CT) scan that detects tumors. In certain embodiments, the liver cancer is detected following magnetic resonance imaging (MRI). In certain embodiments, HCC is characterized as a single primary tumor. In certain embodiments, HCC is characterized as multiple primary tumors. In certain embodiments, HCC is characterized as a poorly defined primary tumor with an infiltrative growth pattern. In certain embodiments, the HCC is a single primary tumor with vascular invasion. In certain embodiments, the HCC is characterized as multiple primary tumors with vascular invasion. In certain embodiments, the HCC has metastasized to one or more lymph nodes. In certain such embodiments, the lymph nodes are regional lymph nodes. In certain embodiments, the HCC has metastasized to one or more distant tissues. In certain embodiments, the HCC has metastasized to other regions of the liver, the portal vein, lymph nodes, adrenal glands, bone or lungs. In certain embodiments, fibrosis is present.

A number of systems have been employed to predict the prognosis for HCC, including the TNM system, the Okuda system, the Barcelona Clinic Liver Cancer (BCLC) and the CLIP score. Each of these systems incorporates four features that have been recognized as being important determinants of survival: the severity of underlying liver disease, the size of the tumor, extension of the tumor into adjacent structures, and the presence of metastases. The TNM system classifies HCC as stage I, II, III, IV, or V. The BCLC classifies HCC as Stage A1, A2, A3, A4, B, C, and D, and includes consideration of a Child-Pugh score.

In certain embodiments, liver cancer is classified as Stage 1, Stage 2, Stage 3A, Stage 3B, Stage 3C, or Stage 4. Stage 1 is characterized by a cancer is no bigger than 2 cm in size and that has not begun to spread. At Stage 2, the cancer is affecting blood vessels in the liver, or there is more than one tumor in the liver. At Stage 3A, the cancer is bigger than 5 cm in size or has spread to the blood vessels near the liver. At Stage 3B, the cancer has spread to nearby organs, such as the bowel or the stomach, but has not spread to the lymph nodes. At Stage 3C the cancer can be of any size and has spread to nearby lymph nodes. At Stage 4 the cancer has spread to parts of the body further away from the liver, such as the lungs.

Biomarkers in a subject's blood may be used to augment a diagnosis of liver cancer, stage a liver cancer, or develop a prognosis for survival. Such biomarkers include blood tumor biomarkers, such as alpha-fetoprotein and des-gamma carboxyprothrombin. In certain such embodiments, the subject has elevated blood alpha-fetoprotein. In certain such embodiments, the subject has elevated blood des-gamma carboxyprothrombin.

A subject having liver cancer may also suffer from abnormal liver function. Liver function may be assessed by liver function tests, which measure, among other things, blood levels of liver transaminases. In certain embodiments, a subject having abnormal liver function has elevated blood liver transaminases. Blood liver transaminases include alanine aminotransferase (ALT) and aspartate aminotransferase (AST). In certain embodiments, a subject having abnormal liver function has elevated blood bilirubin. In certain embodiments, a subject has abnormal blood albumin levels.

In certain embodiments, a subject's liver function is assessed by the Child-Pugh classification system, which defines three classes of liver function. In this classification system, points are assigned to measurements in one of five categories: bilirubin levels, albumin levels, prothrombin time, ascites, and encephalopathy. One point is assigned per each of the following characteristics present: blood bilirubin of less than 2.0 mg/dl; blood albumin of greater than 3.5 mg/dl; a prothrombin time of less than 1.7 international normalized ratio (INR); ascites is absent; or encephalopathy is absent. Two points are assigned per each of the following characteristics present: blood bilirubin of 2-3 mg/dl; blood bilirubin of 3.5 to 2.8 mg/dl; prothrombin time of 1.7-2.3 INR; ascites is mild to moderate; or encephalopathy is mild. Three points are assigned per each of the following characteristics present: bilirubin of greater than 3.0 mg/dl; blood albumin of less than 2.8 mg/dl; prothrombin time of greater than 2.3 INR; ascites is severe to refractory; or encephalopathy is severe. The scores are added and Class A is assigned for a score of 5-6 points, Class B is assigned for a score of 7-9 points, and Class C is assigned for a score of 10-15 points, A subject having liver cancer may have previously suffered from, or may currently suffer from, chronic hepatitis C infection, chronic hepatitis B infection, non-alcoholic fatty liver disease, or cirrhosis. Subjects having liver cancer accompanied by and/or resulting from hepatitis C infection, hepatitis B infection, non-alcoholic fatty liver disease, or cirrhosis may be treated by the methods described herein.

A subject's response to treatment may be evaluated by tests similar to those used to diagnosis the liver cancer, including, without limitation, CT scan, MRI, and needle biopsy. Response to treatment may also be assessed by measuring biomarkers in blood, for comparison to pre-treatment levels of biomarkers.

miR-21 has also been linked to the process of metastasis. While epithelial-mesenchymal transition (EMT) occurs in normal physiological processes, EMT has been connected to the process of metastasis. The relevance of EMT in tumor progression has been explored in several studies (Greenburg, G. and Hay, E. 1986. Dev. Biol. 115: 363-379; Boyer, B. et al., 1989. J. Cell. Biol. 109: 1495-1509; Uehara, Y. et al., 1992. J. Cell. Biol. 117: 889-894). Epithelial cells are held together through integrins to an underlying extracellular matrix (ECM) called the basement membrane. Mesenchymal cells, on the other hand, have the ability to invade and move through the three-dimensional structure of the ECM. Therefore, EMT at least superficially resembles the transformation of normal adherent cells into the metastatic phenotype.

Provided herein are methods for treating, preventing, ameliorating, and/or delaying the onset of metastasis. The metastasis may result from the migration of cancer cells from any primary site of cancer to any secondary site of cancer.

Acute Kidney Injury

Acute kidney injury is a rapid loss of kidney function, which may be brought on by a number of causes, including low blood volume, exposure to toxins, and urinary obstruction. Acute kidney injury may progress to fibrosis and/or chronic kidney disease. Elevated miR-21 has been observed in a model of acute kidney injury. Accordingly, in certain embodiments, the compounds provided herein are used for treating, preventing, ameliorating, and/or delaying fibrosis that occurs as a result of acute kidney injury. In certain embodiments, acute kidney injury may be the result of exposure to toxic substances, such as environmental toxins or cancer therapeutic agents. Acute kidney injury may arise from damage to the kidney itself, for example in conditions such as glomerulonephritis, acute tubular necrosis, and acute interstitial nephritis. In certain embodiments, acute kidney injury is caused by urinary tract obstruction, such as that related to benign prostatic hyperplasia, kidney stones, obstructed urinary catheter, bladder stone, bladder, ureteral or renal malignancy. In some embodiments, the compounds provided herein are administered to a subject to enhance recovery from acute kidney injury.

Cardiac Diseases

Elevated miR-21 expression has been found in human cardiac disease, and inhibition of miR-21 in relevant animal models has demonstrated improvements in cardiac fibrosis and cardiac function. Accordingly, in certain embodiments, the compounds provided herein are used for treating, preventing, ameliorating, and/or delaying the onset of one more cardiac diseases. In certain embodiments, a cardiac disease is cardiac fibrosis, cardiac enlargement, cardiac hypertrophy, cardiac dilation, hypertrophic cardiomyopathy, heart failure, post-myocardial infarction remodeling, myocardial infarction, cardiomyopathy (for example, hypertrophic cardiomyopathy, restrictive cardiomyopathy, dilated cardiomyopathy (DCM), idiopathic dilated cardiomyopathy, or dilated cardiomyopathy with arrhythmias), diastolic heart failure, chronic atrial fibrillation, primary pulmonary hypertension, acute respiratory distress syndrome, brugada syndrome, progressive cardiac conduction disease, uremic pericarditis, anthracycline cardiomyopathy, arterial fibrosis, post-radiation lymphatic fibrosis, sarcoidosis, scleroderma, endocardial fibroelastosis, serotonergic excess, cardiac valvulopathy, atrial fibrosis, atrial fibrillation, mitral valvular disease, hypertension, chronic ventricular dysfunction, pressure and volume overload, or myocardial fibrosis.

Cellular Processes

Provided herein are compositions and methods for reducing or preventing fibroblast proliferation or activation. Also provided herein are compositions and methods for inhibiting the synthesis of extracellular matrix, which includes but is not limited to the synthesis of collagen, fibronectin, collagenase, or a tissue inhibitor of metalloproteinase.

Provided herein are methods for modulating the cellular processes associated with epithelial-mesenchymal transition (EMT). Such methods comprise contacting an epithelial cell with a compound consisting of a modified oligonucleotide, wherein the modified oligonucleotide is complementary to miR-21. In certain embodiments, the contacting delays the transition of an epithelial cell to a fibroblast. In certain embodiments, the contacting prevents the transition of an epithelial cell to a fibroblast.

In certain embodiments, a compound provided herein may stop, slow, or reduce the proliferation of cancer cells. In certain embodiments, a compound provided herein may induce apoptosis in cancer cells. In certain embodiments, a compound provided herein may reduce cancer cell survival.

In certain embodiments, the epithelial cell is a cancer cell. In certain embodiments, the contacting delays the metastasis of the cancer cell. In certain embodiments, the contacting prevents metastasis of the cancer cell.

Certain Clinical Outcomes

In certain embodiments, administration of the compounds or methods provided herein result in one or more clinically desirable outcomes in a subject. Such improvements may be used to determine the extent to which a subject is responding to treatment.

In certain embodiments a clinically desirable outcome is the amelioration of fibrosis. In certain embodiments a clinically desirable outcome is the slowing of further progression of fibrosis. In certain embodiments a clinically desirable outcome is the halting of further progression of fibrosis. In certain embodiments a clinically desirable outcome is a reduction in fibrosis. In certain embodiments a clinically desirable outcome is a reduction in collagen content in the organ having fibrosis.

In certain embodiments a clinically desirable outcome is the amelioration of fibrosis in any organ or tissue. In certain embodiments a clinically desirable outcome is the slowing of further progression of fibrosis. In certain embodiments a clinically desirable outcome is the halting of further progression of fibrosis. In certain embodiments a clinically desirable outcome is a reduction in fibrosis. In certain embodiments a clinically desirable outcome is a reduction in collagen content in the affected organ.

In certain embodiments a clinically desirable outcome is improved kidney function. Kidney function may be assessed by one or more known methods commonly performed in a clinical setting, including, without limitation: measuring blood urea nitrogen in the blood of the subject; measuring creatinine in the blood of the subject; measuring creatinine clearance in the subject; measuring proteinuria in the subject; measuring albumin:creatinine ratio in the subject; measuring glomerular filtration rate in the subject; measuring urinary output in the subject; measuring inulin clearance in the urine of the subject; measuring urinary osmolarity in the subject; measuring urinary osmolality in the subject; measuring hematuria in the subject; measuring cystatin C in the blood and/or urine of the subject; measuring neutrophil gelatinase-associated lipocalin (NGAL) in the blood or urine of the subject; measuring kidney injury molecule-1 (KIM-1) mRNA levels in the urine; and/or measuring clusterin levels in the urine.

In certain embodiments, the administration improves kidney function in the subject. In certain embodiments, the administration delays time to dialysis. In certain embodiments, the administration delays time to renal transplant. In certain embodiments, the administration improves life expectancy of the subject. In certain embodiments, the administration reduces hematuria. In certain embodiments, the administration delays the onset of hematuria. In certain embodiments, the administration reduces proteinuria. In certain embodiments, the administration delays the onset of proteinuria.

In any of the embodiments provided herein, the administration of a modified oligonucleotide targeted to miR-21 improves one or more markers of kidney function in the subject. Improvements in markers of kidney function include, without limitation: reduced blood urea nitrogen in the subject; reduced creatinine in the blood of the subject; improved creatinine clearance in the subject; reduced proteinuria in the subject; reduced albumin:creatinine ratio in the subject; improved glomerular filtration rate in the subject; improved inulin clearance in the subject; reduced neutrophil gelatinase-associated lipocalin (NGAL) in the blood of the subject; reduced Cystatin C in the blood of the subject; and increased urinary output in the subject. In certain embodiments, the proteinuria is microalbuminuria. In certain embodiments, the proteinuria is macroalbuminuria.

In certain embodiments, a clinically desirable outcome is improved liver function. Liver function may be assessed by one or more known methods commonly performed in a clinical setting, including, without limitation: measuring alanine aminotransferase levels in the blood of the subject; measuring aspartate aminotransferase levels in the blood of the subject; measuring bilirubin levels in the blood of the subject; measuring albumin levels in the blood of the subject; measuring prothrombin time in the subject; measuring ascites in the subject; and/or measuring encephalopathy in the subject.

In certain embodiments a clinically desirable outcome is improved lung function in a subject having pulmonary fibrosis. In certain embodiments the subject has idiopathic pulmonary fibrosis. Lung function may be assessed by one or more known methods commonly performed in a clinical setting, including, without limitation: measuring vital capacity in the subject; measuring forced vital capacity in the subject; measuring forced expiratory volume in one second in the subject; measuring peak expiratory flow rate in the subject; measuring forced expiratory flow in the subject; measuring maximal voluntary ventilation in the subject; determining the ratio of forced expiratory volume in one second to forced vital capacity in the subject; measuring ventilation/perfusion ratio in the subject; measuring nitrogen washout in the subject; measuring absolute volume of air in one or more lungs of a subject; and administering the 6-minute walk test.

In certain embodiments a clinically desirable outcome is improved cardiac function in a subject having cardiac fibrosis. Cardiac function may be assessed by one or more known methods commonly performed in a clinical setting, including, without limitation: measuring cardiac output in the subject; measuring stroke volume in the subject; measuring mean systolic ejection rate in the subject; measuring systolic blood pressure in the subject; measuring left ventricular ejection fraction in the subject; determining stroke index in the subject; determining cardiac index in the subject; measuring left ventricular percent fractional shortening in the subject; measuring mean velocity of circumferential fiber shortening in the subject; measuring left ventricular inflow velocity pattern in the subject; measuring pulmonary venous flow velocity pattern in the subject; measuring peak early diastolic velocity of the mitral annulus of the subject.

In certain embodiments a clinically desirable outcome is reduction of tumor number and/or reduction of tumor size in a subject having cancer. In certain embodiments a clinically desirable outcome is a reduction in cancer cell number in a subject having cancer. Additional clinically desirable outcomes include the extension of overall survival time of the subject, and/or extension of progression-free survival time of the subject. In certain embodiments, administration of a compound provided herein prevents an increase in tumor size and/or tumor number. In certain embodiments, administration of a compound provided herein prevents metastatic progression. In certain embodiments, administration of a compound provided herein slows or stops metastatic progression. In certain embodiments, administration of a compound provided herein prevents the recurrence of tumors. In certain embodiments, administration of a compound provided herein prevents recurrence of tumor metastasis.

Certain desirable clinical outcomes may be assessed by measurements of blood biomarkers. In certain embodiments, administration of a compound provided herein may result in the decrease of blood alpha-fetoprotein and/or blood des-gamma carboxyprothrombin. Administration of a compound provided herein may further result in the improvement of liver function, as evidenced by a reduction in blood ALT and/or AST levels.

Certain Additional Therapies

Treatments for fibrosis or any of the conditions listed herein may comprise more than one therapy. As such, in certain embodiments provided herein are methods for treating a subject having or suspected of having fibrosis comprising administering at least one therapy in addition to administering a modified oligonucleotide having a nucleobase sequence complementary to a miR-21.

In certain embodiments, the at least one additional therapy comprises a pharmaceutical agent.

In certain embodiments, pharmaceutical agents include anti-inflammatory agents. In certain embodiments, an anti-inflammatory agent is a steroidal anti-inflammatory agent. In certain embodiments, a steroid anti-inflammatory agent is a corticosteroid. In certain embodiments, a corticosteroid is prednisone. In certain embodiments, an anti-inflammatory agent is a non-steroidal anti-inflammatory drug. In certain embodiments, a non-steroidal anti-inflammatory agent is ibuprofen, a COX-I inhibitor, or a COX-2 inhibitor.

In certain embodiments, pharmaceutical agents include immunosuppressive agents. In certain embodiments, an immunosuppressive agent is a corticosteroid, cyclophosphamide, or mycophenolate mofetil.

In certain embodiments, pharmaceutical agents include anti-diabetic agents. Antidiabetic agents include, but are not limited to, biguanides, glucosidase inhibitors, insulins, sulfonylureas, thiazolidenediones, GLP-1 analogs, and DPP-IV inhibitors.

In certain embodiments, pharmaceutical agents include angiotensin II receptor blockers (ARB). In certain embodiments, an angiotensin II receptor blocker is candesartan, irbesartan, olmesartan, losartan, valsartan, telmisartan, or eprosartan.

In certain embodiments, pharmaceutical agents include angiotensin II converting enzyme (ACE) inhibitors. In certain embodiments, an ACE inhibitor is captopril, enalapril, lisinopril, bnazepril, quinapril, fosinopril, or ramipril.

In certain embodiments, an additional therapy is dialysis. In certain embodiments, an additional therapy is renal transplant.

In certain embodiments, pharmaceutical agents include, but are not limited to, diuretics (e.g. sprionolactone, eplerenone, furosemide), inotropes (e.g. dobutamine, milrinone), digoxin, vasodilators, channel blockers, isosorbide dinitrate, hydralazine, nitrates (e.g. isosorbide mononitrate, isosorbide dinitrate), hydralazine, beta-blockers (e.g. carvedilol, metoprolol), and natriuretic peptides (e.g. nesiritide).

In certain embodiments, pharmaceutical agents include heparinoids. In certain embodiments, a heparinoid is pentosan polysulfate.

In certain embodiments, a pharmaceutical agent is a pharmaceutical agent that blocks one or more responses to fibrogenic signals.

In certain embodiments, a pharmaceutical agent is an anti-connective tissue growth factor therapy. In certain embodiments, an anti-CTGF therapy is a monoclonal antibody against CTGF. In certain embodiments, a pharmaceutical agent is an anti-transforming growth factor β therapy. In certain embodiments, an anti-TGF-β therapy is a monoclonal antibody against TGF-β.

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and *echinacea*), and vaccines, e.g., the immunostimulating complex (ISCOM), which comprises a vaccine formulation that combines a multimeric presentation of antigen and an adjuvant.

In certain embodiments, the additional therapy is selected to treat or ameliorate a side effect of one or more pharmaceutical compositions of the present invention. Such side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

Further examples of additional pharmaceutical agents include, but are not limited to, immunoglobulins, including, but not limited to intravenous immunoglobulin (IVIg); analgesics (e.g., acetaminophen); salicylates; antibiotics; antivirals; antifungal agents; adrenergic modifiers; hormones (e.g., anabolic steroids, androgen, estrogen, calcitonin, progestin, somatostatin, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

Cancer treatments often comprise more than one therapy. As such, in certain embodiments the present invention provides methods for reducing or preventing metastasis comprising administering to a subject a compound comprising a modified oligonucleotide, wherein the modified oligonucleotide is complementary to miR-21, and administering at least one additional therapy that is an anti-cancer therapy.

In certain embodiments, an anti-cancer therapy is chemotherapy. Suitable chemotherapeutic agents include docetaxel, cyclophosphamide, ifosfamide, methotrexate, vinblastine, cisplatin, 5-fluorouracil, gemcitabine, doxorubicin, mitomycin c, sorafenib, etoposide, carboplatin, epirubicin, irinotecan and oxaliplatin. An additional suitable chemotherapeutic agent includes an oligomeric compound, other than a composition targeted to miR-21 provided herein, that is used to treat cancer.

In certain embodiments, an anti-cancer therapy is radiation therapy. In certain embodiments, an anti-cancer therapy is surgical resection of a tumor. In certain embodiments, an anti-cancer therapy is a DNA damaging agent, a proliferation inhibitor, an anti-folate, a growth factor receptor inhibitor, an anti-angiogenic agent, a receptor tyrosine kinase inhibitor, a kinase inhibitor, a growth factor inhibitor, or a cytotoxic agent.

In certain embodiments, a DNA damaging agent is 1,3-bis(2-chloroethyl)-1-nitrosourea, busulfan, carboplatin, carmustine, chlorambucil, cisplatin, cyclophosphamide, dacarbazine, daunorubicin, doxorubicin, epirubicin, etoposide, idarubicin, ifosfamide, irinotecan, lomustine, mechlorethamine, melphalan, mitomycin C, mitoxantrone, oxaliplatin, temozolomide, or topotecan.

In certain embodiments, an anti-folate is methotrexate, aminopterin, thymidylate synthase, serine hydroxymethyltransferase, folyilpolyglutamyl synthetase, g-glutamyl hydrolase, glycinamide-ribonucleotide transformylase, leucovorin, amino-imidazole-carboxamide-ribonucleotide transformylase, 5-fluorouracil, or a folate transporter.

In certain embodiments, a growth factor receptor is erlotinib, or gefitinib.

In certain embodiments, an angiogenesis inhibitor is bevacizumab, thalidomide, carboxyamidotriazole, TNP-470, CM101, IFN-α, platelet factor-4, suramin, SU5416, thrombospondin, a VEGFR antagonist, cartilage-derived angiogenesis inhibitory factor, a matrix metalloproteinase inhibitor, angiostatin, endostatin, 2-methoxyestradiol, tecogalan, tetrathiomolybdate, prolactin, or linomide.

In certain embodiments, a kinase inhibitor is bevacizumab, BIBW 2992, cetuximab, imatinib, trastuzumab, gefitinib, ranibizumab, pegaptanib, sorafenib, dasatinib, sunitinib, erlotinib, nilotinib, lapatinib, panitumumab, vandetanib, E7080, pazopanib, mubritinib, or fostamatinib.

Certain MicroRNA Nucleobase Sequences

The modified oligonucleotides having a nucleoside pattern described herein have a nucleobase sequence that is complementary to miR-21 (SEQ ID NO: 1), or a precursor thereof (SEQ ID NO: 2). In certain embodiments, each nucleobase of the modified oligonucleotide is capable of undergoing base-pairing with a nucleobase at each corresponding position in the nucleobase sequence of miR-21. In certain embodiments the nucleobase sequence of a modified oligonucleotide may have one or more mismatched base pairs with respect to the nucleobase sequence of miR-21 or precursor sequence, and remains capable of hybridizing to its target sequence.

As the miR-21 sequence is contained within the miR-21 precursor sequence, a modified oligonucleotide having a nucleobase sequence complementary to miR-21 is also complementary to a region of the miR-21 precursor.

In certain embodiments, a modified oligonucleotide consists of a number of linked nucleosides that is equal to the length of miR-21.

In certain embodiments, the number of linked nucleosides of a modified oligonucleotide is less than the length of miR-21. A modified oligonucleotide having a number of linked nucleosides that is less than the length of miR-21, wherein each nucleobase of the modified oligonucleotide is complementary to each nucleobase at a corresponding position of miR-21, is considered to be a modified oligonucleotide having a nucleobase sequence that is fully complementary to a region of the miR-21 sequence. For example, a modified oligonucleotide consisting of 19 linked nucleosides, where each nucleobase is complementary to a corresponding position of miR-21 that is 22 nucleobases in length, is fully complementary to a 19 nucleobase region of miR-21. Such a modified oligonucleotide has 100% complementarity to a 19 nucleobase portion of miR-21, and is considered to be 100% complementary to miR-21.

In certain embodiments, a modified oligonucleotide comprises a nucleobase sequence that is complementary to a seed sequence, i.e. a modified oligonucleotide comprises a seed-match sequence. In certain embodiments, a seed sequence is a hexamer seed sequence. In certain such embodiments, a seed sequence is nucleobases 1-6 of miR-21. In certain such embodiments, a seed sequence is nucleobases 2-7 of miR-21. In certain such embodiments, a seed sequence is nucleobases 3-8 of miR-21. In certain embodiments, a seed sequence is a heptamer seed sequence. In certain such embodiments, a heptamer seed sequence is nucleobases 1-7 of miR-21. In certain such embodiments, a heptamer seed sequence is nucleobases 2-8 of miR-21. In certain embodiments, the seed sequence is an octamer seed sequence. In certain such embodiments, an octamer seed sequence is nucleobases 1-8 of miR-21. In certain embodiments, an octamer seed sequence is nucleobases 2-9 of miR-21.

In certain embodiments, a modified oligonucleotide has a nucleobase sequence having one mismatch with respect to the nucleobase sequence of miR-21, or a precursor thereof. In certain embodiments, a modified oligonucleotide has a nucleobase sequence having two mismatches with respect to the nucleobase sequence of miR-21, or a precursor thereof. In certain such embodiments, a modified oligonucleotide has a nucleobase sequence having no more than two mismatches with respect to the nucleobase sequence of miR-21, or a precursor thereof. In certain such embodiments, the mismatched nucleobases are contiguous. In certain such embodiments, the mismatched nucleobases are not contiguous.

In certain embodiments, the number of linked nucleosides of a modified oligonucleotide is greater than the length of miR-21. In certain such embodiments, the nucleobase of an additional nucleoside is complementary to a nucleobase of the miR-21 stem-loop sequence. In certain embodiments, the number of linked nucleosides of a modified oligonucleotide is one greater than the length of miR-21. In certain such embodiments, the additional nucleoside is at the 5' terminus of an oligonucleotide. In certain such embodiments, the additional nucleoside is at the 3' terminus of an oligonucleotide. In certain embodiments, the number of linked nucleosides of a modified oligonucleotide is two greater than the length of miR-21. In certain such embodiments, the two additional nucleosides are at the 5' terminus of an oligonucleotide. In certain such embodiments, the two additional nucleosides are at the 3' terminus of an oligonucleotide. In certain such embodiments, one additional nucleoside is located at the 5' terminus and one additional nucleoside is located at the 3' terminus of an oligonucleotide. In certain embodiments, a region of the oligonucleotide may be fully complementary to the nucleobase sequence of miR-21, but the entire modified oligonucleotide is not fully complementary to miR-21. For example, a modified oligonucleotide consisting of 24 linked nucleosides, where the nucleobases of nucleosides 1 through 22 are each complementary to a corresponding position of miR-21 that is 22 nucleobases in length, has a 22 nucleoside portion that is fully complementary to the nucleobase sequence of miR-21 and approximately 92% overall complementarity to the nucleobase sequence of miR-21.

Certain Modified Oligonucleotides

In certain embodiments, a modified oligonucleotide consists of 8 to 30 linked nucleosides. In certain embodiments, a modified oligonucleotide consists of 12 to 30 linked nucleosides. In certain embodiments, a modified oligonucleotide consists of 15 to 30 linked nucleosides. In certain embodiments, a modified oligonucleotide consists of 12 to 25 linked nucleosides. In certain embodiments, a modified oligonucleotide consists of 15 to 25 linked nucleosides. In certain embodiments, a modified oligonucleotide consists of 12 to 19 linked nucleosides. In certain embodiments, a modified oligonucleotide consists of 15 to 19 linked nucleosides. In certain embodiments, a modified oligonucleotide consists of 12 to 16 linked nucleosides. In certain embodiments, a modified oligonucleotide consists of 15 to 16 linked nucleosides. In certain embodiments, a modified oligonucleotide consists of 19 to 24 linked nucleosides. In certain embodiments, a modified oligonucleotide consists of 21 to 24 linked nucleosides.

In certain embodiments, a modified oligonucleotide consists of 8 linked nucleosides. In certain embodiments, a modified oligonucleotide consists of 9 linked nucleosides. In certain embodiments, a modified oligonucleotide consists of 10 linked nucleosides. In certain embodiments, a modified oligonucleotide consists of 11 linked nucleosides. In certain embodiments, a modified oligonucleotide consists of 12 linked nucleosides. In certain embodiments, a modified oligonucleotide consists of 13 linked nucleosides. In certain embodiments, a modified oligonucleotide consists of 14 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides.

The nucleobase sequences set forth herein, including but not limited to those found in the examples and in the sequence listing, are independent of any modification to the nucleic acid. As such, nucleic acids defined by a SEQ ID NO may comprise, independently, one or more modifications to one or more sugar moieties, to one or more internucleoside linkages, and/or to one or more nucleobases.

Although the sequence listing accompanying this filing identifies each nucleobase sequence as either "RNA" or "DNA" as required, in practice, those sequences may be modified with any combination of chemical modifications. One of skill in the art will readily appreciate that such designation as "RNA" or "DNA" to describe modified oligonucleotides is somewhat arbitrary. For example, a modified oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotide having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a 5-methylcytosine. Similarly, an oligonucleotide having the nucleobase sequence "AUCGAUCG" encompasses any oligonucleotide having such nucleobase sequence, whether modified or unmodified, including, but not limited to, such compounds comprising DNA bases, such as those having sequence "ATCGATCG" and those having some DNA bases and some RNA bases such as "AUCGATCG" and oligonucleotides having other modified bases, such as "AT$^{me}$CGAUCG," wherein $^{me}$C indicates a 5-methylcytosine.

Certain Modifications

In certain embodiments, oligonucleotides provided herein may comprise one or more modifications to a nucleobase, sugar, and/or internucleoside linkage, and as such is a modified oligonucleotide. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2'; 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C—(=CH$_2$)-2' and analogs thereof (see, published PCT International Application WO 2008/154401, published on Dec. 8, 2008).

In certain embodiments, such 4' to 2' bridges independently comprise 1 or from 2 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising such bicyclic sugar moieties are referred to as bicyclic nucleosides or BNAs. In certain embodiments, bicyclic nucleosides include, but are not limited to, (A) α-L-Methyleneoxy (4'-CH$_2$—O-2') BNA; (B) β-D-Methyleneoxy (4'-CH$_2$—O-2') BNA; (C) Ethyleneoxy (4'-(CH$_2$)$_2$—O-2') BNA; (D) Aminooxy (4'-CH$_2$—O—N(R)-2') BNA; (E) Oxyamino (4'-CH$_2$—N(R)—O-2') BNA; (F) Methyl(methyleneoxy) (4'-CH(CH$_3$)—O-2') BNA (also referred to as constrained ethyl or cEt); (G) methylene-thio (4'-CH$_2$—S-2') BNA; (H) methylene-amino (4'-CH2-N(R)-2') BNA; (I) methyl carbocyclic (4'-CH$_2$—CH(CH$_3$)-2') BNA; (J) c-MOE (4'-CH$_2$—OMe-2') BNA and (K) propylene carbocyclic (4'-(CH$_2$)$_3$-2') BNA as depicted below.

(A)

(B)

-continued

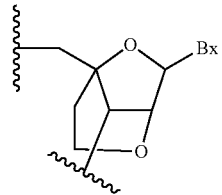

(C)

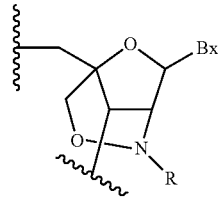

(D)

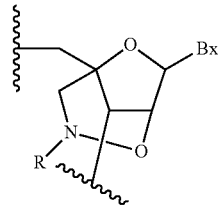

(E)

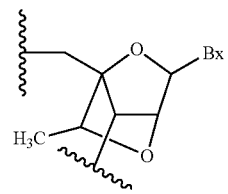

(F)

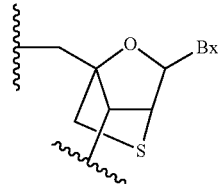

(G)

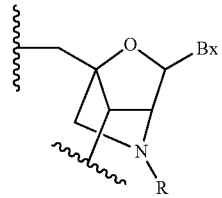

(H)

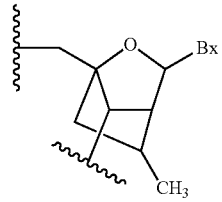

(I)

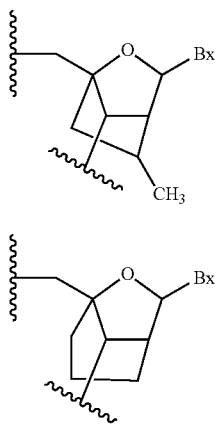

wherein Bx is a nucleobase moiety and R is, independently, H, a protecting group, or $C_1$-$C_{12}$ alkyl.

In certain embodiments, a 2'-modified nucleoside comprises a 2'-substituent group selected from halo, allyl, amino, azido, SH, CN, OCN, $CF_3$, $OCF_3$, O-, S-, or $N(R_m)$-alkyl; O-, S-, or $N(R_m)$-alkenyl; O-, S- or $N(R_m)$-alkynyl; O-alkenyl-O-alkyl, alkynyl, alkaryl, aralkyl, O-alkaryl, O-aralkyl, $O(CH_2)_2SCH_3$, O—$(CH_2)_2$—O—$N(R_m)(R_n)$ or O—$CH_2$—C(=O)—$N(R_m)(R_n)$, where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-modified nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—$N(R_m)(R_n)$, —$O(CH_2)_2O(CH_2)_2N(CH_3)_2$, and N-substituted acetamide (O—$CH_2$—C(=O)—$N(R_m)(R_n)$ where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, $OCF_3$, O—$CH_3$, $OCH_2CH_2OCH_3$, 2'—$O(CH_2)_2SCH_3$, O—$(CH_2)_2$—O—$N(CH_3)_2$, —$O(CH_2)_2O(CH_2)_2N(CH_3)_2$, and O—$CH_2$—C(=O)—$N(H)CH_3$.

In certain embodiments, a 2'-modified nucleoside comprises a 2'-substituent group selected from F, O—$CH_3$, and $OCH_2CH_2OCH_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-O—$(CH_2)_2$—$OCH_3$, and 2'-F.

In certain embodiments, a modified oligonucleotide comprises one or more internucleoside modifications. In certain such embodiments, each internucleoside linkage of a modified oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and $CH_2$ component parts.

In certain embodiments, a modified oligonucleotide comprises one or more modified nucleobases. In certain embodiments, a modified oligonucleotide comprises one or more 5-methylcytosines. In certain embodiments, each cytosine of a modified oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and 0-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

Certain Pharmaceutical Compositions

Provided herein are pharmaceutical compositions comprising oligonucleotides. In certain embodiments, such pharmaceutical compositions are used for the treatment of fibrosis, kidney disease, and cancer. In certain embodiments, a pharmaceutical composition provided herein comprises a compound described herein.

Suitable administration routes include, but are not limited to, oral, rectal, transmucosal, intestinal, enteral, topical, suppository, through inhalation, intrathecal, intracardiac, intraventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver or kidney).

In certain embodiments, a pharmaceutical composition is administered in the form of a dosage unit (e.g., tablet, capsule, bolus, etc.). In some embodiments, a pharmaceutical compositions comprises a modified oligonucleotide at a dose within a range selected from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, and 400 mg to 600 mg. In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of an oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. Further, in some embodiments, the lyophilized modified oligonucleotide is an amount of an oligonucleotide within a range selected from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, and 400 mg to 600 mg. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Lipid moieties have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprises a polyamine compound or a lipid moiety complexed with a nucleic acid. In certain embodiments, such preparations comprise one or more compounds each individually having a structure defined by formula (Z) or a pharmaceutically acceptable salt thereof,

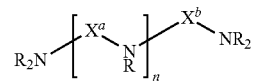

wherein each $X^a$ and $X^b$, for each occurrence, is independently $C_{1-6}$ alkylene; n is 0, 1, 2, 3, 4, or 5; each R is independently H, wherein at least n+2 of the R moieties in at least about 80% of the molecules of the compound of formula (Z) in the preparation are not H; m is 1, 2, 3 or 4; Y is O, $NR^2$, or S; $R^1$ is alkyl, alkenyl, or alkynyl; each of which is optionally substituted with one or more substituents; and $R^2$ is H, alkyl, alkenyl, or alkynyl; each of which is optionally substituted each of which is optionally substituted with one or more substituents; provided that, if n=0, then at least n+3 of the R moieties are not H. Such preparations are described in PCT publication WO/2008/042973, which is herein incorporated by reference in its entirety for the disclosure of lipid preparations. Certain additional preparations are described in Akinc et al., *Nature Biotechnology* 26, 561-569 (1 May 2008), which is herein incorporated by reference in its entirety for the disclosure of lipid preparations.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein is prepared using known techniques, including, but not limited to mixing, dissolving, granulating, dragee-making, levigating, emulsifying, encapsulating, entrapping or tableting processes.

In certain embodiments, a pharmaceutical composition provided herein is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition provided herein is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition provided herein is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition provided herein is prepared for oral administration. In certain of such embodiments, a pharmaceutical composition is formulated by combining one or more compounds comprising a modified oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives).

In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition provided herein comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Certain Routes of Administration

In certain embodiments, administering to a subject comprises parenteral administration. In certain embodiments, administering to a subject comprises intravenous administration. In certain embodiments, administering to a subject comprises subcutaneous administration.

In certain embodiments, administering to a subject comprises intraarterial administration. In certain embodiments, administering to a subject comprises intracardial administration. Suitable means for intracardial administration include the use of a catheter, or administration during open heart surgery. In certain embodiments, administration comprises use of a stent.

In certain embodiments, administration includes pulmonary administration. In certain embodiments, pulmonary administration comprises delivery of aerosolized oligonucleotide to the lung of a subject by inhalation. Following inhalation by a subject of aerosolized oligonucleotide, oligonucleotide distributes to cells of both normal and inflamed lung tissue, including alveolar macrophages, eosinophils, epithelium, blood vessel endothelium, and bronchiolar epithelium. A suitable device for the delivery of a pharmaceutical composition comprising a modified oligonucleotide includes, but is not limited to, a standard nebulizer device. Formulations and methods for modulating the size of droplets using nebulizer devices to target specific portions of the respiratory tract and lungs are well known to those skilled in the art. Additional suitable devices include dry powder inhalers or metered dose inhalers.

In certain embodiments, pharmaceutical compositions are administered to achieve local rather than systemic exposures. For example, pulmonary administration delivers a pharmaceutical composition to the lung, with minimal systemic exposure.

Additional suitable administration routes include, but are not limited to, oral, rectal, transmucosal, intestinal, enteral, topical, transdermal, suppository, intrathecal, intraventricular, intraperitoneal, intranasal, intraocular, intramuscular, intramedullary, and intratumoral.

Certain Compounds

Provided herein are compounds comprising a modified oligonucleotide having certain nucleoside patterns, and uses of these compounds to modulate the activity, level or expression of a target nucleic acid. In certain embodiments, the compound comprises an oligonucleotide. In certain such embodiments, the compound consists of an oligonucleotide. In certain embodiments, the oligonucleotide is a modified oligonucleotide. In certain embodiments, a modified oligonucleotide is complementary to a small non-coding RNA. In certain embodiments, the small non-coding RNA is miR-21.

In certain such embodiments, the compound comprises a modified oligonucleotide hybridized to a complementary strand, i.e. the compound comprises a double-stranded oligomeric compound. In certain embodiments, the hybridization of a modified oligonucleotide to a complementary strand forms at least one blunt end. In certain such embodiments, the hybridization of a modified oligonucleotide to a complementary strand forms a blunt end at each terminus of the double-stranded oligomeric compound. In certain embodiments, a terminus of a modified oligonucleotide comprises one or more additional linked nucleosides relative to the number of linked nucleosides of the complementary strand. In certain embodiments, the one or more additional nucleosides are at the 5' terminus of an oligonucleotide. In certain embodiments, the one or more additional nucleosides are at the 3' terminus of an oligonucleotide. In certain embodiments, at least one nucleobase of a nucleoside of the one or more additional nucleosides is complementary to the target RNA. In certain embodiments, each nucleobase of each one or more additional nucleosides is complementary to the target RNA. In certain embodiments, a terminus of the complementary strand comprises one or more additional linked nucleosides relative to the number of linked nucleosides of an oligonucleotide. In certain embodiments, the one or more additional linked nucleosides are at the 3' terminus of the complementary strand. In certain embodiments, the one or more additional linked nucleosides are at the 5' terminus of the complementary strand. In certain embodiments, two additional linked nucleosides are linked to a terminus. In certain embodiments, one additional nucleoside is linked to a terminus.

In certain embodiments, the compound comprises a modified oligonucleotide conjugated to one or more moieties which enhance the activity, cellular distribution or cellular uptake of the resulting antisense oligonucleotides. In certain such embodiments, the moiety is a cholesterol moiety. In certain embodiments, the moiety is a lipid moiety. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to an oligonucleotide. In certain embodiments, a conjugate group is attached to a modified oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclo-hexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises a modified oligonucleotide having one or more stabilizing groups that are attached to one or both termini of a modified oligonucleotide to enhance properties such as, for example, nuclease stability. Included in stabilizing groups are cap structures. These terminal modifications protect a modified oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Certain Kits

The present invention also provides kits. In some embodiments, the kits comprise one or more compounds of the invention comprising a modified oligonucleotide, wherein the nucleobase sequence of the oligonucleotide is complementary to the nucleobase sequence of miR-21. The compounds complementary to miR-21 can have any of the nucleoside patterns described herein. In some embodiments, the compounds complementary to miR-21 can be present within a vial. A plurality of vials, such as 10, can be present in, for example, dispensing packs. In some embodiments, the vial is manufactured so as to be accessible with a syringe. The kit can also contain instructions for using the compounds complementary to miR-21.

In some embodiments, the kits may be used for administration of the compound complementary to miR-21 to a subject. In such instances, in addition to compounds complementary to miR-21, the kit can further comprise one or more of the following: syringe, alcohol swab, cotton ball, and/or gauze pad. In some embodiments, the compounds complementary to miR-21 can be present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering the compounds complementary to miR-21.

Certain Experimental Models

In certain embodiments, the present invention provides methods of using and/or testing modified oligonucleotides of the present invention in an experimental model. Those having skill in the art are able to select and modify the protocols for such experimental models to evaluate a pharmaceutical agent of the invention.

Generally, modified oligonucleotides are first tested in cultured cells. Suitable cell types include those that are related to the cell type to which delivery of a modified oligonucleotide is desired in vivo. For example, suitable cell types for the study of the methods described herein include primary or cultured cells.

In certain embodiments, the extent to which a modified oligonucleotide interferes with the activity of miR-21 is assessed in cultured cells. In certain embodiments, inhibition of microRNA activity may be assessed by measuring the levels of the microRNA. Alternatively, the level of a predicted or validated microRNA-regulated transcript may be measured. An inhibition of microRNA activity may result in the increase in the miR-21-regulated transcript, and/or the protein encoded by miR-21-regulated transcript. Further, in certain embodiments, certain phenotypic outcomes may be measured.

Several animal models are available to the skilled artisan for the study of miR-21 in models of human disease. For example, inhibitors of miR-21 may be studied in models of cancer, such as orthotopic xenograft models, toxin-induced cancer models, or genetically-induced cancer models. In such cancer models, the studies may be performed to evaluate the effects of inhibitors of miR-21 on tumor size, tumor number, overall survival and/or progression-free survival.

The effects of inhibitors of miR-21 on cardiac function and fibrosis may be studied in models of transaortic banding or myocardial infarction, each of which induces abnormal cardiac function and fibrosis. Models of kidney fibrosis include unilateral ureteral obstruction and ischemia/reperfusion injury. During early time points, the kidney ischemia reperfusion injury model may be used as a model for acute kidney injury, while later time points serve as a model for kidney fibrosis. An additional model of kidney fibrosis is aristolochic acid-induced fibrosis model. Liver fibrosis models are induced by, for example, carbon tetrachloride intoxication or bile duct ligation. Liver fibrosis may also be induced by a methionine and choline deficient diet, which results in steatotic liver with associated fibrosis. The effects of miR-21 on lung fibrosis may be studied, for example, in a model of bleomycin-induced pulmonary fibrosis or in mice that overexpress TGF-β in the lung. Wound healing models are also available to the skilled artisan, for example the C57Bl/KsJ-db/db mice, which exhibit several characteristics of adult onset diabetes, such as markedly delayed wound closure.

An additional animal model includes a mouse or canine Alport Syndrome model. An example of a mouse model of Alport Syndrome is the Col4a3 knockout mouse.

Certain Quantitation Assays

The effects of antisense inhibition of miR-21 following the administration of modified oligonucleotides may be assessed by a variety of methods known in the art. In certain embodiments, these methods are be used to quantitate microRNA levels in cells or tissues in vitro or in vivo. In certain embodiments, changes in microRNA levels are measured by microarray analysis. In certain embodiments, changes in microRNA levels are measured by one of several commercially available PCR assays, such as the TaqMan® MicroRNA Assay (Applied Biosystems). In certain embodiments, antisense inhibition of miR-21 is assessed by measuring the mRNA and/or protein level of a target of miR-21. Antisense inhibition of miR-21 generally results in the increase in the level of mRNA and/or protein of a target of the microRNA.

Target Engagement Assay

Modulation of microRNA activity with an anti-miR or microRNA mimic may be assessed by measuring target engagement. In certain embodiments, target engagement is measured by microarray profiling of mRNAs. The sequences of the mRNAs that are modulated (either increased or decreased) by the anti-miR or microRNA mimic are searched for microRNA seed sequences, to compare modulation of mRNAs that are targets of the microRNA to modulation of mRNAs that are not targets of the microRNA. In this manner, the interaction of the anti-miR with miR-21, or miR-21 mimic with its targets, can be evaluated. In the case of an anti-miR, mRNAs whose expression levels are increased are screened for the mRNA sequences that comprise a seed match to the microRNA to which the anti-miR is complementary.

EXAMPLES

The following examples are presented in order to more fully illustrate some embodiments of the invention. They should, in no way be construed, however, as limiting the broad scope of the invention. Those of ordinary skill in the art will readily adopt the underlying principles of this discovery to design various compounds without departing from the spirit of the current invention.

Example 1

Anti-miR-21 Compounds

Various anti-miRs targeted to miR-21 and comprising cEt nucleosides were designed with variations in length and complementarity to miR-21, as well as in the number, type and placement of modified sugar moieties. The compounds were evaluated for their inhibitory effects on miR-21 activity in an in vitro luciferase assay.

Luciferase Assay

The compounds were assessed for miR-21 inhibitory activity in a luciferase assay. A microRNA luciferase sensor construct was engineered using pGL3-MCS2 (Promega). The construct was introduced into Hela cells to test the ability of anti-miR compounds to inhibit activity of miR-21. In this assay, miR-21 present in the Hela cells binds to its cognate site(s) in the luciferase sensor construct, and suppresses luciferase expression. When the appropriate anti-miR is introduced into the cells, it binds to miR-21 and relieves suppression of luciferase expression. Thus, in this assay anti-miRs that are effective inhibitors of miR-21 expression will cause an increase in luciferase expression.

Day 1:

Hela cells (ATCC), stably transfected with a luciferase construct engineered to contain a sequence complementary of miR-21, were seeded in T-170 flasks (BD Falcon) at $3.5*10^6$ cells/flask. Hela cells were grown in Dulbecco's Modified Eagle Medium with High Glucose (Invitrogen).

Day 2:

Each flask of Hela cells was transfected with 0.5 ug of a phRL sensor plasmid (Promega) expressing Renilla to be used in normalization. Hela cells were transfected using 20 ul Lipofectamine 2000/flask (Invitrogen). After 4 hours of transfection, cells were washed with PBS and trypsinized. Hela cells were plated at 40 k/well in 24 well plates (BD Falcon) and left overnight.

Day 3:

Hela cells were transfected with anti-miRs using Lipofectin (Invitrogen) at 2.5 ul Lipofectin/100 nM ASO/ml Opti-MEM I Reduced Serum Medium (Invitrogen) for 4 hours. After ASO transfection, Hela cells were refed with Dulbecco's Modified Eagle Medium with High Glucose (Invitrogen).

Day 4:

Hela cells are passively lysed and luciferase activity measured using the Dual-Luciferase Reporter Assay System (Promega).

Luciferase activity in anti-miR-21-treated cells was compared to a 'mock' treatment, in which cells received no anti-miR treatment.

Certain of the active compounds are shown in Table A. Nucleoside modifications are indicated as follows: nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides. Each internucleoside linkage is a phosphorothioate internucleoside linkage. Superscript "Me" indicates a 5-methyl group on the base of the nucleoside.

TABLE A

Anti-miR-21 Compounds

| Compound # | Sequence and Chemistry (Subscript "s" indicates S-cEt nucleoside) | SEQ ID NO |
|---|---|---|
| 36328 | $^{Me}C_E$ $A_S$ $G_S$ $T_E$ $C_S$ $U_S$ $G_E$ $A_E$ $U_S$ $A_S$ $A_E$ $G_E$ $C_S$ $T_E$ $A_S$ | 5 |
| 36232 | C $A_S$ $G_S$ T $C_S$ $U_S$ G A $U_S$ $A_S$ A G $C_S$ T $A_S$ | 5 |
| 36234 | C $A_S$ $G_S$ T $C_S$ $U_S$ G A $U_S$ A $A_S$ $G_S$ C T $A_S$ | 5 |
| 36235 | C $A_S$ $G_S$ T $C_S$ $U_S$ G A $U_S$ A $A_S$ G $C_S$ T $A_S$ | 5 |
| 36237 | C $A_S$ $G_S$ T $C_S$ $U_S$ G A $U_S$ A A $G_S$ $C_S$ T $A_S$ | 5 |

TABLE B

Inhibitory activity of anti-miR-21 compounds

| Treatment | Concentration of Oligonucleotide (uM) | | | | | |
|---|---|---|---|---|---|---|
| | 50 | 16.7 | 5.6 | 1.9 | 0.6 | 0.2 |
| 36328 | 1.1 | 4.36 | 1.05 | 0.93 | 0.94 | 0.98 |
| 36232 | 1.1 | 4.2 | 5.22 | 2.37 | 0.9 | 0.76 |
| 36234 | 1.02 | 4.4 | 4.96 | 1.67 | 1.03 | 0.79 |
| 36235 | 2 | 6.17 | 7.57 | 3.01 | 1.1 | 1.01 |
| 36237 | 1.49 | 6.2 | 4.35 | 1.14 | 0.93 | 0.99 |

As shown in Table B, the anti-miR-21 compounds of Table A inhibited miR-21 activity in vitro in the luciferase assay. These active compounds were selected for further testing in an in vivo model of kidney fibrosis.

UUO Model of Fibrosis

Unilateral ureteral obstruction (UUO) is a well-established experimental model of renal injury leading to interstitial fibrosis, and thus is used as an experimental model that is reflective of human kidney disease. UUO is induced by surgically ligating a single ureter. As fibrosis is characterized by an increase in collagen, the presence and extent of kidney fibrosis may be determined by measuring collagen content. Both collagen 1A1 (Col 1A1) and collagen 3A1 (Col 3A1) are measured to assess collagen content. An additional indicator of fibrosis is the percentage of kidney tissue that exhibits collagen expression following the UUO procedure. This 'collagen area fraction' is measured histologically through quantitative image processing of the area of kidney tissue that is stained red by the picrosirius red stain; the percent detected as red is normalized by the area of kidney section. Kidney fibrosis may also be observed by measuring the amount of hydroxyproline, which is a major component of collagen, in a sample.

Figure 1B:
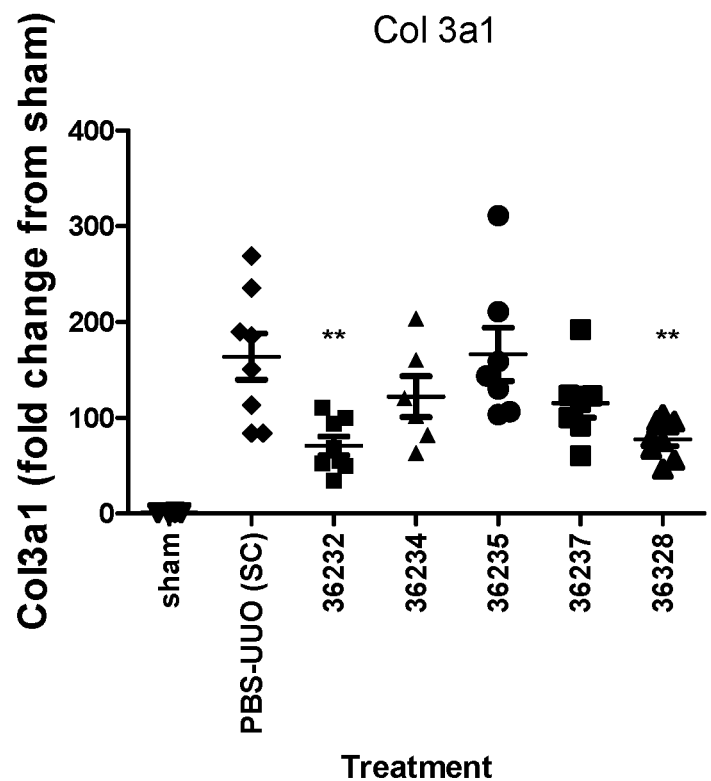

The cEt-containing anti-miR-21 compounds 36232, 36234, 36235, 36237, and 36328 were tested in the UUO model of kidney fibrosis. Groups of animals were treated as follows: UUO only (n=4), UUO with PBS (n=8), or UUO with anti-miR-21 compound (n=7 to 8). Relative to the day of the UUO procedure, PBS or anti-miR-21 compound was administered at days −4, −2, 0, and +3. Anti-miR-21 compounds were administered at a dose of 20 mg/kg. As the anti-miR compounds were administered prior to the UUO procedure, this dosing regimen is considered a prophylactic treatment. At day 11, animals were sacrificed and kidney was isolated for measurement of collagen expression. Collagen expression was measured by real-time PCR and normalized first to GAPDH and then to the sham control animals. Statistical significance was determined according to a 1-way ANOVA test. As shown in FIG. 1, treatment with 36232 and 36328 reduced the expression of collagen 1A1 (FIG. 1A) and collagen 3A1 (FIG. 1B) in a statistically significant manner, relative to sham-treated animals. Although they were active inhibitors of miR-21 in vitro, the compounds 36234, 36235, and 36237 did not result in statistically significant reductions in collagen expression in vivo.

These results demonstrate that 36328 and 36232 are candidate agents for the treatment or prevention of fibrosis, including kidney fibrosis.

Although compounds 36328 and 36232 have identical S-cEt nucleoside placement and inhibit miR-21 in vitro and in vivo, they exhibit markedly different viscosities in solution. 36328 is a highly viscous in a saline solution, where as 36232 is not. A highly viscous solution may not be suitable for administration, for example, via a subcutaneous injection, as a larger volume of administration would be required to accommodate the required amount of anti-miR, and larger volumes are more difficult to administer subcutaneously. A lower viscosity solution may be desirable in order to facilitate administration of an agent. In an effort to alter the viscosity of 36328, variations were designed as shown in Table C. Each compound was tested for activity in the luciferase assay, viscosity in water, and activity in the UUO model.

TABLE C 36328 and related compounds

| Compound # | Sequence and Chemistry (Subscript "s" indicates cEt sugar; underscore indicates mismatch) | SEQ ID NO |
|---|---|---|
| 36328 | $^{Me}C_E$ $A_S$ $G_S$ $T_E$ $C_S$ $U_S$ $G_E$ $A_E$ $U_S$ $A_S$ $A_E$ $G_E$ $C_S$ $T_E$ $A_S$ | 5 |
| 36282 | $^{Me}C_E$ $A_S$ $G_S$ $T_E$ $\underline{A_S}$ $U_S$ $G_E$ $A_E$ $U_S$ $A_S$ $A_E$ $G_E$ $C_S$ $T_E$ $A_S$ | 11 |
| 36283 | $^{Me}C_E$ $A_S$ $G_S$ $T_E$ $\underline{A_S}$ $U_S$ $\underline{A_E}$ $A_E$ $U_S$ $A_S$ $A_E$ $G_E$ $C_S$ $T_E$ $A_S$ | 12 |
| 36284 | $^{Me}C_E$ $A_S$ $\underline{A_S}$ $T_E$ $C_S$ $U_S$ $\underline{A_E}$ $A_E$ $U_S$ $A_S$ $A_E$ $G_E$ $C_S$ $T_E$ $A_S$ | 7 |
| 36285 | $^{Me}C_E$ $A_S$ $\underline{A_S}$ $T_E$ $C_S$ $\underline{A_S}$ $\underline{A_E}$ $A_E$ $U_S$ $A_S$ $A_E$ $G_E$ $C_S$ $T_E$ $A_S$ | 13 |

Results from the luciferase assay are shown in Table D and are shown as fold increase in luciferase activity, relative to mock transfection. As shown in Table D, 36283, 36284 and 36328 inhibited miR-21 activity. 36282 and 36285 were not effective inhibitors of miR-21 in vitro Inhibitory activity of 36328 from a separate experiment (above) is shown for comparison.

TABLE D anti-miR-21 activity in vitro

| Treatment | Concentration of Oligonucleotide (uM) | | | | |
|---|---|---|---|---|---|
| | 50 | 16.7 | 5.6 | 1.9 | 0.6 |
| 36282 | 1.67 | 1.33 | 1.10 | 1.13 | 0.77 |
| 36283 | 5.90 | 5.50 | 3.57 | 2.30 | 0.60 |
| 36284 | 5.00 | 5.03 | 3.67 | 2.13 | 1.10 |
| 36285 | 1.27 | 0.90 | 0.97 | 1.03 | 0.87 |
| 36328 | 1.1 | 4.36 | 1.05 | 0.93 | 0.94 |

Compounds were dissolved in water. Using routing methods, oligonucleotide concentration was calculated gravimetrically (mg/g) and viscosity (cP) was measured using a viscometer. Results are shown in Table E.

TABLE E

Anti-miR-21 compound viscosity

| Compound # | Viscosity cP | Concentration mg/g |
|---|---|---|
| 36282 | 178 | 156 |
| 36283 | 147 | 165 |
| 36284 | 25 | 184 |
| 36285 | 13 | 174 |
| 36328 | 212 | 141 |

Introducing a single mismatch into compound #36382 reduced viscosity only slightly, and significantly reduced miR-21 inhibitory activity in the luciferase assay. Introducing three mismatches into compound #36285 significantly reduced viscosity, but resulted in very weak miR-21 inhibitory activity in the luciferase assay. Compounds 36283 and 36284 each inhibited miR-21 in the luciferase assay but exhibited very different viscosities. Compound 36284 has one mismatch at nucleobase position 3 and one mismatch at nucleobase position 7 and exhibited a very low viscosity. Compound 36283 has one mismatch at nucleobase position 3 and one mismatch at nucleobase position 5 and was found to have a high viscosity.

Figure 2A:
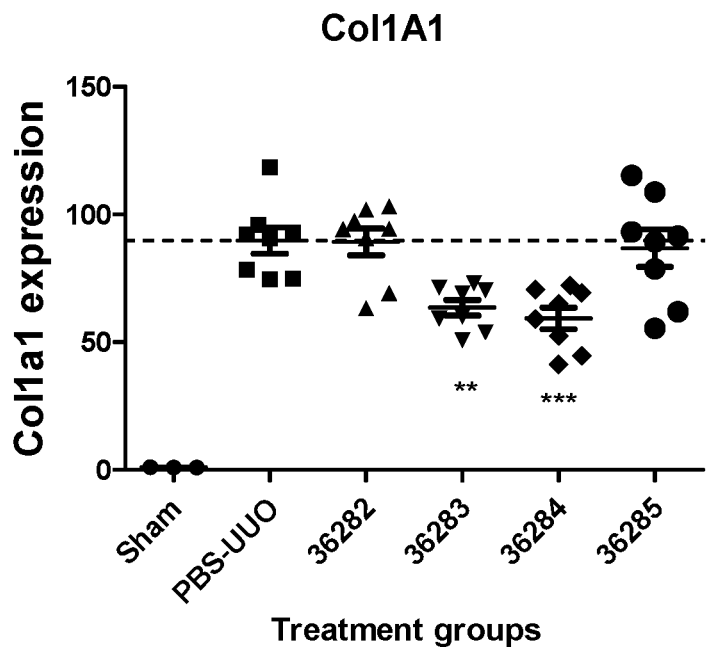
FIGS. 2A and 2B show the change in (A) collagen 1A1 and (B) collagen 3A1 expression in kidneys of UUO model mice administered certain anti-miR-21 compounds, as described in Example 1.
Figure 2B:
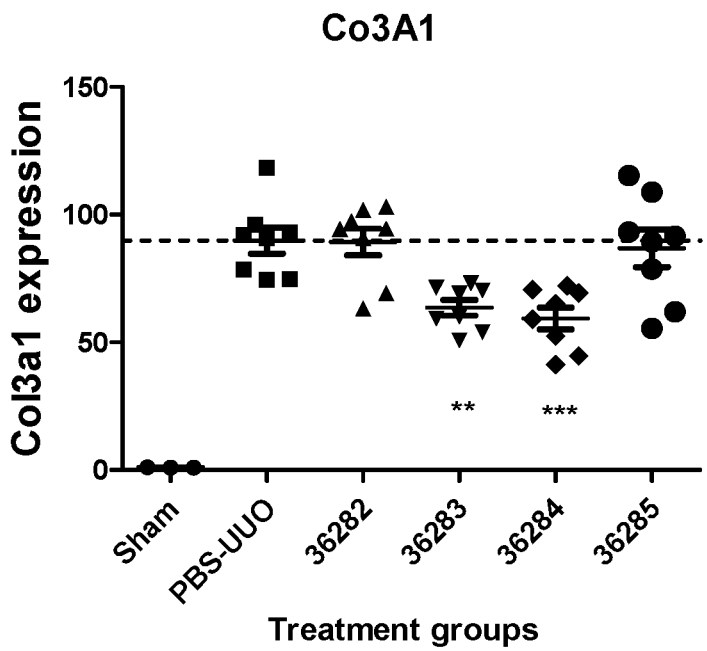

To evaluate in vivo activity, each of the compounds was tested in the UUO model. Groups of animals were treated as follows: sham surgery (n=4), UUO with PBS (n=8), or UUO with anti-miR-21 compound (n=7 to 8). Relative to the day of the UUO procedure, PBS or anti-miR-21 compound was administered at days −3, −1, and +5. Anti-miR-21 compounds were administered at a dose of 20 mg/kg. As the anti-miR compounds were administered prior to the UUO procedure, this dosing regimen is considered a prophylactic treatment. At day 11, animals were sacrificed and kidney was isolated for measurement of collagen expression. Collagen expression was measured by real-time PCR and normalized first to GAPDH and then to the sham control animals. Statistical significance was determined according to a 1-way ANOVA test. As shown in FIG. 2, treatment with 36283 and 36284 reduced the expression of collagen 1A1 (FIG. 2A) and collagen 3A1 (FIG. 2B) in a statistically significant manner, relative to sham-treated animals. The compounds 36282 and 36285 did not result in statistically significant reductions in collagen expression in vivo.

These results demonstrate that 36284 significantly reduced the expression of both Col1A1 and Col1A3 and exhibited a low viscosity in solution.

Example 2

Metabolic Stability of Anti-miR-21 Compound

It has been found that certain anti-miR-21 compounds are particularly susceptible to metabolism by endonuclease and/or exonuclease activity. To facilitate anti-miR distribution and prolong half-life, increased stability in the presence of nucleases in vivo may be a desirable property of an anti-miR-21 compound and as such, compounds of varying structure were tested for metabolic stability. The compounds tested included 25923, which was found to be susceptible to nuclease activity, and structural variants 25220 and 25221. The structure of each compound is shown in Table F. Nucleoside modifications are indicated as follows: nucleosides not followed by a subscript indicate β-D-deoxyribonucleosides; nucleosides followed by a subscript "E" indicate 2′-MOE nucleosides; nucleosides followed by a subscript "S" indicate S-cEt nucleosides. Each internucleoside linkage is a phosphorothioate internucleoside linkage.

TABLE F

Anti-miR-21 compounds

| Compound # | Sequence and Chemistry (5' to 3') | SEQ ID NO |
|---|---|---|
| 25923 | $A_E$ $C_S$ A T $C_S$ A G T $C_S$ T G A $U_S$ A A G $C_S$ T $A_S$ | 3 |
| 25220 | $A_E$ $C_S$ A T $C_S$ $A_S$ G T $C_S$ $U_S$ G A $U_S$ $A_S$ A G $C_S$ $U_S$ $A_E$ | 3 |
| 25221 | $A_E$ $C_S$ A T $C_S$ A G T $C_S$ T G A $U_S$ A A G $C_S$ $U_S$ $A_S$ | 3 |

In an ex vivo assay, 5 μM of oligonucleotide was incubated in liver homogenate (50 mg tissue per ml) for 24 hours at 37° C. Following this incubation, oligonucleotide was extracted by Liquid-Liquid Extraction (LLE) followed by Solid-Phase Extraction (SPE). Oligonucleotide lengths and amounts were measure by high-performance liquid chromatography time-of-flight mass spectrometry (HPLC-TOF MS). Nuclease activity in the liver tissue homogenate was confirmed by using reference oligonucleotides, which included a compound with known resistance to nuclease activity, a compound susceptible to 3'-exonuclease activity, and a compound susceptible to endonuclease activity. An internal standard compound was used to control for extraction efficiency. For testing of metabolic stability in vivo, compounds were administered to mice, kidney tissue was isolated, and the extraction and detection of compound was performed as for the ex vivo assay. Table G shows the structures for the compounds 25923, 25220 and 25221, and the results of the stability measurements.

expression by a statically significant amount (*=p<0.05; =p<0.01; *=p<0.001), as did administration of compound 25923.

These results demonstrate that 25220 and 25221 significantly reduce both Col1A1 and Col3A1 expression and exhibit resistance to metabolism by nucleases.

The metabolic stability of 25284 was also tested. In an ex vivo assay, only full-length compound was detected. In vivo, 96% of the compound detected was full-length compound. These results demonstrate that 25284 is highly resistant to nuclease activity.

Example 3

Inhibition of miR-21 in Model of Ischemia/Reperfusion Injury

The unilateral ischemia reperfusion injury (IRI) model is a well-characterized model of kidney injury that results in

TABLE G 25923, 25220 and 25221 ex vivo and in vivo stability

| Compound | SEQ ID NO | Structure | ex vivo (liver) N %↓ | % N − 1 | % Endo | in vivo (kidney) N (%) | N − 1 (%) |
|---|---|---|---|---|---|---|---|
| 25923 | 3 | $A_EC_SATC_SAGTC_STGAU_SAAGC_STA_S$ | 17 | 13 | 2-3 | 58 ± 3 | 14 ± 5 |
| 25220 | 3 | $A_EC_SATC_SA_SGTC_SU_SGAU_SA_SAGC_SU_SA_E$ | 3 | 0 | 3 | 67 ± 16 | 16 ± 6 |
| 25221 | 3 | $A_EC_SATC_SAGTC_STGAU_SAAGC_SU_SA_S$ | 3 | 0 | 3 | 76 ± 4 | 4 ± 1 |

As shown in Table G, compounds 25220 and 25221 exhibited increased resistance to nuclease activity in both the ex vivo and in vivo assays.

To evaluate the effects of the compounds on fibrosis, compounds 25220 and 25221, as well as 25923, were tested in the UUO model. Groups of 8 animals each were treated as follows: sham surgery, UUO with PBS, UUO with 25220, UUO with 25221, or UUO with 25923. Relative to the day of the UUO procedure, PBS or anti-miR-21 compound was administered at days −5, −3, and +3. Anti-miR-21 compounds were administered at a dose of 20 mg/kg. As the anti-miR compounds were administered prior to the UUO procedure, this dosing regimen is considered a prophylactic treatment. At day 10, animals were sacrificed and kidney was isolated for measurement of collagen expression. Collagen expression was measured by real-time PCR and normalized to GAPDH.

Figure 3A:
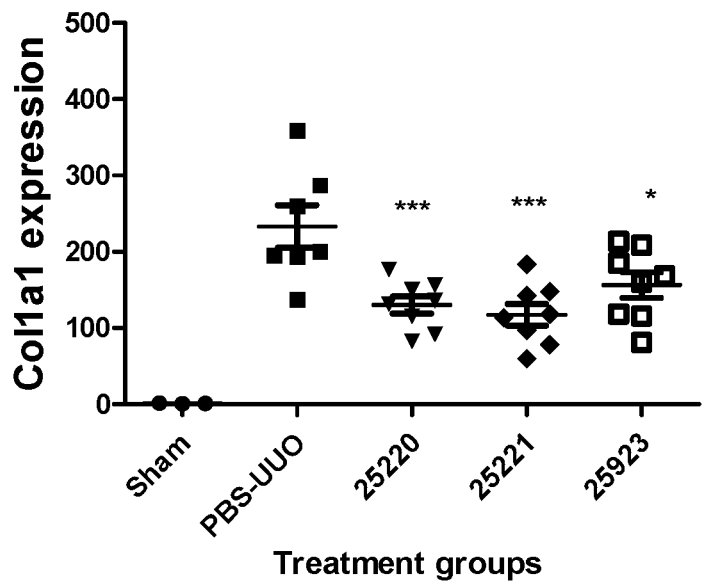
FIGS. 3A and 3B shows the change in (A) collagen 1A1 and (B) collagen 3A1 expression in kidneys of UUO model mice administered certain anti-miR-21 compounds, as described in Example 2.
Figure 3B:
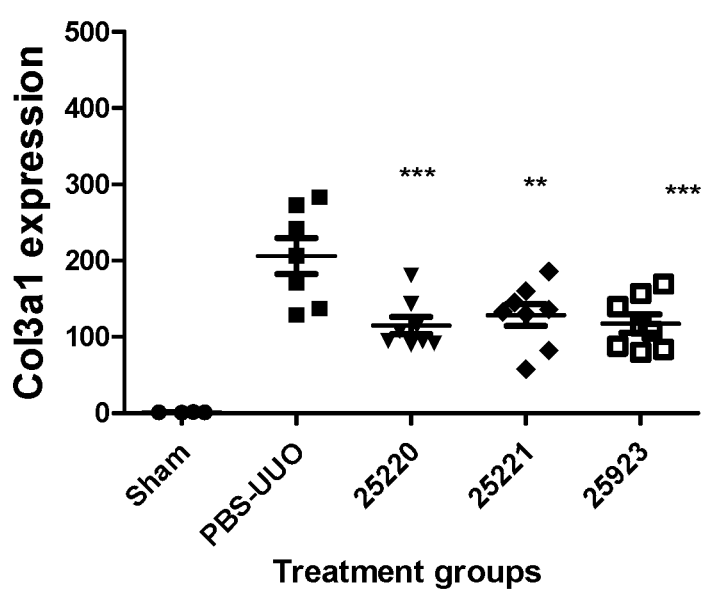

The results of that experiment are shown in FIG. 3. Collagen 1A1 and collagen 3A1 expression are shown in FIGS. 3A and 3B, respectively. Administration of compound 25220 or 25221 reduced collagen 1A1 and collagen 3A1 progressive interstitial fibrosis. The injury is created in the mouse through the clamping of a renal artery for a short period of time, followed by restoration of blood flow. The reperfusion results in severe injury to the kidney, which is followed by chronic injury with fibrosis. IRI leading to chronic injury is often observed in humans, thus the mouse IRI model may be used to test candidate agents for the treatment and/or prevention of fibrosis in the context of kidney injury.

Anti-miR-21 compounds were tested in the unilateral IRI model. Unilateral IRI was induced for a period of 30 minutes (Day 0). Treatment groups were as follows: sham IRI procedure; IRI with PBS administered subcutaneously; IRI with anti-miR-21 compound administered intraperitoneally at a dose of 20 mg/kg. PBS or anti-miR compound was administered on days 5, 6, and 7 following IRI, and animals were sacrificed on Day 13. As anti-miR compound is administered 5 days following the injury to the kidney, or later, when fibrosis has already occurred to some extent, this treatment regimen is considered a therapeutic regimen, rather than a prophylactic regimen.

Figure 4A:
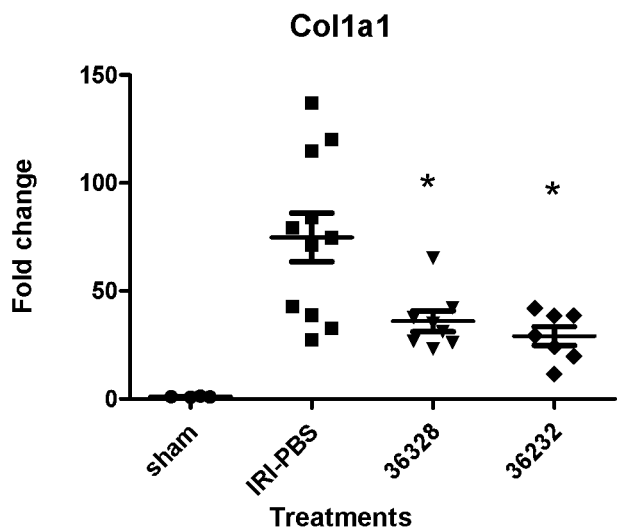
FIGS. 4A-4C show (A) the change in collagen 1A1 expression, (B) the change in collagen 3A1 expression, and (C) the collagen area fraction in kidneys of unilateral IRI model mice administered certain anti-miR-21 compounds, as described in Example 3.
Figure 4B:
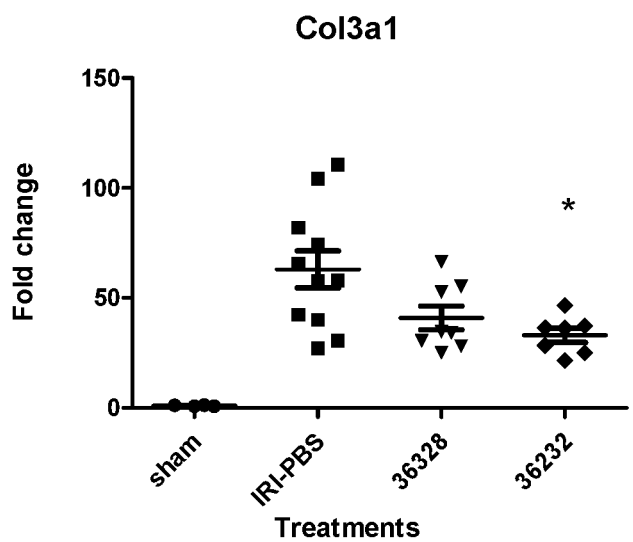
Figure 4C:
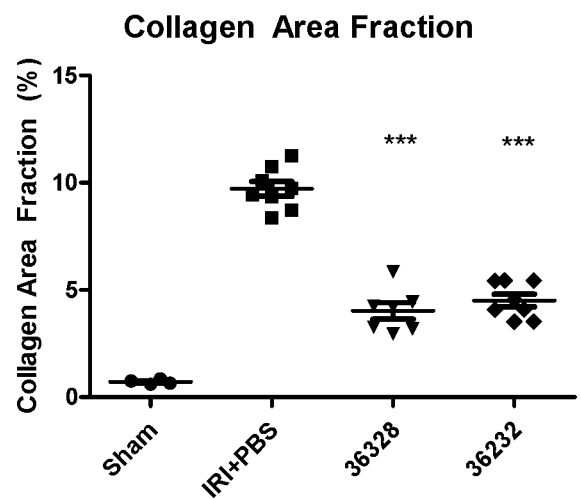

Kidney tissue was collected for analysis of collagen 1A1 and collagen 3A1 expression, and collagen area fraction (as described in the previous example). Statistical significance was determined by a 1-way ANOVA test. The results are shown in FIG. 4. In this study, anti-miR-21 treatment with 36328 or 36232 produced a statistically significant reduction in Col1a1 expression (FIG. 4A; *=p<0.05) and in collagen area fraction (FIG. 4C; ***=p<0.0001). Compound 36232 reduced Col3a1 expression in a statistically significant manner (FIG. 4B). Compound 36328 reduced Col3a1 expression, however the reduction was not statistically significant (FIG. 4B).

These studies demonstrate a reduction in collagen content following inhibition of miR-21 in a model of acute kidney injury. Thus, the anti-miR-21 compounds 36232 and 36328 are therapeutic agents for the treatment of fibrosis in the context of acute kidney injury. For example, preventing or delaying the onset of fibrosis following acute kidney injury may prevent or delay the onset of fibrosis and chronic kidney disease.

Example 4

Inhibition of miR-21 in an Ischemia Reperfusion Injury/Nephrectomy Model

An ischemia reperfusion injury/nephrectomy (IR/Nx) model is created in the mouse through temporary unilateral clamping of an artery in one kidney, which leads to tubule damage, inflammation, and fibrosis, followed by removal of the second kidney at a later timepoint. In this model, the acute kidney dysfunction phase is useful to test candidate agents for the treatment of acute kidney injury (i.e. up to about the first 5 days), and the later phases of kidney dysfunction are useful to model chronic fibrosis (i.e. after about the first 5 days).

Anti-miR-21 compounds were tested in the IR/Nx model. 25109, a 6-base mismatch to miR-21, was used as a control compound ($A_E A_S ATC_S TGTC_S TCAU_S AATA_S AA_E$; SEQ ID NO: 14; where nucleosides not followed by a subscript indicate β-deoxynucleosides; nucleosides followed by a subscript "E" indicate 2'-MOE nucleosides; nucleosides followed by a subscript "S" indicate S-cEt nucleosides; and all internucleoside linkages are phosphorothioate internucleoside linkages).

Unilateral IR was induced for a period of 30 minutes. Treatment groups were as follows: sham IR procedure (n=8); IR with PBS administered subcutaneously (n=16); IR with mismatched control 25109 administered subcutaneously at a dose of 20 mg/kg (n=16); and IR with anti-miR-21 compound 36328 administered subcutaneously at a dose of 20 mg/kg (n=16). PBS or anti-miR was administered on days 2, 3, 4, and 8 following IR. On day 8, the healthy kidney was removed by nephrectomy from each animal, and animals were sacrificed on day 9. Just prior to sacrifice, urine was collected by direct bladder puncture.

Figure 5A:
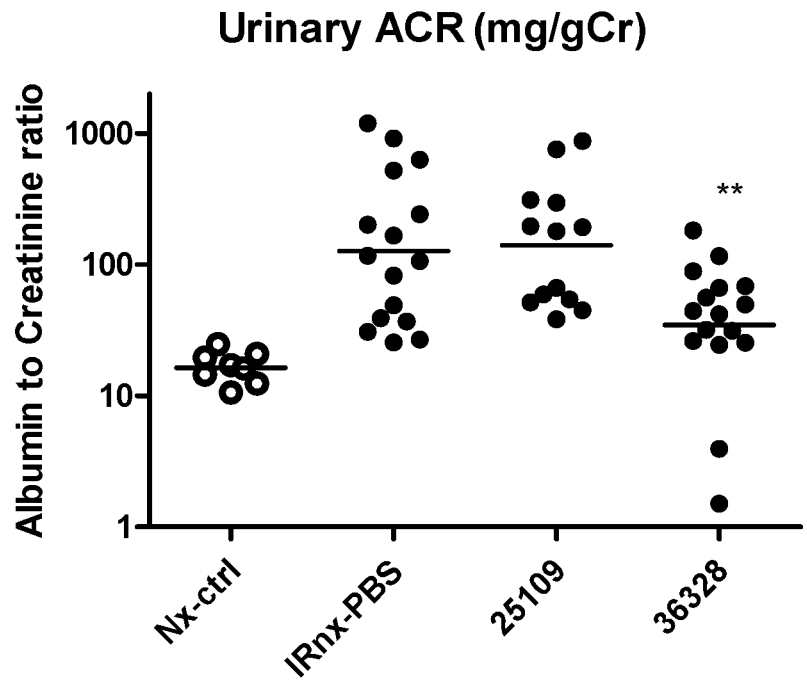
FIGS. 5A-5C show (A) urinary albumin to creatinine ratio in kidneys of IR/Nx model mice administered compound 36328 or a control compound, (B) urinary albumin to creatinine ratio in kidneys of IR/Nx model mice administered compound 36284, and (C) urinary albumin to creatinine ratio in kidneys of IR/Nx model mice administered compound 25220, as described in Example 4.

To assess albuminuria, urinary albumin to creatinine ratio was measured in the urine from each mouse. The results of that experiment are shown in FIG. 5A. In this study, 36328 produced a statistically significant reduction in urinary albumin to creatinine ratio (FIG. 5A). The geometric mean of the albumin to creatinine ratio in each group of mice was 16 μgAlb/mgCr (nephrectomy-only control), 127 μgAlb/mgCr (IR/Nx, PBS control), 140 μgAlb/mgCr (IR/Nx, 25109 control), and 30 μgAlb/mgCr (IR/Nx, 36328). Blood urea nitrogen and serum creatinine levels were similar across all IR/Nx mice, and were elevated relative to nephrectomy-only control mice (data not shown).

Figure 5B:
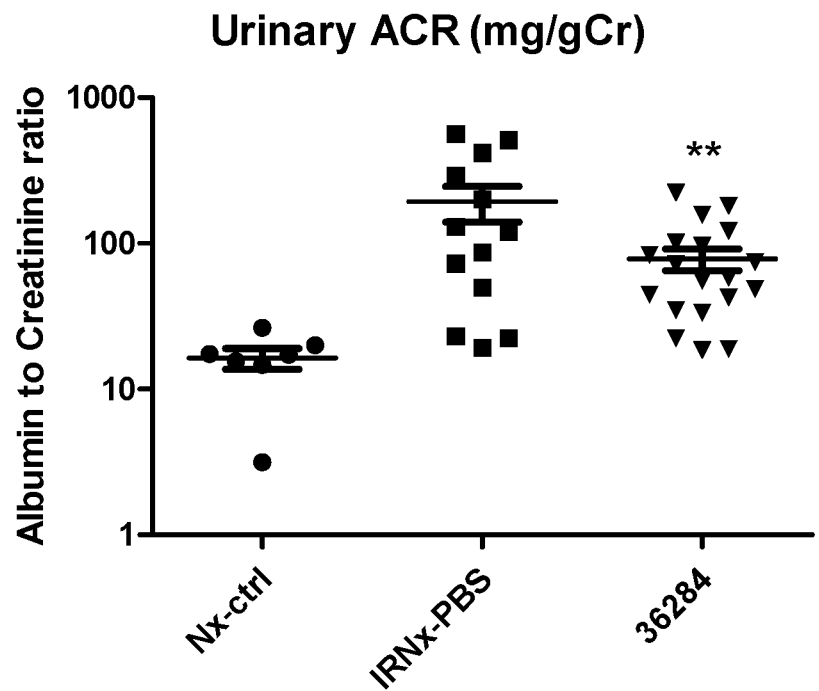

In a similarly designed experiment, the compound 36284 was also tested in the IR/Nx model. Unilateral IR was induced for a period of 30 minutes. Treatment groups were as follows: sham IR procedure (n=7); IR with PBS administered subcutaneously (n=13); and IR with anti-miR-21 compound 36284 administered subcutaneously at a dose of 20 mg/kg (n=19). PBS or anti-miR was administered on days 2, 3, 4, and 8 following IR. On day 8, the healthy kidney was removed by nephrectomy from each animal, and animals were sacrificed on day 9. Just prior to sacrifice, urine was collected by direct bladder puncture. To assess albuminuria, urinary albumin to creatinine ratio was measured in the urine from each mouse. The results of that experiment are shown in FIG. 5B. In this study, 36284 produced a statistically significant reduction in urinary albumin to creatinine ratio.

Figure 5C:
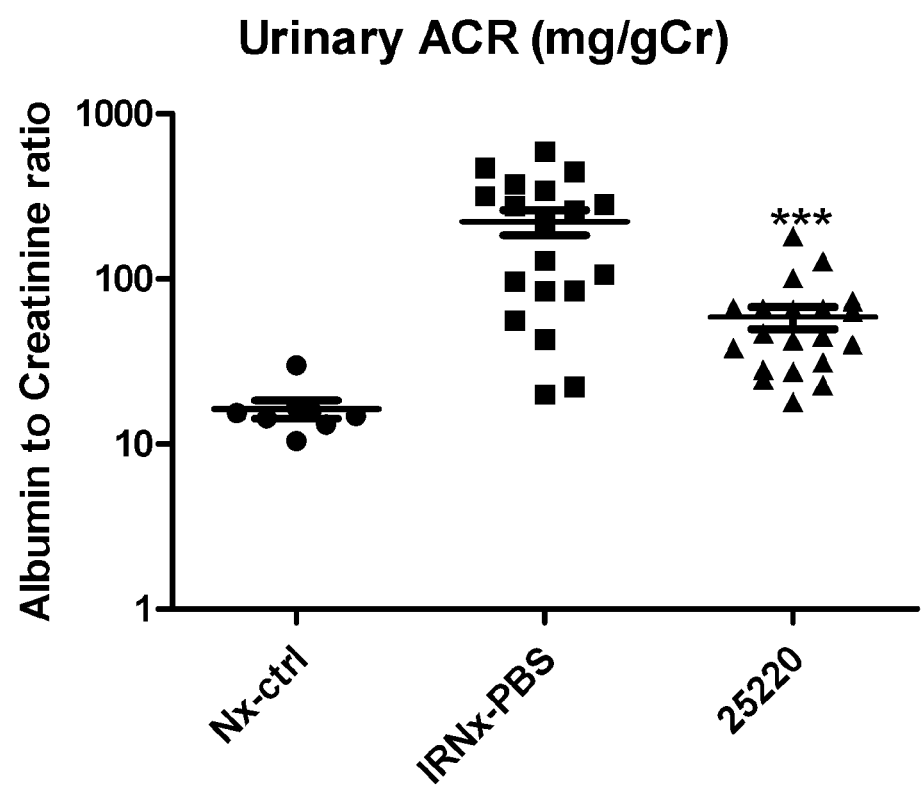

Compound 25220 was also tested in the IR/Nx model. Unilateral IR was induced for a period of 30 minutes. Treatment groups were as follows: sham IR procedure (n=7); IR with PBS administered subcutaneously (n=13); and IR with anti-miR-21 compound 25220 administered subcutaneously at a dose of 20 mg/kg (n=19). PBS or anti-miR was administered on days 2, 3, 4, and 8 following IR. On day 8, the healthy kidney was removed by nephrectomy from each animal, and animals were sacrificed on day 9. Just prior to sacrifice, urine was collected by direct bladder puncture. To assess albuminuria, urinary albumin to creatinine ratio was measured in the urine from each mouse. The results of that experiment are shown in FIG. 5C. In this study, 25220 produced a statistically significant reduction in urinary albumin to creatinine ratio.

Example 5

Survival of IR/Nx Model Mice Following Administration of Anti-miR-21 Compounds

The survival rate of IR/Nx model mice two days after nephrectomy was determined across six different experiments to determine if administration of anti-miR-21 compounds increases survival. In the first three experiments, anti-miR-21 compound was administered on days 5, 6, and 7 after ischemia reperfusion injury, and nephrectomy occurred on day 10 or day 11. In the second three experiments, anti-miR-21 compound was administered on days 2, 3, and 4, and nephrecromy occurred on day 7. The rates of survival of the IR/Nx mice in each experiment are shown in Table H.

TABLE H 36328 increases survival rate of IR/Nx mice two days after nephrectomy.

| | Survival rate 2 days after Nx | | |
|---|---|---|---|
| Day of Nx | PBS | 36328 | Anti-miR-21 dose |
| Day 10 | 50% | 75% | 20 mg/kg |
| Day 7 | 66.7% | 91.7% | 20 mg/kg |

In the first experiment, in which nephrectomy occurred on day 10, the survival rate of PBS-treated mice was 55%, while the survival rate of 36328-treated mice was 75% (P=0.02 using a 1-sided Fisher's Exact Test). In the second experiment, in which nephrectomy occurred on day 7, the survival rate of PBS-treated mice was 52%, while the survival rate of 36328-treated mice was 69% (P=0.11 using a 1-sided Fisher's Exact Test).

Example 6

Anti-miR-21 Compounds

Additional anti-miRs targeted to miR-21 and comprising S-cEt nucleosides were designed with variations in length, as well as in the number, type and placement of modified sugar moieties. These anti-miRs are shown in Table I. Nucleoside patterns III, IV, V and VII are shown in the first three rows of Table I. Nucleoside modifications are indicated as follows: nucleosides not followed by a subscript indicate β-D-deoxyribonucleosides; nucleosides followed by a subscript "E" indicate 2'-MOE nucleosides; nucleosides followed by a subscript "M" indicate 2'-O-methyl nucleosides; nucleosides followed by a subscript "S" indicate S-cEt nucleosides. Each internucleoside linkage is a phosphorothioate internucleoside linkage.

TABLE I

Anti-miR-21 compounds

| Compound # | Nucleoside Pattern | Sequence and Chemistry (superscript "B" indicates bicyclic nucleoside, such as S-cEt nucleoside) | | | | | | | | | | | | | | | | | | SEQ ID NO |
|---|---|---|---|---|---|---|---|---|---|---|---|---|---|---|---|---|---|---|---|---|---|
| | III | R | $N^B$ | $N^Q$ | $N^Q$ | $N^B$ | $N^Q$ | $N^Q$ | $N^Q$ | $N^B$ | $N^Q$ | $N^Q$ | $N^Q$ | $N^B$ | $N^Q$ | $N^Q$ | $N^Q$ | $N^B$ | $N^Y$ | $N^Z$ | |
| | IV | $N^M$ | $N^B$ | $N^Q$ | $N^Q$ | $N^B$ | $N^Q$ | $N^Q$ | $N^Q$ | $N^B$ | $N^Q$ | $N^Q$ | $N^Q$ | $N^B$ | $N^Q$ | $N^Q$ | $N^Q$ | $N^B$ | $N^Y$ | $N^Z$ | |
| | V | $N^M$ | $N^B$ | $N^Q$ | $N^Q$ | $N^B$ | $N^B$ | $N^Q$ | $N^Q$ | $N^B$ | $N^B$ | $N^Q$ | $N^Q$ | $N^B$ | $N^B$ | $N^Q$ | $N^Q$ | $N^B$ | $N^B$ | $N^Z$ | |
| | VII | $N^M$ | $N^B$ | $N^M$ | $N^M$ | $N^B$ | $N^M$ | $N^M$ | $N^M$ | $N^B$ | $N^Q$ | $N^Q$ | $N^Q$ | $N^B$ | $N^Q$ | $N^Q$ | $N^Q$ | $N^B$ | $N^B$ | $N^Z$ | |
| 36039 | III, IV | $A_E$ | $C_S$ | $A_E$ | $T_E$ | $C_S$ | $A_E$ | $G_E$ | $T_E$ | $C_S$ | T | G | A | $U_S$ | A | A | G | $C_S$ | T | $A_S$ | 3 |
| 36731 | III, IV, VII | $A_E$ | $C_S$ | $A_E$ | $T_E$ | $C_S$ | $A_E$ | $G_E$ | $T_E$ | $C_S$ | T | G | A | $U_S$ | A | A | G | $C_S$ | $U_S$ | $A_S$ | 3 |
| 36843 | III, IV, VII | $A_E$ | $C_S$ | $A_E$ | $T_E$ | $C_S$ | $A_E$ | $G_E$ | $T_E$ | $C_S$ | T | $G_M$ | A | $U_S$ | A | $G_M$ | G | $C_S$ | $U_S$ | $A_S$ | 3 |
| 36844 | III, IV, VII | $A_E$ | $C_S$ | $A_E$ | $T_E$ | $C_S$ | $A_E$ | $G_E$ | $T_E$ | $C_S$ | T | $G_M$ | A | $U_S$ | A | $A_M$ | G | $C_S$ | $U_S$ | $T_E$ | 8 |
| 36845 | III, IV, VII | $A_E$ | $C_S$ | $A_E$ | $T_E$ | $C_S$ | $A_E$ | $G_E$ | $T_E$ | $C_S$ | T | G | $A_M$ | $U_S$ | $A_M$ | A | G | $C_S$ | $U_S$ | $A_S$ | 3 |
| 36846 | III, IV, VII | $A_E$ | $C_S$ | $A_E$ | $T_E$ | $C_S$ | $A_E$ | $G_E$ | $T_E$ | $C_S$ | T | G | $A_M$ | $U_S$ | $A_M$ | A | G | $C_S$ | $U_S$ | $T_E$ | 8 |
| 36847 | V | $A_E$ | $C_S$ | A | T | $C_S$ | $A_S$ | G | T | $C_S$ | $U_S$ | G | A | $U_S$ | $A_S$ | A | G | $C_S$ | $U_S$ | $T_E$ | 8 |
| 36842 | | $A_E$ | $C_S$ | $A_E$ | $T_E$ | $C_S$ | $A_E$ | $G_E$ | $T_E$ | $C_S$ | T | $G_S$ | A | $U_S$ | A | $A_S$ | G | $C_S$ | $U_S$ | $A_S$ | 3 |
| 36000 | III, IV | $A_E$ | $C_S$ | A | T | $C_S$ | $A_E$ | $G_E$ | $T_E$ | $C_S$ | T | G | $A_E$ | $U_S$ | $A_E$ | A | G | $C_S$ | $U_S$ | $A_S$ | 3 |
| 36001 | III, IV | $A_E$ | $C_S$ | A | T | $C_S$ | A | $G_E$ | $T_E$ | $C_S$ | T | G | $A_E$ | $U_S$ | $A_E$ | A | G | $C_S$ | $U_S$ | $A_S$ | 3 |
| 36002 | III, IV | $A_E$ | $C_S$ | A | T | $C_S$ | A | G | $T_E$ | $C_S$ | T | G | $A_E$ | $U_S$ | $A_E$ | A | G | $C_S$ | $U_S$ | $A_S$ | 3 |
| 36003 | III, IV | $A_E$ | $C_S$ | A | T | $C_S$ | A | G | T | $C_S$ | T | G | $A_E$ | $U_S$ | $A_E$ | A | G | $C_S$ | $U_S$ | $A_S$ | 3 |
| 36004 | III, IV | $A_E$ | $C_S$ | A | $T_E$ | $C_S$ | $A_E$ | $G_E$ | $T_E$ | $C_S$ | T | G | $A_E$ | $U_S$ | $A_E$ | A | G | $C_S$ | $U_S$ | $T_E$ | 8 |
| 36005 | III, IV | $A_E$ | $C_S$ | A | T | $C_S$ | $A_E$ | $G_E$ | $T_E$ | $C_S$ | T | G | $A_E$ | $U_S$ | $A_E$ | A | G | $C_S$ | $U_S$ | $T_E$ | 8 |
| 36006 | III, IV | $A_E$ | $C_S$ | A | T | $C_S$ | A | $G_E$ | $T_E$ | $C_S$ | T | G | $A_E$ | $U_S$ | $A_E$ | A | G | $C_S$ | $U_S$ | $T_E$ | 8 |
| 36007 | III, IV | $A_E$ | $C_S$ | A | T | $C_S$ | A | G | $T_E$ | $C_S$ | T | G | $A_E$ | $U_S$ | $A_E$ | A | G | $C_S$ | $U_S$ | $T_E$ | 8 |
| 36008 | III, IV | $A_E$ | $C_S$ | A | T | $C_S$ | A | G | T | $C_S$ | T | G | $A_E$ | $U_S$ | $A_E$ | A | G | $C_S$ | $U_S$ | $T_E$ | 8 |
| 36009 | III, IV, VII | $A_E$ | $C_S$ | $A_E$ | $T_E$ | $C_S$ | $A_E$ | $G_E$ | $T_E$ | $C_S$ | T | G | A | $U_S$ | A | A | G | $C_S$ | $U_S$ | | 10 |
| 36010 | III, IV, VII | $A_E$ | $C_S$ | $A_E$ | $T_E$ | $C_S$ | $A_E$ | $G_E$ | $T_E$ | $C_S$ | T | G | A | $U_S$ | $A_M$ | A | G | $C_S$ | $U_S$ | | 10 |
| 36011 | III, IV, VII | $A_E$ | $C_S$ | $A_E$ | $T_E$ | $C_S$ | $A_E$ | $G_E$ | $T_E$ | $C_S$ | T | G | $A_M$ | $U_S$ | A | A | G | $C_S$ | $U_S$ | | 10 |
| 36012 | III, IV, VII | | $C_S$ | $A_E$ | $T_E$ | $C_S$ | $A_E$ | $G_E$ | $T_E$ | $C_S$ | T | G | A | $U_S$ | A | A | G | $C_S$ | $U_S$ | $A_S$ | 9 |
| 36016 | III, IV | $A_E$ | $C_S$ | $A_E$ | $T_E$ | $C_S$ | $A_E$ | $G_E$ | T | $C_S$ | T | G | $A_M$ | $U_S$ | A | A | G | $C_S$ | $U_S$ | $A_S$ | 3 |
| 36017 | III, IV | $A_E$ | $C_S$ | $A_E$ | T | $C_S$ | $A_E$ | $G_E$ | T | $C_S$ | T | G | $A_M$ | $U_S$ | A | A | G | $C_S$ | $U_S$ | $A_S$ | 3 |
| 36018 | III, IV | $A_E$ | $C_S$ | $A_E$ | $T_E$ | $C_S$ | $A_E$ | $G_E$ | T | $C_S$ | T | G | A | $U_S$ | $A_M$ | A | G | $C_S$ | $U_S$ | $A_S$ | 3 |
| 36019 | III, IV | $A_E$ | $C_S$ | $A_E$ | T | $C_S$ | $A_E$ | $G_E$ | T | $C_S$ | T | G | A | $U_S$ | $A_M$ | A | G | $C_S$ | $U_S$ | $A_S$ | 3 |
| 36020 | III, IV | $A_E$ | $C_S$ | $A_E$ | $T_E$ | $C_S$ | $A_E$ | $G_E$ | $T_E$ | $C_S$ | T | G | $A_M$ | $U_S$ | $A_M$ | A | G | $C_S$ | $U_M$ | $A_S$ | 3 |
| 36021 | III, IV | $A_E$ | $C_S$ | $A_E$ | $T_E$ | $C_S$ | $A_E$ | $G_E$ | $T_E$ | $C_S$ | T | G | $A_M$ | $U_S$ | A | A | G | $C_S$ | $U_M$ | $A_S$ | 3 |
| 36022 | III, IV | $A_E$ | $C_S$ | $A_E$ | $T_E$ | $C_S$ | $A_E$ | $G_E$ | T | $C_S$ | T | G | $A_M$ | $U_S$ | A | A | G | $C_S$ | $U_M$ | $A_S$ | 3 |
| 36023 | III, IV | $A_E$ | $C_S$ | $A_E$ | T | $C_S$ | $A_E$ | $G_E$ | T | $C_S$ | T | G | $A_M$ | $U_S$ | A | A | G | $C_S$ | $U_M$ | $A_S$ | 3 |
| 36024 | III, IV | $A_E$ | $C_S$ | $A_E$ | $T_E$ | $C_S$ | $A_E$ | $G_E$ | $T_E$ | $C_S$ | T | G | A | $U_S$ | $A_M$ | A | G | $C_S$ | $U_M$ | $A_S$ | 3 |
| 36025 | III, IV | $A_E$ | $C_S$ | $A_E$ | $T_E$ | $C_S$ | $A_E$ | $G_E$ | T | $C_S$ | T | G | A | $U_S$ | $A_M$ | A | G | $C_S$ | $U_M$ | $A_S$ | 3 |
| 36026 | III, IV | $A_E$ | $C_S$ | $A_E$ | T | $C_S$ | $A_E$ | $G_E$ | T | $C_S$ | T | G | A | $U_S$ | $A_M$ | A | G | $C_S$ | $U_M$ | $A_S$ | 3 |
| 36027 | III, IV | $A_E$ | $C_S$ | $A_E$ | $T_E$ | $C_S$ | $A_E$ | $G_E$ | $T_E$ | $C_S$ | T | G | A | $U_S$ | A | A | G | $C_S$ | $U_M$ | $A_S$ | 3 |
| 36028 | III, IV | $A_E$ | $C_S$ | $A_E$ | $T_E$ | $C_S$ | $A_E$ | $G_E$ | T | $C_S$ | T | G | A | $U_S$ | A | A | G | $C_S$ | $U_M$ | $A_S$ | 3 |
| 36029 | III, IV | $A_E$ | $C_S$ | $A_E$ | T | $C_S$ | $A_E$ | $G_E$ | T | $C_S$ | T | G | A | $U_S$ | A | A | G | $C_S$ | $U_M$ | $A_S$ | 3 |
| 36030 | III, IV | $A_E$ | $C_S$ | $A_E$ | $T_E$ | $C_S$ | $A_E$ | $G_E$ | $T_E$ | $C_S$ | T | G | A | $U_S$ | A | A | G | $C_S$ | $U_M$ | $T_E$ | 8 |
| 36031 | III, IV | $A_E$ | $C_S$ | $A_E$ | $T_E$ | $C_S$ | $A_E$ | $G_E$ | T | $C_S$ | T | G | A | $U_S$ | A | A | G | $C_S$ | $U_M$ | $T_E$ | 8 |
| 36032 | III, IV | $A_E$ | $C_S$ | $A_E$ | T | $C_S$ | $A_E$ | $G_E$ | T | $C_S$ | T | G | A | $U_S$ | A | A | G | $C_S$ | $U_M$ | $T_E$ | 8 |
| 36033 | | $A_E$ | $C_S$ | A | T | $C_S$ | $A_S$ | G | T | $C_S$ | $U_S$ | G | A | $U_S$ | $A_M$ | A | G | $C_S$ | $U_S$ | $A_S$ | 3 |
| 36034 | | $A_E$ | $C_S$ | A | T | $C_S$ | $A_S$ | G | T | $C_S$ | $U_M$ | G | A | $U_S$ | $A_M$ | A | G | $C_S$ | $U_S$ | $A_S$ | 3 |
| 36035 | III, IV | $A_E$ | $C_S$ | A | T | $C_S$ | $A_M$ | G | T | $C_S$ | $U_M$ | G | A | $U_S$ | $A_M$ | A | G | $C_S$ | $U_S$ | $A_S$ | 3 |
| 36040 | | $A_E$ | $C_S$ | A | T | $C_S$ | $A_S$ | G | T | $C_S$ | $T_E$ | G | A | $U_S$ | $A_E$ | A | G | $C_S$ | $U_S$ | $A_S$ | 3 |
| 36041 | III, IV | $A_E$ | $C_S$ | A | T | $C_S$ | $A_E$ | G | T | $C_S$ | $T_E$ | G | A | $U_S$ | $A_E$ | A | G | $C_S$ | $U_S$ | $A_S$ | 3 |
| 36045 | III, IV | $A_E$ | $C_S$ | A | $T_E$ | $C_S$ | $A_E$ | $G_E$ | $T_E$ | $C_S$ | T | G | $A_M$ | $U_S$ | $A_M$ | A | G | $C_S$ | $U_S$ | $T_E$ | 8 |
| 36046 | III, IV | $A_E$ | $C_S$ | A | T | $C_S$ | $A_E$ | $G_E$ | $T_E$ | $C_S$ | T | G | $A_M$ | $U_S$ | $A_M$ | A | G | $C_S$ | $U_S$ | $T_E$ | 8 |
| 36047 | III, IV | $A_E$ | $C_S$ | A | T | $C_S$ | A | $G_E$ | $T_E$ | $C_S$ | T | G | $A_M$ | $U_S$ | $A_M$ | A | G | $C_S$ | $U_S$ | $T_E$ | 8 |
| 36048 | III, IV | $A_E$ | $C_S$ | A | T | $C_S$ | A | G | $T_E$ | $C_S$ | T | G | $A_M$ | $U_S$ | $A_M$ | A | G | $C_S$ | $U_S$ | $T_E$ | 8 |
| 36049 | | $A_E$ | $C_S$ | A | T | $C_S$ | $A_S$ | G | T | $C_S$ | $U_S$ | G | A | $U_S$ | $A_M$ | A | G | $C_S$ | $U_S$ | $T_E$ | 8 |
| 36050 | | $A_E$ | $C_S$ | A | T | $C_S$ | $A_S$ | G | T | $C_S$ | $U_M$ | G | A | $U_S$ | $A_M$ | A | G | $C_S$ | $U_S$ | $T_E$ | 8 |
| 36051 | III, IV | $A_E$ | $C_S$ | A | T | $C_S$ | $A_M$ | G | T | $C_S$ | $U_M$ | G | A | $U_S$ | $A_M$ | A | G | $C_S$ | $U_S$ | $T_E$ | 8 |
| 36055 | V | $A_E$ | $C_S$ | A | T | $C_S$ | $A_S$ | G | T | $C_S$ | $U_S$ | G | A | $U_S$ | $A_S$ | A | G | $C_S$ | $U_S$ | | 11 |
| 36239 | | $A_E$ | $C_S$ | A | T | $C_S$ | $A_S$ | G | T | $C_S$ | $U_S$ | G | A | $U_S$ | $A_E$ | A | G | $C_S$ | $U_S$ | $A_S$ | 3 |
| 36968 | III, IV | $A_E$ | $C_S$ | $A_E$ | $T_E$ | $C_S$ | $A_E$ | $G_E$ | $T_E$ | $C_S$ | T | G | A | $U_S$ | A | A | G | $C_S$ | $U_S$ | $A_S$ | 3 |
| 36969 | III, IV | $A_E$ | $C_S$ | $A_E$ | T | $C_S$ | $A_E$ | $G_E$ | T | $C_S$ | T | G | A | $U_S$ | A | A | G | $C_S$ | $U_S$ | $A_S$ | 3 |
| 36970 | III, IV, VII | $A_E$ | $C_S$ | $A_E$ | $T_E$ | $C_S$ | $A_E$ | $G_E$ | $T_E$ | $C_S$ | T | G | A | $U_S$ | A | A | G | $C_S$ | $U_S$ | $T_E$ | 8 |
| 36971 | III, IV | $A_E$ | $C_S$ | $A_E$ | $T_E$ | $C_S$ | $A_E$ | $G_E$ | T | $C_S$ | T | G | A | $U_S$ | A | A | G | $C_S$ | $U_S$ | $T_E$ | 8 |

TABLE I-continued

Anti-miR-21 compounds

| Compound # | Nucleoside Pattern | Sequence and Chemistry (superscript "B" indicates bicyclic nucleoside, such as S-cEt nucleoside) | SEQ ID NO |
|---|---|---|---|
| 36972 | III, IV | $A_E$ $C_S$ $A_E$ T $C_S$ $A_E$ $G_E$ T $C_S$ T G A $U_S$ A A G $C_S$ $U_S$ $T_E$ | 8 |
| 36973 | III, IV | $A_E$ $C_S$ A $T_E$ $C_S$ $A_E$ $G_E$ $T_E$ $C_S$ T G A $U_S$ A A G $C_S$ $U_S$ $A_S$ | 3 |
| 36974 | III, IV | $A_E$ $C_S$ $A_E$ T $C_S$ $A_E$ $G_E$ $T_E$ $C_S$ T G A $U_S$ A A G $C_S$ $U_S$ $A_S$ | 3 |
| 36975 | III, IV | $A_E$ $C_S$ $A_E$ $T_E$ $C_S$ A $G_E$ $T_E$ $C_S$ T G A $U_S$ A A G $C_S$ $U_S$ $A_S$ | 3 |
| 36976 | III, IV | $A_E$ $C_S$ $A_E$ $T_E$ $C_S$ $A_E$ G $T_E$ $C_S$ T G A $U_S$ A A G $C_S$ $U_S$ $A_S$ | 3 |
| 36977 | III, IV | $A_E$ $C_S$ A T $C_S$ $A_E$ $G_E$ $T_E$ $C_S$ T G A $U_S$ A A G $C_S$ $U_S$ $A_S$ | 3 |
| 36978 | III, IV | $A_E$ $C_S$ $A_E$ $T_E$ $C_S$ A G $T_E$ $C_S$ T G A $U_S$ A A G $C_S$ $U_S$ $A_S$ | 3 |
| 36979 | III, IV | $A_E$ $C_S$ $A_E$ $T_E$ $C_S$ $A_E$ G T $C_S$ T G A $U_S$ A A G $C_S$ $U_S$ $A_S$ | 3 |
| 36980 | III, IV | $A_E$ $C_S$ A T $C_S$ A $G_E$ $T_E$ $C_S$ T G A $U_S$ A A G $C_S$ $U_S$ $A_S$ | 3 |
| 36981 | III, IV | $A_E$ $C_S$ A T $C_S$ A G $T_E$ $C_S$ T G A $U_S$ A A G $C_S$ $U_S$ $A_S$ | 3 |
| 36982 | III, IV, VII | $A_E$ $C_S$ $A_E$ $T_E$ $C_S$ $A_E$ $G_E$ $T_E$ $C_S$ T G A $U_S$ A A G $C_S$ $T_E$ $A_S$ | 3 |
| 36984 | III, IV, VII | $A_E$ $C_S$ $A_E$ $T_E$ $C_S$ $A_E$ $G_E$ $T_E$ $C_S$ T G A $U_S$ A A $G_E$ $C_S$ $U_S$ $A_S$ | 3 |
| 36985 | III, IV, VII | $A_E$ $C_S$ $A_E$ $T_E$ $C_S$ $A_E$ $G_E$ $T_E$ $C_S$ T G A $U_S$ A $A_E$ G $C_S$ $U_S$ $A_S$ | 3 |
| 36986 | III, IV, VII | $A_E$ $C_S$ $A_E$ $T_E$ $C_S$ $A_E$ $G_E$ $T_E$ $C_S$ T G A $U_S$ $A_E$ A G $C_S$ $U_S$ $A_S$ | 3 |
| 36988 | III, IV, VII | $A_E$ $C_S$ $A_E$ $T_E$ $C_S$ $A_E$ $G_E$ $T_E$ $C_S$ T G $A_E$ $U_S$ A A G $C_S$ $U_S$ $A_S$ | 3 |
| 36989 | III, IV, VII | $A_E$ $C_S$ $A_E$ $T_E$ $C_S$ $A_E$ $G_E$ $T_E$ $C_S$ T $G_E$ A $U_S$ A A G $C_S$ $U_S$ $A_S$ | 3 |
| 36990 | III, IV, VII | $A_E$ $C_S$ $A_E$ $T_E$ $C_S$ $A_E$ $G_E$ $T_E$ $C_S$ $T_E$ G A $U_S$ A A G $C_S$ $U_S$ $A_S$ | 3 |
| 36992 | III, IV, VII | $A_E$ $C_S$ $A_E$ $T_E$ $C_S$ $A_E$ $G_E$ $T_E$ $C_S$ T G A $U_S$ $A_M$ A G $C_S$ $U_S$ $A_S$ | 3 |
| 36993 | III, IV, VII | $A_E$ $C_S$ $A_E$ $T_E$ $C_S$ $A_E$ $G_E$ $T_E$ $C_S$ T G $A_M$ $U_S$ A A G $C_S$ $U_S$ $A_S$ | 3 |
| 36994 | III, IV | $A_E$ $C_S$ A $T_E$ $C_S$ $A_E$ $G_E$ $T_E$ $C_S$ T G $A_M$ $U_S$ $A_M$ A G $C_S$ $U_S$ $A_S$ | 3 |
| 36995 | III, IV | $A_E$ $C_S$ A T $C_S$ $A_E$ $G_E$ $T_E$ $C_S$ T G $A_M$ $U_S$ $A_M$ A G $C_S$ $U_S$ $A_S$ | 3 |
| 36996 | III, IV | $A_E$ $C_S$ A T $C_S$ A $G_E$ $T_E$ $C_S$ T G $A_M$ $U_S$ $A_M$ A G $C_S$ $U_S$ $A_S$ | 3 |
| 36997 | III, IV | $A_E$ $C_S$ A T $C_S$ A G $T_E$ $C_S$ T G $A_M$ $U_S$ $A_M$ A G $C_S$ $U_S$ $A_S$ | 3 |
| 36998 | III, IV | $A_E$ $C_S$ A T $C_S$ A G T $C_S$ T G $A_M$ $U_S$ $A_M$ A G $C_S$ $U_S$ $A_S$ | 3 |
| 36999 | III, IV | $A_E$ $C_S$ A $T_E$ $C_S$ $A_E$ $G_E$ $T_E$ $C_S$ T G $A_E$ $U_S$ $A_E$ A G $C_S$ $U_S$ $A_S$ | 3 |

Figure 6A:
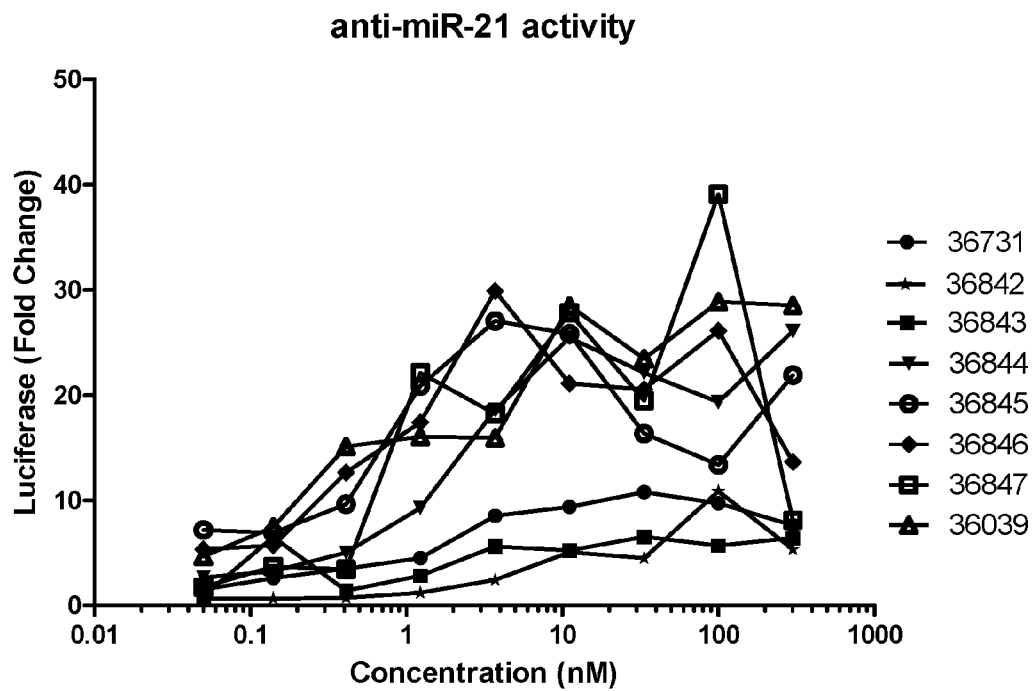
FIGS. 6A and 6B show (A) luciferase activity of anti-miR-21 compounds and (B) anti-proliferative effects of anti-miR-21 compounds in cultured cells, as described in Example 6.

Compounds selected from Table I were evaluated for their inhibitory effects on miR-21 activity in an in vitro luciferase assay. The assay was performed as described herein, and the results are shown in Table J and FIG. 6A.

TABLE J

Anti-miR-21 compound luciferase data

| Anti-miR concentration nM | 36731 | 36842 | 36843 | 36844 | 36845 | 36846 | 36847 | 36039 |
|---|---|---|---|---|---|---|---|---|
| 300 | 7.63 | 5.34 | 6.43 | 26.07 | 21.90 | 13.64 | 8.08 | 28.53 |
| 100 | 9.72 | 10.87 | 5.71 | 19.33 | 13.36 | 26.13 | 39.10 | 28.85 |
| 33.33 | 10.76 | 4.50 | 6.52 | 22.11 | 16.35 | 20.54 | 19.46 | 23.44 |
| 11.11 | 9.38 | 5.06 | 5.21 | 25.46 | 25.83 | 21.08 | 27.84 | 28.51 |
| 3.7 | 8.53 | 2.45 | 5.62 | 18.61 | 27.05 | 29.88 | 18.21 | 15.93 |
| 1.23 | 4.49 | 1.20 | 2.84 | 9.28 | 20.86 | 17.41 | 22.11 | 16.05 |
| 0.41 | 3.51 | 0.75 | 1.41 | 5.04 | 9.64 | 12.64 | 3.44 | 15.12 |
| 0.14 | 2.60 | 0.65 | 6.50 | 3.24 | 6.89 | 5.69 | 3.71 | 7.46 |
| 0.05 | 1.52 | 0.67 | 0.90 | 2.66 | 7.18 | 5.33 | 1.74 | 4.66 |
| 0 | 0.33 | 0.36 | 4.34 | 1.21 | 1.07 | 1.19 | 0.85 | 0.90 |

Based on the data in Table J and data from repeat experiments, it was observed that compounds 36731, 36039, 36846 and 36847 consistently inhibited miR-21 in the luciferase assay.

Figure 6B:
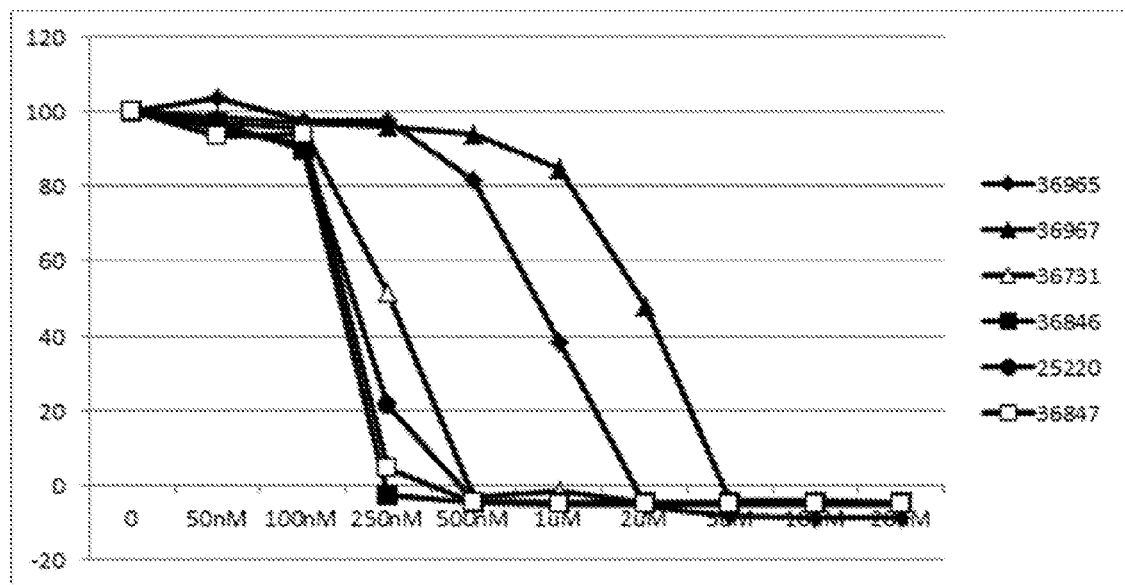

Certain anti-miR-21 compounds were additionally tested for their effects on cell proliferation in an in vitro assay. Two mismatch control anti-miRs were used (36965 $G_E G_S A_E A_E U_S C_E^\ell T_E T_E A_S ACTA_S GACU_S A_S C_S$, SEQ ID NO: 15; 36967 $G_E A_S A_E T_E A_S A_E T_E A_E U_S AACC_S CCTG_S G_S U_S$, SEQ ID NO: 16). The human adenocarcinoma cell line SK-Hep1 was used in this experiment. SK-Hep1 were plated onto collagen-coated 96 well plates at a density of 500 cells per well. The following day, cells were treated with anti-miR at a concentration ranging from 50 nM to 20 uM (n=6 wells for each treatment). No transfection reagent was used. Cell viability was measured using the CellTiter-Glo® Luminescent Cell Viability Assay. Results were calculated as percent of viable cells relative to untreated control. As shown in Table K and FIG. 6B, compounds 36731, 36846, 36847 and 25220 reduced cell viability in a concentration-dependent manner.

TABLE K

Anti-proliferative effects of anti-miR-21 compounds

| | Anti-miR Concentration | | | | | | | | |
|---|---|---|---|---|---|---|---|---|---|
| Compound # | 50 nM | 100 nM | 250 nM | 500 nM | 1 uM | 2 uM | 5 uM | 10 uM | 20 uM |
| 36965 | 103.87 | 97.48 | 97.64 | 81.87 | 38.01 | 0 | 0 | 0 | 0 |
| 36967 | 98.50 | 97.10 | 95.93 | 94.11 | 84.90 | 47.72 | 0 | 0 | 0 |

TABLE K-continued

Anti-proliferative effects of anti-miR-21 compounds

| Compound # | Anti-miR Concentration | | | | | | | | |
|---|---|---|---|---|---|---|---|---|---|
| | 50 nM | 100 nM | 250 nM | 500 nM | 1 uM | 2 uM | 5 uM | 10 uM | 20 uM |
| 36731 | 96.92 | 95.53 | 51.74 | 0 | 0 | 0 | 0 | 0 | 0 |
| 36846 | 96.95 | 90.07 | 0 | 0 | 0 | 0 | 0 | 0 | 0 |
| 25220 | 95.54 | 91.35 | 21.37 | 0 | 0 | 0 | 0 | 0 | 0 |
| 36847 | 93.61 | 93.98 | 4.41 | 0 | 0 | 0 | 0 | 0 | 0 |

Compounds that reduce cell viability are candidate therapeutic agents for the treatment of cancer.

Figure 7A:
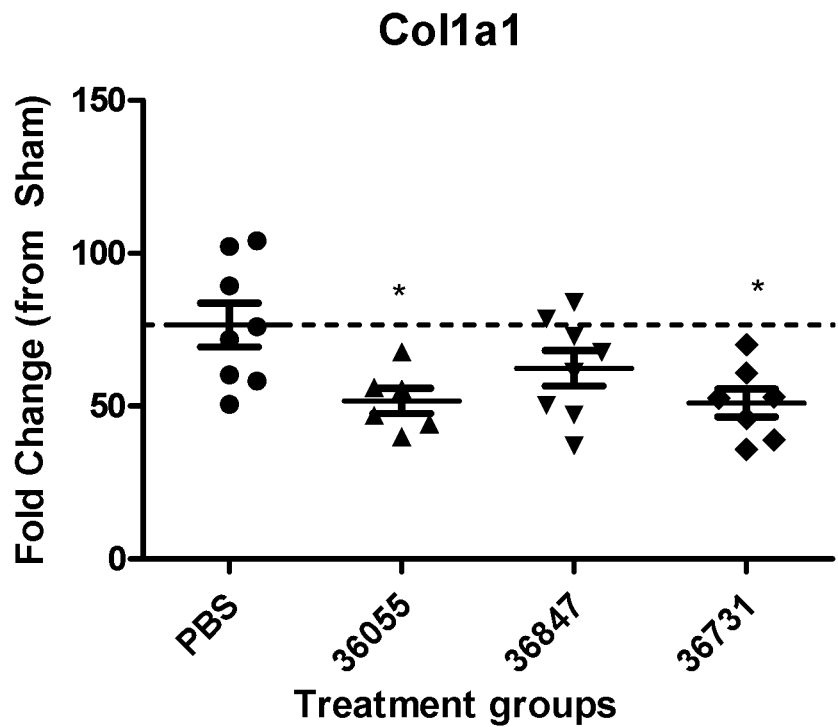
FIGS. 7A and 7B show the change in (A) collagen 1A1 and (B) collagen 3A1 expression in kidneys of UUO model mice administered certain anti-miR-21 compounds, as described in Example 6.
Figure 7B:
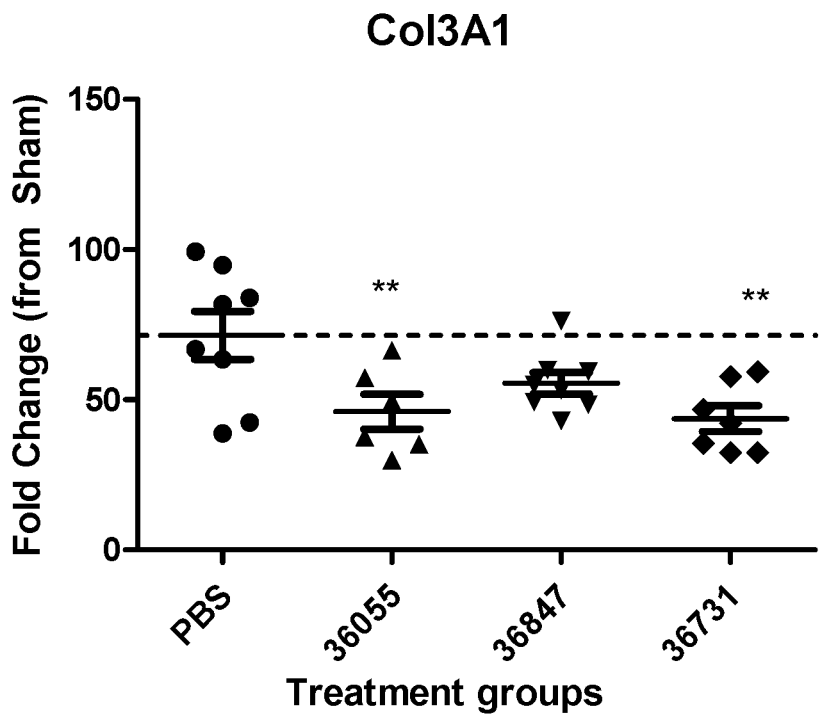

To evaluate in vivo activity in a fibrosis model, certain compounds was tested in the UUO model. Groups of animals were treated as follows: sham surgery (n=4), UUO with PBS (n=8), or UUO with anti-miR-21 compound (n=8). Relative to the day of the UUO procedure, PBS or anti-miR-21 compound was administered at days −5, −3, and +3. Anti-miR-21 compounds were administered at a dose of 20 mg/kg. As the anti-miR compounds were administered prior to the UUO procedure, this dosing regimen is considered a prophylactic treatment. At day 10 following the UUO procedure, animals were sacrificed and kidney was isolated for measurement of collagen expression. Collagen expression was measured by real-time PCR and normalized first to GAPDH and then to the sham control animals. Statistical significance was determined according to a 1-way ANOVA test. As shown in FIG. 7, treatment with 36731 and 36055 reduced the expression of collagen 1A1 (FIG. 7A) and collagen 3A1 (FIG. 7B) in a statistically significant manner, relative to sham-treated animals (*=p<0.05; **=p<0.01). Compounds 36847 reduced collagen 1A1 and collagen 3A1 expression, although not in a statistically significant manner in this study.

Viscosity of certain compounds was also determined. Compounds were dissolved in water. Using routing methods, oligonucleotide concentration was calculated gravimetrically (mg/g) and viscosity (cP) was measured using a viscometer. Results are shown in Table L.

TABLE L

Anti-miR-21 compound viscosity

| Compound # | Viscosity cP | Concentration mg/g |
|---|---|---|
| 36731 | 81 | 153 |
| 36847 | 128 | 130 |
| 36846 | 66 | 150 |

Compounds 36731 and 36846 exhibited relatively low viscosity, compared to 36847 and other compounds described herein.

The metabolic stability of certain compounds was determined. In an ex vivo assay, performed as described above, approximately 89% of full-length 36731 compound was detected at the end of the assay. Thus, 36731 is a highly stable compound in the presence of nucleases.

Example 7

Xenograft Models

Human xenograft models are often used to measure the in vivo efficacy of potential cancer therapies.

Cell-line based xenograft models are prepared by injecting human cancer cells into immunodeficient mice. The injected cells form tumors, and the effects of potential anti-cancer agents can be evaluated for effects on parameters including tumor size, tumor number, tumor architecture and metastatic potential. Cells are grown in culture, and then harvested for injection into a mouse. The cells are from a cancer cell line (e.g. SK-Hep1, Huh7, HeLa293, Hep3B, SNU). To initiate tumor growth, approximately $5 \times 10^6$ cells are injected subcutaneously into the flank of an immunodeficient mouse (e.g. a SCID mouse or an athymic nude mouse). The cells are allowed to form tumors of an average volume of up to 75 mm$^2$.

Patient-derived tumor tissue xenograft models (patient-derived xenograft or PDX models) are established by transplanting an explant of a human tumor into an immunodeficient mouse. To preserve as many of the original tumor characteristics as possible, the explant may be propagated from one mouse to another, but is generally not propagated in cell culture.

Anti-miR-21 compounds are tested for their anti-cancer effects in a human xenograft model. When tumors are of the appropriate size, mice are treated as follows: PBS (n=5 to 10); anti-miR-21 (n=5 to 10); or anti-miR-21 mismatch (optional; n=5 to 10). Treatments are administered subcutaneously, up to 3 times per week for up to 12 weeks.

Tumor size is measured one to two times per week, using calipers, for example. Body weight is measured two to three times per week. Blood is collected weekly and at the end of the study. Tumor and other tissues are collected at the end of the study.

A reduction in tumor size in tumor size is observed in anti-miR-21-treated mice, relative to PBS-treated mice, suggesting that anti-miR-21 is a therapeutic agent that can be used for the treatment of cancer.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, GENBANK® accession numbers, and the like) cited in the present application is specifically incorporated herein by reference in its entirety.

What is claimed is:

1. A modified oligonucleotide consisting of 19 linked nucleosides and having the structure:

(SEQ ID NO: 3)
5'-$A_EC_SA_ET_EC_SA_EG_ET_EC_S$TGAU$_S$AAGC$_S$U$_S$A$_S$-3', wherein nucleosides not followed by a subscript are β-D-deoxyribonucleosides; nucleosides followed by a subscript "E" are 2'-methoxyethyl (2'-MOE) nucleosides; and nucleosides followed by a subscript "S" are S-constrained ethyl (S-cEt) nucleosides; and wherein each internucleoside linkage is a phosphorothioate linkage.

2. A pharmaceutical composition comprising the modified oligonucleotide of claim 1 and a pharmaceutically acceptable diluent.

3. The pharmaceutical composition of claim 2, which is a sterile aqueous solution.

4. A pharmaceutical composition consisting essentially of a modified oligonucleotide in a sterile aqueous solution, wherein the modified oligonucleotide consists of 19 linked nucleosides and has the structure:

(SEQ ID NO: 3)
5'-$A_EC_SA_ET_EC_SA_EG_ET_EC_S$TGAU$_S$AAGC$_S$U$_S$A$_S$-3', wherein nucleosides not followed by a subscript are β-D-deoxyribonucleosides; nucleosides followed by a subscript "E" are 2'-methoxyethyl (2'-MOE) nucleosides; and nucleosides followed by a subscript "S" are S-constrained ethyl (S-cEt) nucleosides; and wherein each internucleoside linkage is a phosphorothioate linkage.

5. A lyophilized composition comprising a modified oligonucleotide consisting of 19 linked nucleosides and having the structure:

(SEQ ID NO: 3)
5'-$A_EC_SA_ET_EC_SA_EG_ET_EC_S$TGAU$_S$AAGC$_S$U$_S$A$_S$-3', wherein nucleosides not followed by a subscript are β-D-deoxyribonucleosides; nucleosides followed by a subscript "E" are 2'-methoxyethyl (2'-MOE) nucleosides; and nucleosides followed by a subscript "S" are S-constrained ethyl (S-cEt) nucleosides; and wherein each internucleoside linkage is a phosphorothioate linkage.

6. A lyophilized composition consisting essentially of a modified oligonucleotide consisting of 19 linked nucleosides and having the structure:

(SEQ ID NO: 3)
5'-$A_EC_SA_ET_EC_SA_EG_ET_EC_S$TGAU$_S$AAGC$_S$U$_S$A$_S$-3', wherein nucleosides not followed by a subscript are β-D-deoxyribonucleosides; nucleosides followed by a subscript "E" are 2'-methoxyethyl (2'-MOE) nucleosides; and nucleosides followed by a subscript "S" are S-constrained ethyl (S-cEt) nucleosides; and wherein each internucleoside linkage is a phosphorothioate linkage.

* * * * *